US007078376B1

(12) United States Patent
Thompson

(10) Patent No.: US 7,078,376 B1
(45) Date of Patent: Jul. 18, 2006

(54) THERAPEUTIC METHODS FOR TREATING SUBJECTS WITH A RECOMBINANT ERYTHROPOIETIN HAVING HIGH ACTIVITY AND REDUCED SIDE EFFECTS

(75) Inventor: Lawrence H. Thompson, Tequesta, FL (US)

(73) Assignee: Baxter Healthcare S.A., Zurich (CH)

( * ) Notice: Subject to any disclaimer, the term of this patent is extended or adjusted under 35 U.S.C. 154(b) by 672 days.

(21) Appl. No.: 09/637,962

(22) Filed: Aug. 11, 2000

(51) Int. Cl.
- *A61K 38/00* (2006.01)
- *A61K 38/18* (2006.01)
- *C12N 5/00* (2006.01)
- *C12N 15/00* (2006.01)
- *C07K 14/505* (2006.01)

(52) U.S. Cl. .......................... 514/2; 530/397; 435/69.1; 435/325; 435/320.1

(58) Field of Classification Search ..................... 514/2; 435/69.1, 325, 320.1; 530/397, 395
See application file for complete search history.

(56) References Cited

U.S. PATENT DOCUMENTS

| | | | | |
|---|---|---|---|---|
| 4,703,008 | A | | 10/1987 | Lin |
| 5,661,125 | A | * | 8/1997 | Strickland ...................... 514/8 |
| 5,688,679 | A | * | 11/1997 | Powell ..................... 435/240.2 |
| 5,955,422 | A | | 9/1999 | Lin |
| 2002/0037832 | A1 | | 3/2002 | Nielsen et al. |

FOREIGN PATENT DOCUMENTS

| | | |
|---|---|---|
| EP | 0 813 877 A2 | 12/1997 |
| WO | WO 88/00241 A1 | 1/1988 |
| WO | WO 00/24893 A2 | 5/2000 |
| WO | WO 00/35475 A2 | 6/2000 |
| WO | WO 01/82952 A2 | 11/2001 |
| WO | WO 01/91780 A1 | 12/2001 |

OTHER PUBLICATIONS

Kveder et al. Experiences in Clinical Testing and Use of Recombinant Human Erythropoietin (r–Hu–EPO). Farmacevtski Vestni 47/SPEC.ISS., pp. 163–171, (1996). written in Slovene.*

Kveder et al. Experiences in Clinical Testing and Use of Recombinant Human Erythropoietin (r–Hu–EPO). Farmacevtski Vestni 47/SPEC.ISS., pp. 163–171, (1996). English translation.*

Acharya et al., Effect of Low Dose Recombinant Human Omega Erythropoietin (rHuEPO) on Anaemia in Patients with Hemodialysis, Journal of the Association of Physicians of India, (1995), pp. 539–542, vol. 43:8.

Biesma, D.H., Erythropoietin Treatment for Non–Uremic Patients: A Personal View, The Netherlands Journal of Medicine, (1999), pp. 10–15, vol. 54.

Biesma, D.H. et al., Lower Homologous Blood Requirement in Autologous Blood Donors After Treatment with Recombinant Human Erythropoietin, The Lancet, (1994), pp. 367–370, vol. 344.

Bren, A. et al., A Comparison Between Epoetin Omega and Epoetin Alfa in the Correction of Anemia in Hemodialysis Patients: A Prospective, Controlled Crossover Study, Artificial Organs, (2002), pp. 91–97, vol. 26:2.

Bren, A.F. et al., Experiences with Epoetin Omega and Epoetin Alfa in Hemodialysis Patients, J Am Soc Nephrol, A1813, (2001), p. 352A, vol. 12.

Canadian Erythropoietin Study Group, Association Between Recombinant Human Erythropoietin and Quality of Life and Exercise Capacity of Patients Receiving Haemodialysis, BMJ, (1990), pp. 573–578, vol. 300.

Castelli, G. et al., Detection of Anti–Erythropoietin Antibodies in Haemodialysis Patients Treated with Recombinant Human–Erythropoietin, Pharmacological Research, (2000), pp. 313–318, vol. 41:3.

Choi, D. et al., Erythropoietin: Physico– and Biochemical Analysis, Journal of Chromatography B: BioMedical Applications, (1996), Abstract.

Cummings, M.N. et al., Subcutaneous Erythropoietin Alpha (Eprex) Is More Painful Than Erythropoientin Beta (Recormon), Nephrol Dial Transplant, (1998), p. 817, vol. 13.

(Continued)

*Primary Examiner*—Elizabeth C. Kemmerer
*Assistant Examiner*—Regina M. DeBerry
(74) *Attorney, Agent, or Firm*—Senniger Powers

(57) ABSTRACT

The invention discloses several novel therapeutic properties and methods of treatment using the recombinant erythropoietin prepared by expression from the Apa I restriction fragment of human genomic erythropoietin DNA transformed into baby hamster kidney cells (BHK) according to U.S. Pat. No. 5,688,697 to Powell. This recombinant erythropoietin designated herein as Epoetin Omega is shown to possesses several unexpected and superior qualities over other recombinant erythropoietins such as those designated Epoetin Alfa and Beta which are prepared from genomic or cDNA expressed in Chinese Hamster Ovary (CHO) according to U.S. Pat. Nos. 4,703,008 and 5,955,422 to Lin. The superior properties of Epoetin Omega include, but are not limited to, a much higher potency, a much more rapid response (i.e., no latency), longer effective serum levels, much lower antigenicity in human subjects, therapeutic activity in subjects non-responsive to the other epoetins, fewer adverse side effects such as incidents of thrombosis, reduced nausea, reduced pain at the site of injection, reduction in body pain, and most significantly, the absence of, or reduced risk of, increased blood pressure or hypertension. These novel properties provide for novel therapeutic methods including, treatment of anemia and treatment of conditions other than anemia such as fatigue or vascular pain, treatment in patients adversely effected by hypertension such as patients with heart conditions or at increased risk of thrombosis, treatment in oncology settings with and without chemotherapy or radiation therapy, and treatment with novel dosing regiments that include much lower doses and lower administration frequencies of as few as once per week or less.

25 Claims, 37 Drawing Sheets

OTHER PUBLICATIONS

Faris, P.M. et al., The Effects of Recombinant Human Erythropoietin on Perioperative Transfusion Requirements In Patients Having a Major Orthopaedic Operation, The Journal of Bone and Joint Surgery, (1996), pp. 62–72, vol. 78–A:1.

Faulds, D. et al., Epoetin (Recombinant Human Erythropoietin) A Review of its Pharmacodynamic and Pharmacokinetic Properties and Therapeutic Potential in Anaemia and the Stimulation of Erythropoiesis, Drugs, (1989), pp. 863–899, vol. 38:6.

Frenken, L.A.M. et al., Assessment of Pain After Subcutaneous Injection of Erythropoietin in Patients Receiving Haemodialysis, BMJ, (1991), p. 288, vol. 303.

Fulton, B. et al., Mycophenolate Mofetil—A Review of its Pharmacodynamic and Pharmacokinetic Properties and Clinical Efficacy in Renal Transplantation, Drugs, (1996), pp. 278–298, vol. 51:2.

Halstenson, C.E. et al., Comparative Pharmacokinetics and Pharmacodynamics of Epoetin Alfa and Epoetin Beta, Clin Pharmacol Ther, (1991), pp. 702–712, vol. 50.

Hendriks, M.W.G. et al., Is Recormon® Less Painful Than Eprex® After Subcutaneous Administration?, Pharmaceutisch Weekblad Scientific Edition, (1992), pp. 55–58, vol. 14:2.

Ludwig, H., Epoetin in Cancer-Related Anaemia, Nephrol Dial Transplant, (1999), pp. 85–92, vol. 14:2.

MacDougall, I.C. et al., Pharmacokinetics of Novel Erythropoiesis Stimulating Protein Compared with Epoetin Alfa in Dialysis Patients, J Am Soc Nephrol, (1999), pp. 2392–2395, vol. 10.

Markham, A. et al., Epoetin Alfa—A Review of its Pharmacodynamic and Pharmocokinetic Properties and Therapeutic Use in Nonrenal Applications, Drugs, pp. 232–254, vol. 49:2.

Milutinovic, S. et al., Chronic Renal Failure: Anaemia, Erythropoietin-Induced Hypertension in Dialyzed Uremics is Influenced by Glycosylation Patterns of the Molecule, Nephrology Dialysis Transplantation, (2001), p. A91, vol. 16:6, Abstract.

Milutinovic, S. et al., Dialysis: Anaemia and Erythropoietin Treatment, Differences in Glycosylation Structures Have an Important Impact on Potency and Pharmacokinetics of Erythropoietin (EPO) in Dialyzed Uremics, Nephrology Dialysis Transplantation, (2000), p. A156, vol. 15:9, Abstract.

Milutinovic, S. et al., Dialysis: Complications of Hemodialysis, Efficacy and Pharmacokinetics of Human Erythropoietins in Dialyzed Uremic Patients Depends on Glycosylation Pattern of the Molecule, J Am Soc Nephrol, A1512, (2000), p. 289A, vol. 11.

Milutinovic, S. et al., Erythropoietin (EPO) Omega Improves Cognitive Functioning and Quality of Life in Dialysis Patients in Comparison to ALFA, J Am Soc Nephrol, (2002), p. 178A, vol. 13, Abstract.

Milutinovic, S. et al., Once Weekly Erythropoietin Omega Treatment is Safe and as Effective as Twice Weekly Regimen in correcting Anemia of Dialyzed Patients, Nephrology Dialysis Transplantation, M315, (2002), p. 136, vol. 17, Abstract.

Miyake, T. et al., Purification of Human Erythropoietin, The Journal of Biological Chemistry, (1977), pp. 5558–5564, vol. 252:15.

Nimitz, M. et al., Identification and Structural Characterization of a Mannose-6-Phosphate Containing Oligomannosidic N-Glycan from Human Erythropoietin Secreted by Recombinant BHK-21 Cells, FEBS Letters, (1995), pp. 203–208, vol. 365.

Nimitz, M. et al., Structures of Sialylated Oligosaccharides of Human Erythropoietin Expressed in Recombinant BHK-21 Cells, Eru. J. Biochem., (1993), pp. 39–56, vol. 213.

Peces, R. et al., Antibodies Against Recombinant Human Erythropoietin in a Patient with Erythropoietin-Resistant Anemia, The New England Journal of Medicine, (1996), pp. 523–524, vol. 335:7.

Sans, T. et al., Effectiveness of Very Low Doses of Subcutaneous Recombinant Human Erythropoietin in Facilitating Autologous Blood Donation Before Orthopedic Surgery, Transfusion, (1996), pp. 822–826, vo. 36:9.

Sikole, A. et al., Epoetin Omega for Treatment of Anemia in Maintenance Hemodialysis Patients, Clinical Nephrology, pp. 237–245, vol. 57.

Storring, P.L. et al., Epoetin Alfa and Beta Differ in Their Erythropoietin Isoform Compositions and Biological Properties, British Journal of Haematology, (1998), pp. 79–89, vol. 100.

Sytkowski, A.J. et al., Biological Activity and Structural Stability of N-Deglycosylated Recombinant Human Erythropoietin, Biochemical and Biophysical Research Communications, (1991), pp. 698–704, vol. 176:2.

Tsuda, E. et al., The Role of Carbohydrate in Recombinant Human Erythropoietin, Eur. J. Biochem., (1990), pp. 405–411, vol. 188.

Veys, N. et al., Pain at the Injection Site of Subcutaneously Administered Erythropoietin: Phosphate-Buffered Epoetin Alpha Compared to Citrate-Buffered Epoetin Alpha and Epoetin Beta, Clinical Nephrology, (1998), pp. 41–44, vol. 49:1.

Veys, N. et al., Pain at the Injection Site of Subcutaneously Administered Erythropoietin in Maintenance Hemodialysis Patients: A Comparison of Two Brands of Erythropoietin, Am J Nephrol, (1992), pp. 68–72, vol. 12:68.

* cited by examiner

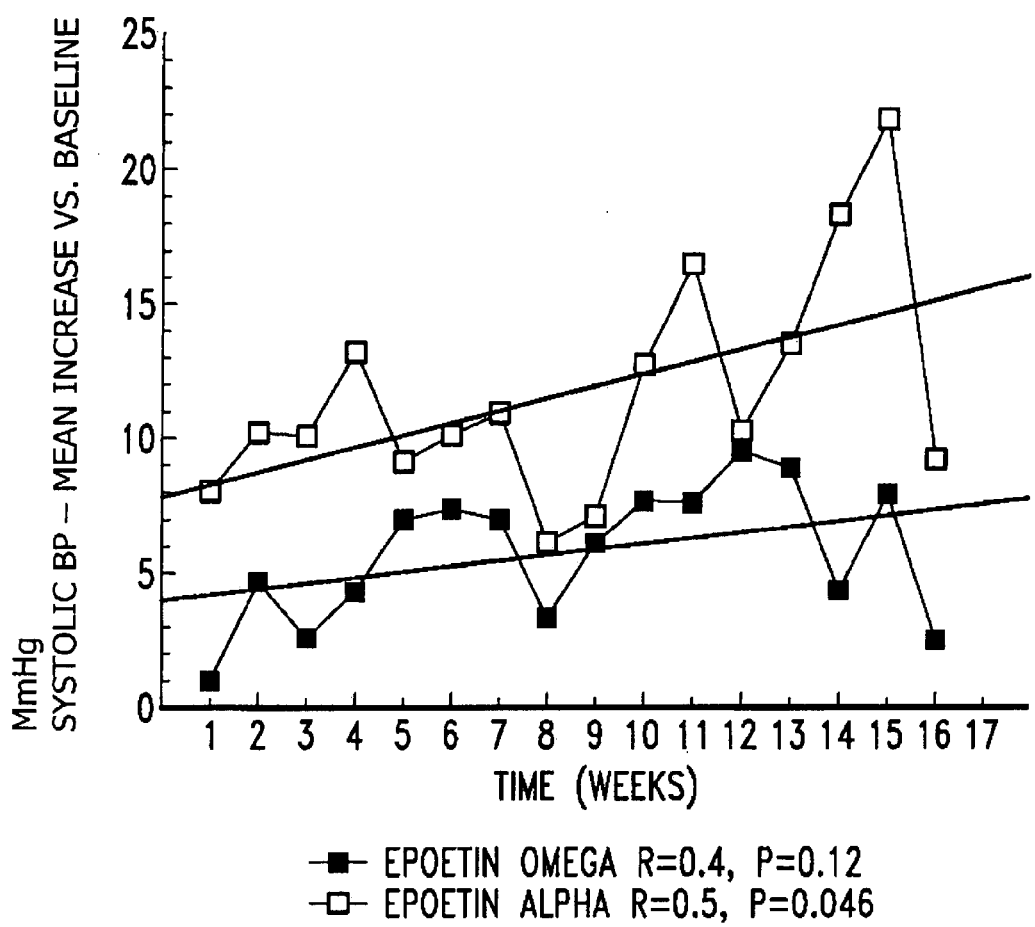

THERAPEUTIC METHODS FOR TREATING SUBJECTS WITH A RECOMBINANT ERYTHROPOIETIN HAVING HIGH ACTIVITY AND REDUCED SIDE EFFECTS

TECHNICAL FIELD

The present invention relates to the field of therapeutic uses for erythropoietin, and more particularly, to treating subjects with a recombinant erythropoietin prepared from an Apa I human genomic DNA fragment, including recombinant erythropoietin expressed in transformed baby hamster kidney cells that produces fewer side effects than other recombinant human erythropoietins including those prepared from Chinese Hamster Ovary cells.

Erythropoietin (EPO) is an important pharmaceutical for use in a variety of therapies where stimulation of red blood cell proliferation (RBC) is desired. Historically the development of the use of recombinant EPO (rHu EPO) has been viewed as strictly an anti anemia factor known to be a growth factor for stimulation of differentiated stem cells in the bone marrow to stimulate the production of reticulocytes (i.e., proliferation of young post-stem cells). Typically, for purposes treating anemia, EPO and was initially hoped to be useful for any condition of anemia where there exists an endogenous hormone deficiency, where blood is lost or where a patient has indications of anemia, or has hyporesponsiveness of the bone marrow to the endogenous hormone. Example conditions potentially thought initially treatable with Erythropoietin include, anemia of malignant disease (i.e., any type of solid cancer, or hematological cancer including leukemia, lymphoma and multiple myeloma); anemia resulting from a chemotherapeutic/radiation treatment of a malignant disease; anemia of chronic disease including for example, autoimmune diseases such as rheumatoid arthritis and hepatitis, anemia in AIDS patients, especially those treated with AZT; anemia of prematurity; anemia associated with renal failure; anemia of thalasemia; autoimmune hemolytic anemia; aplastic anemia; and anemia associated with surgery (e.g., for improving preoperative blood donation for autotransfusion to stimulate an increase in hemoglobin (hemoglobin) levels to counter substantial blood loss, or to increase erythropoiesis in subjects undergoing bone marrow transplantation).

Erythropoietins used for such treatments are glycosylated proteins prepared by expression from recombinant human erythropoietin genomic DNA or cDNA sequences in mammalian cell lines. As described in more detail hereafter, there are at least three forms of recombinant human erythropoietin commonly used in the art, Epoetin Alfa, Epoetin Beta, and Epoetin Omega.

It has recently been established that recombinant erythropoietin preparations differ significantly depending on the precise sequence of DNA used for expression, or the host cell line used, and/or the structural and biological properties of the erythropoietin produced thereby. Different structural and biological properties include such features as differing glycosylation patterns, different isoforms (analyzed by isoelectric focusing (IEF) and RP HPLC analysis), different molecular size/weights, differing antigenic properties, differing pharmokinetic properties, differing dose responses rates, different biological effects, differences in receptor binding and the like.

One type of erythropoietin commonly used in therapy is produced by expression in Chinese hamster ovary (CHO) cells using a large fragment of a genomic clone of the human erythropoietin gene as described for example, in U.S. Pat. Nos. 4,703,008 and 5,955,422 to Lin incorporated herein by reference. This type of erythropoietin includes the epoetins designated Epoetin Alfa (genomic DNA) or Beta (cDNA). Epoetin Alfa is commercially available under the trade names EPREX, PROCRIT or EPOGEN. EPOGEN runs as a single peak by RP HPLC, and has few isoforms by IEF isoform analysis. Epoetin Alfa and Beta have been reported by various techniques to have an average molecular weight estimated in the range of 30.4 to 41 kD. This estimate varies depending upon the report or technique used for the analysis, (see USPDI, under EPOGEN; *J. Chromatog. B* 687:189, 1996; *J. Am. Soc. Nephrol.* 10:2392, 1989. One side-by-side comparison shown herein using SDS polyacrylamide gel electrophoresis analysis with molecular standards, estimates that Epoetin Alfa and Beta have an average molecular weight of about 41 kD, while that of Epoetin Omega is at about 39 kD. Epoetin Beta is available under the trade name RECORMON, and is almost identical to Epoetin Alfa but contains additional minor isoforms in addition to the major isoforms similar to Epoetin Alfa.

One of the most significant biological side effects of Epoetin Alfa or Beta preparations is a routine increase in blood pressure which can lead rapidly to hypertension on initial dosing, and can continue as a continuing complication/adverse event during prolonged maintenance treatment periods. Other adverse effects include seizure, headaches, thrombosis, delay in efficacy, flu-like symptoms, and many patients complain of and report unwanted and undesirable levels of increased pain at the site of injection, including i.v. or s.c. administration, and increased bodily pain associated with Epoetin Alfa treatment. *BMJ* 303:288, 1991; *Am. J. Nephrol.* 12:68, 1992; *Pharm. Week Bl* 13:55, 1992; *Nephrol. Dial. Transplant* 13:817, 1998; *Clin. Nephrol.* 49:41, 1998. In addition, an increase in formation of blood platelets is a routine event in the use of Epoetin Alfa and Beta, which requires blood thinning agents as a routine aspect of therapy, and which may well contribute to an increased risk of clotting, or thrombosis especially in the vascularly impaired patient. Furthermore, as shown in more detail hereafter, certain subjects experience other adverse side effects such as chronic pain or fatigue. Furthermore, others are non-responsive to treatment with Epoetin Alfa or Beta, such that the response is absent (non-responsive) or limited in nature for some disease states or states brought on by chemotherapeutic agents, radiation treatment or other disorders that suppress cell proliferation. Many of the adverse consequences of the use of rHu EPO as to Alfa and Beta are dose dependant, with higher doses reportedly contributing to the onset of more frequent or more severe adverse reactions, with hypertension or increases in blood pressure being one of those.

Unfortunately, some of the adverse side effects of epoetins Alfa or Beta mean that subjects exhibiting conditions such as preexisting hypertension or who are vascularly impaired, are contraindicated for treatment with epoetins Alfa or Beta and must be carefully monitored. Hypertension, may be associated with other conditions such as heart condition, cancer, liver dysfunction or autoimmune diseases such as rheumatoid arthritis, which increases the risk of treating patients having these conditions with Epoetin Alfa or Beta. Even in cases where a patient is not known to have manifested conditions such as vascular restrictions or vascular disease such as artery narrowing, medical professionals would seek to avoid an increase in blood pressure or other adverse events even in the totally or near "normal" patient. Further, a patient may be "normal" in not suffering hypertension (e.g., a blood pressure not above 90) but may "enter" hypertension following the administration of rHu ERYTHROPOIETIN. For example, an increase of 20 points of pressure could take a "normal" patient into a "hypertensive" state. Those patients requiring larger doses of rHu EPO stand a greater risk of adverse event, and some patients in dialysis, or some in oncology associated anemia must take much larger doses as required to obtain the desired increase in RBC proliferation, hematocirti or hemoglobin count. In addition, the potential for adverse side effects generally precludes use of these epoetins for milder or symptomatic purposes such as to relieve fatigue, relieve vascular pain, to legitimately increase physical performance, for example in soldiers, or to improve cognitive function in otherwise healthy subjects, such as the elderly, for which erythropoietin might otherwise be beneficial, but where the risk of adverse side effects might outweigh the benefits. These problems with other epoetins are contributed to, at least in part, the frequency and high doses of epoetins Alfa and Beta typically required to achieve a therapeutic or physiological benefit. Typically, the frequency of dosing with Epoetin Alfa or Beta is three times or more times per week with the typical dose being 200 or more IU/Kg per week (see for Epoetin Alfa, *Drugs* 38:863, 1989; *Drugs* 49:232, 1985; *Drugs* 51:289, 1996; *J. Bone Joint Surg.* 78:-A:62, 1996; *Lancet* 344:367, 1994; *Transfusion* 36:822, 1996; *Nephrol. Dial. Transplant* 2:85, 1999; *Neth. J. Med.* 54:10, 1999; for comparison with Epoetin Beta, see *Clin. Pharmacol. Ther.* 50:702, 1991).

Accordingly, there is a need in the art for treatment methods using an erythropoietin that lacks or reduces the incidents of one or more of the adverse side effects of erythropoietin produced in CHO cells and which would be useful in methods for treating patients having conditions that might be contraindicated for treatment with epoetins Alfa or Beta. In addition, there is a need for treating subjects that are non-responsive or adversely effected by treatment with epoetins Alfa or Beta. Further, there is a need for an erythropoietin that is active in achieving a response in patients who are suppressed in disease states with treatment such as in chemotherapy and radiation, or who are non-responsive, or have inadequate response to other epoetins.

SUMMARY

The present disclosure fulfills this need by providing for treatment of patients with Epoetin Omega as described in U.S. Pat. No. 5,688,697 and U.S. Pat. application Ser. Nos. 08/238,25 now abandoned and 08/466,412 now abandoned incorporated herein by reference. It is commercially available under the trade names Elanex Erythropoietin, EPOMEGA, EPOMAX, HEMAX, REPOTIN, or Hi Potency EPO cytokine related factor (HP-EPO-CRF) available from Elanex Pharmaceuticals, Bothell Wash. This approved and readily available Epoetin Omega is produced in baby hamster kidney cells (e.g., BHK-21 cells) by expression from an Apa I restriction fragment of the human erythropoietin gene. It is shown herein that Epoetin Omega has significantly more potency, higher serum concentration over clearance time (2.5 times Epoetin Alfa) more bioavailability, requires lower doses both in initial treatment (about 75 to about 120 IU/Kg per week) and maintenance (about 20 to about 75 IU/Kg per week), and is effective in subjects non-responsive to treatment with other epoetins. It is further disclosed that Epoetin Omega has effects on patients that are unrelated to hypoxia or anemia or the increase of red blood cells or hemoglobin. In other words, Epoetin Omega has a direct effect on other mechanisms in the body for reasons not yet fully understood, but in ways that have been identified from clinical observations, such as a reduction or elimination of bodily pain, reduction in nausea, increase in vigor or "energy", increase in sense of well being and/or a better "mood", enhancement in liver function in disorders involving liver impairment or damage, and a variety of other noticeable benefits.

Provided herein is the discovery that Epoetin Omega is surprisingly different from epoetins Alfa and Beta in the type and severity of adverse side effects caused by Epoetin Alfa or Beta, which makes it particularly useful for treatment of certain disease states such as oncology/cancer especially in conjunction with chemo or radiation therapy. One of the most important adverse side effects absent from Epoetin Omega but present with the other epoetins is increased blood pressure and concomitant risk of hypertension. This makes Epoetin Omega particularly useful in the treatment of patients with existing hypertension (or at risk of entering a hypertensive or borderline hypertensive state), heart disease, vascular impairment or those at increased risk of thrombotic episodes. In addition, Epoetin Omega is herein disclosed to be more potent than the other epoetins, i.e., to require less of a dose to provide a therapeutic benefit. Epoetin Omega is also disclosed to act without a latency period, i.e., to immediately produce therapeutic benefits without a time lag in contrast to the other epoetins which typically require at least two weeks to show a measurable response in ordinary anemia such as anemia of renal dialysis patients, and four weeks or longer of use before any clinically significant response, if forthcoming, may be anticipated. It is further shown to be more bioavailable than the other epoetins, i.e., to stay in the plasma at a higher level of concentration based on the same dose of epoetins, and to remain effective in a subject for a prolonged period. Further, there is disclosed the lack of formation of antibodies to EPO in patients treated with Epoetin Omega. These novel properties, alone or in combination permit Epoetin Omega to be used at reduced dosing and frequency, and permit its use in treating subjects adversely affected by use of epoetins Alfa or Beta and/or in subjects non-responsive to these other erythropoietins.

In one aspect, there is provided methods of treating or preventing an anemic condition in a subject that include administering a therapeutic amount of Epoetin Omega, wherein the amount is selected to provide a therapeutic benefit within a treatment period without producing or exacerbating an adverse effect selected from the group consisting of increased blood pressure or hypertension. In one embodiment, the blood pressure includes a diastolic or systolic measurement that is not increased by more than 10 mm Hg during the treatment period. In another embodiment, the diastolic or systolic measurement is not increased by more than 1 mm Hg per unit rise in hemoglobin count (g/dl). In still another embodiment, the risk of developing hypertension in a population of subjects treated with the Epoetin Omega is less than 15% over a population of subjects treated with a placebo.

The anemic condition can be any type of anemic condition including but not limited to, renal anemia, anemia of malignant disease, anemia associated with chemotherapy, anemia of chronic disease, anemia in AIDS, anemia of prematurity, anemia of thalasemia, anemia of autoimmune hemolytic disease, or aplastic anemia. In addition, the method is useful for treating or preventing an anemic condition associated with an operative procedure. In one embodiment, the method includes administering Epoetin Omega prior to withdrawing blood to be used in an autotransfusion (known also as autologous blood transfusion). In another embodiment, the method includes administering Epoetin Omega in a preoperative step, while in still another embodiment, Epoetin Omega is administered in a postoperative step. In still another embodiment, the operative procedure is bone marrow transplant.

In another aspect, there is provided a method of treating or preventing an anemic condition in a subject that is non-responsive or adversely effected by treatment with a therapeutic amount of Epoetin Alfa or Beta. The method similarly includes administering a therapeutic amount of Epoetin Omega, wherein the amount of Epoetin Omega is selected to provide a therapeutic benefit within a treatment period. Typically, doses of 50–150 IU/kg may be administered at a frequency of one to three times per week.

In any aspect, the time required for the treatment period varies depending on the type and severity of the anemia or will vary according to a target therapeutic benefit, which includes, but is not limited to, an increase in red blood cell count (RBC), increase in hematocrit score (HCT), increase in hemoglobin count. The typical treatment includes significantly lower doses of Epoetin Omega and/or less frequent dosing to achieve a therapeutic response than is obtainable using Epoetins Alfa or Beta, or which may not be obtainable at all under any reported dosing of other epoetins, such as in chemotherapy/radiation therapy in cancer/oncology patients. It also adds the feature of a quick and measurable response with no latency, so that treating medical professionals may expect a feedback from blood lab findings within a week or less, compared to as long as 2 to 5 weeks with other epoetins. This in turns allows prompt titration of dosing to achieve result in the patient, and the ability to rapidly determine a patient's responsiveness to Epoetin Omega where a rapid or quick turn around response may be indicated. A rapid response is particularly useful for chemotherapy or radiation therapy patient's who are in need of prompt response in order to continue life saving treatment and not be withdrawn from treatment, thus affording the advantage of no need of risk laden blood transfusion. This permits prolonged treatment with chemotherapeutic agents and/or radiation to destroy or inhibit cancer, where otherwise a discontinuation of treatment may allow the cancer to grow or become more chemo therapeutic resistant as a result of withdrawing from, or lowering the dose or frequency of treatment. Further, it allows for a relative immediate improvement in quality of life in a patient who is anemic, and allows the human body to have a healthy blood stance to fight disease, such as cancer, allowing the body to better use its natural system of dealing with both the treatment and with the cancer.

In a related aspect, there is described a betterment in the sense of well being of the treated patient in general, including chemotherapy patients administered Epoetin Omega which betterment in attitude tended to lessen the patient's perceived severity and downside of chemo/radiation therapy. This provides an improved patient mind set for tolerating the chemo/radiation therapy, and a willingness to re enter chemo/radiation therapy again on any return of cancer. A virtually immediate sense of improvement in well being or betterment in attitude permitted at least one patient to pursue a normal life style even while undergoing chemo therapy regardless of a change in hemoglobin or RBC response. In another related aspect, treatment with Epoetin Omega also provides a reduction or elimination of nausea in the case of chemotherapy/radiation patients, even to the point of a patient declining the normal nausea medications typically prescribed for the chemotherapy patient.

In other aspects, there are provided, methods for treating or preventing an anemia associated with several conditions, including a heart condition, or a vascularly impaired patient, liver dysfunction, hepatitis, autoimmune disease, or malignant disease (i.e., cancer). These methods include treating subjects without increasing the risk or magnitude of an adverse side effect, including, but not limited to, increased blood pressure or hypertension. These methods also include treating a subject that is non-responsive, or adversely effected by treatment with Epoetin Alfa or Beta. In the context of treating conditions associated with cancer, the methods are useful in treating anemic conditions caused in whole or in part, by a cancer therapy. These embodiments include anemic conditions caused by or contributed to by chemotherapy or radiation therapy. These methods include administering Epoetin Omega before, during or after the conclusion of the cancer therapy. In another aspect, there is provided method treating a subject with lower doses of Epoetin Omega, such as 12,000 IU per week, or less and/or a dose administered only once per week compared to 100,000 IU to upwards of 200,000 IU per week for Epoetin Alfa which is typically administered two or more times per week. There is also a generally greater risk of adverse reactions incident to the higher dosing of epoetins, as many adverse reactions may be dose related in terms of the absolute dose in IUs of Epoetin administered in a typical treatment regiment.

In another aspect, there is provided, a formulation or kit for treating a subject that includes a therapeutic amount of Epoetin Omega formulated for treating a subject without producing or exacerbating an adverse side effect such as hypertension or increase blood pressure. This aspect includes formulations or kits for treating a subject non-responsive to, or adversely effected by, treatment with Epoetin Alfa or Beta. The formulation or kit may optionally include instructions for administering the therapeutic amount of Epoetin Omega to achieve a therapeutic benefit. The instructions may include adjustments of the therapeutic amount of Epoetin Omega by comparative reference to an amount of Epoetin Alfa or Beta used in other treatments.

Further, there is disclosed the surprising result that Epoetin Omega has a direct and seemingly immediate, and continuing reduction in body pain associated with various conditions including those of oncology, fibromyalgia, chronic fatigue syndrome, RA, hepatitis and including liver impaired/diseased states as well as in the cancer patient undergoing chemotherapy. Even more surprisingly, the reduction in bodily pain occurs regardless of a significant erythropoiesis stimulating response such as an increase in RBC count, hematocrit, or hemoglobin levels. The reduction in pain appears within minutes of dose administration, and may continue for several days.

Also disclosed is an improvement in quality of life, vigor and sense of well being, within less than a week or within one to two weeks, of Epoetin Omega administration to a liver impaired patient suffering with advanced hepatitis nearing a terminal condition. These measurable improvements occurred regardless of an increase in hemoglobin or RBC; count and additionally, there was improvement in various parameters of liver function as measured by typical laboratory tests including sgot and others. The improvement in the sense of well being permitted a bed ridden patient suffering from terminal hepatitis to be able to return to an ordinary lifestyle for a period of nearly two years.

These and other aspects of the advantages of treatment methods using Epoetin Omega as provided herein will be apparent to one of ordinary skill in the art in light of the following detailed description.

DRAWINGS

FIG. 5 illustrates a comparison of Epoetin Omega to Epoetin Alfa on mean systolic BP increase over baseline after s.c. administration (30 per group).

Figure 6A:
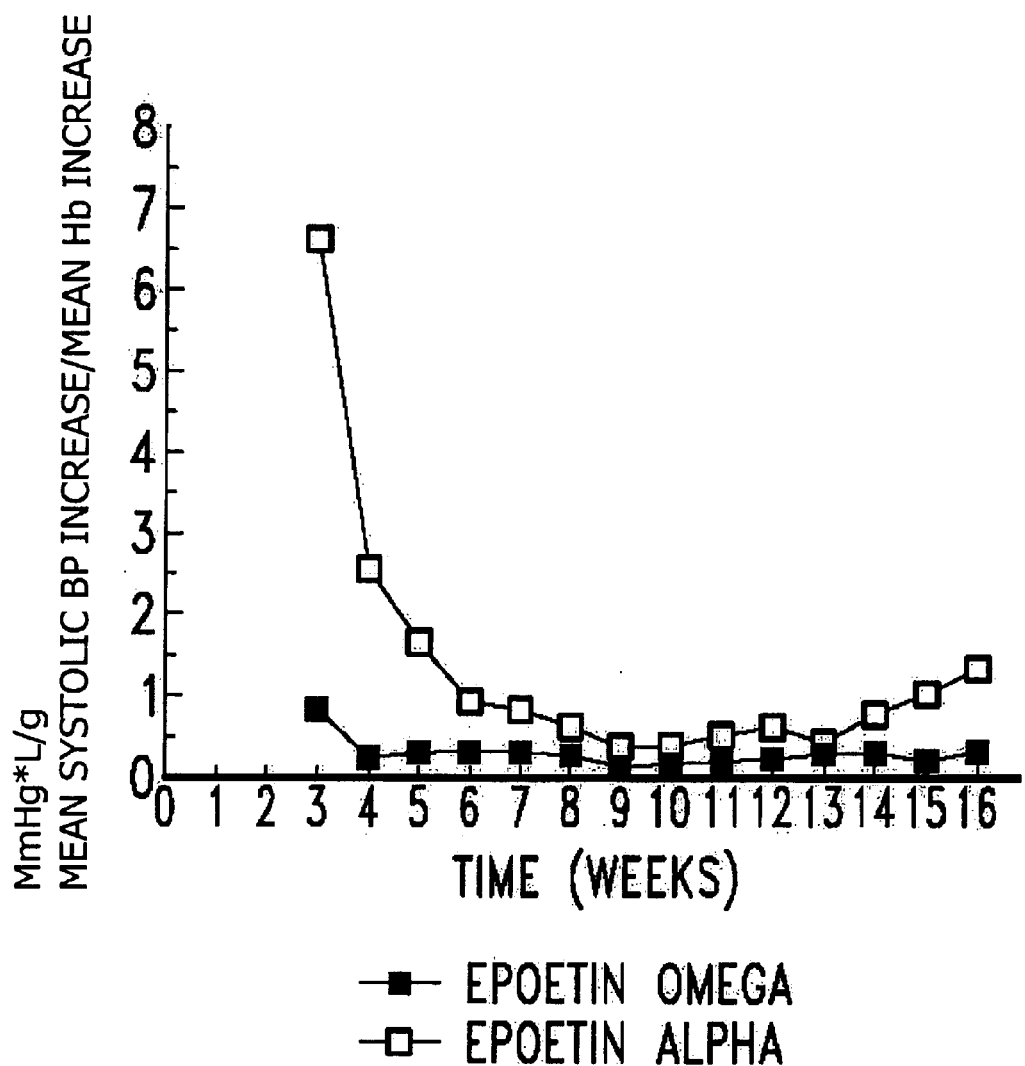
Figure 6B:
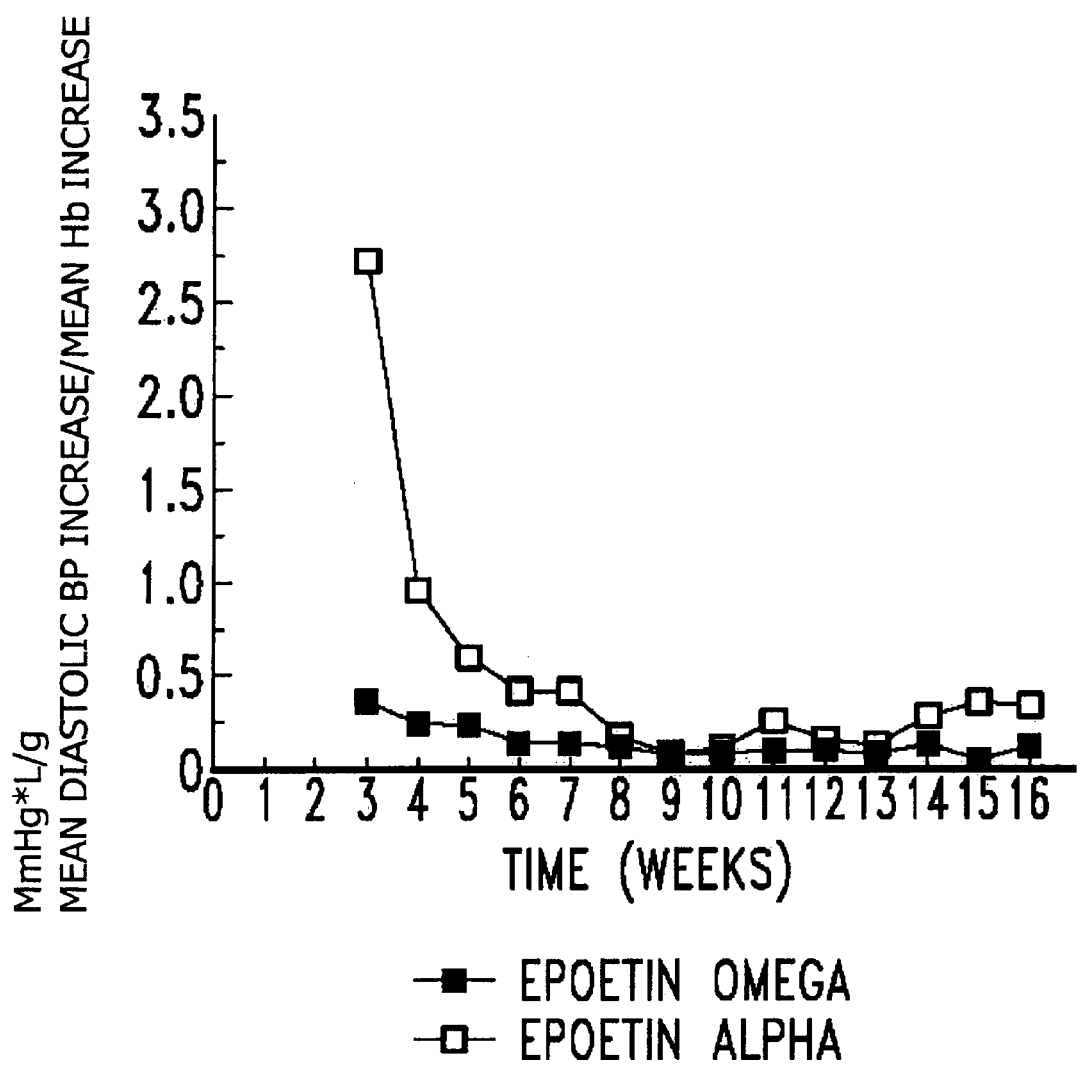

FIG. 6A–D illustrates effects of Epoetin Omega on blood pressure. FIG. 6A shows a comparison of Epoetin Omega to Epoetin Alfa on mean systolic BP (A), and diastolic BP (B) relative to the effect on hemoglobin increase. FIG. 6C shows a slight but linear decrease in both diastolic and systolic blood pressure over a treatment period. FIG. 6D shows hemoglobin increase over a treatment period, a decrease in dose of Epoetin Omega over the treatment period and a decrease in arterial blood pressure decreases during the same period.

Figure 7:
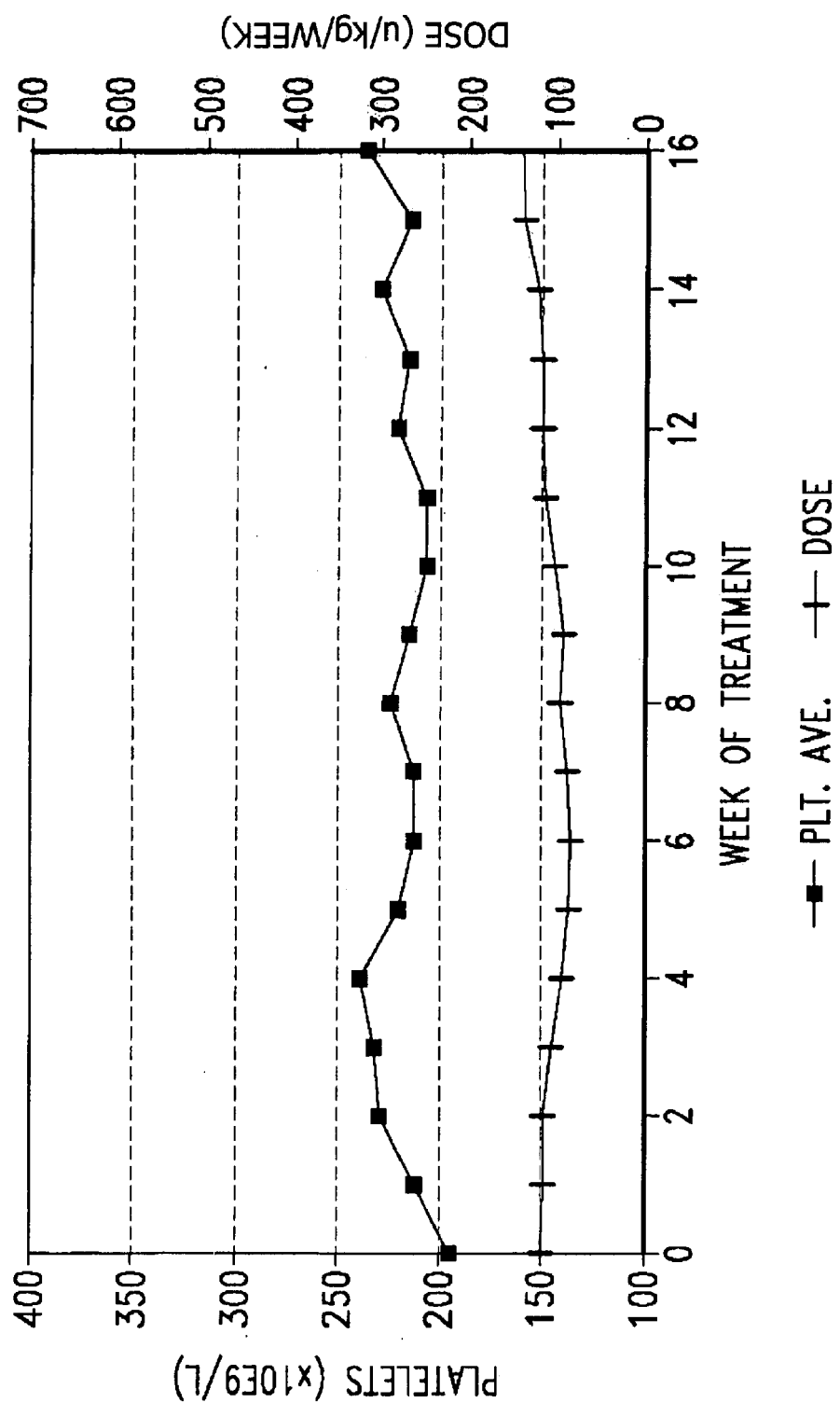

FIG. 7 shows an absence of significant increase in platelets in subjects treated with Epoetin Omega.

Figure 8:
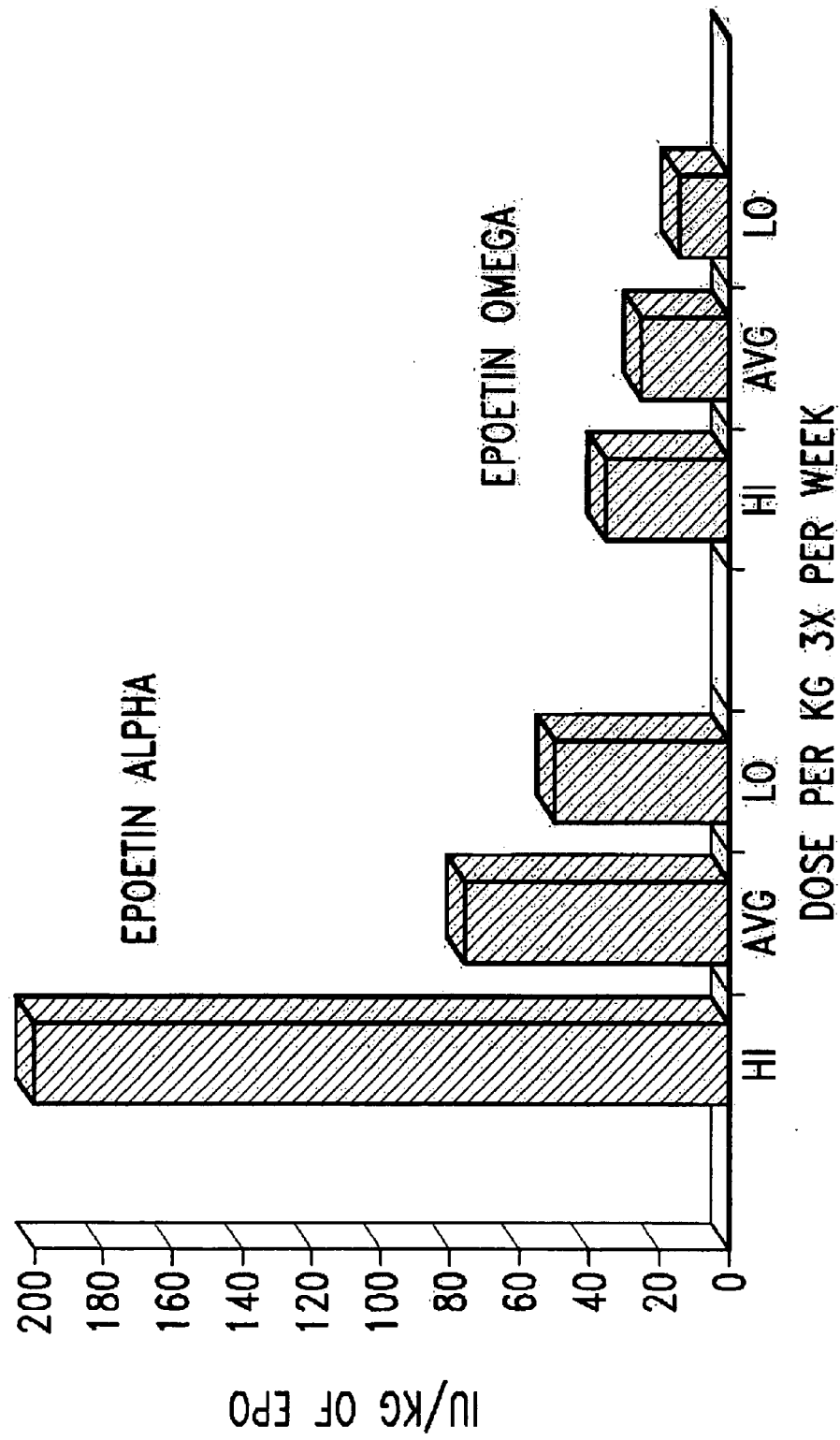

FIG. 8 illustrates differences in maintenance dose requirements for treating an anemia with Epoetin Omega in comparison to patients treated with Epoetin Alfa.

Figure 9A:
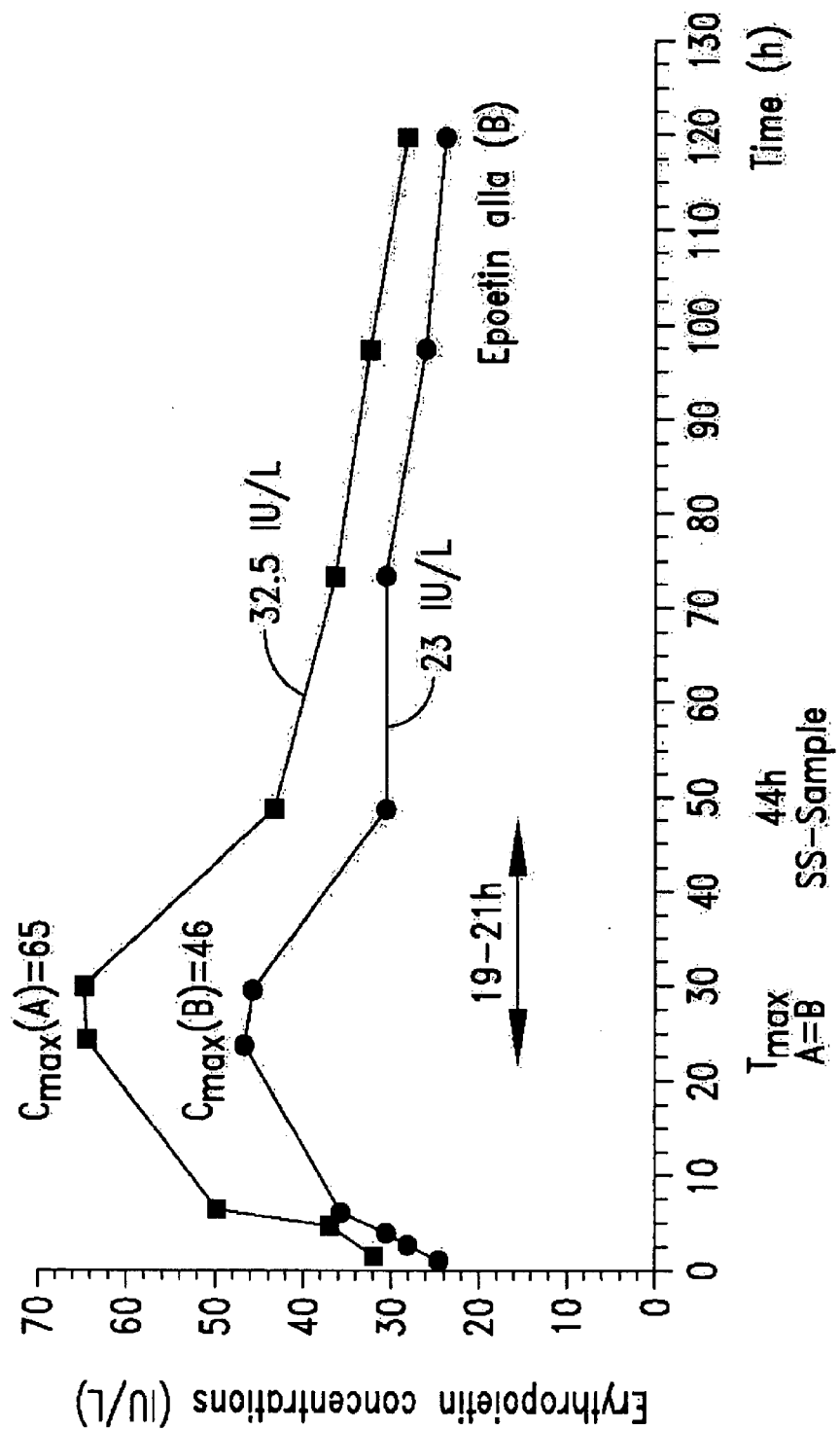
Figure 9B:
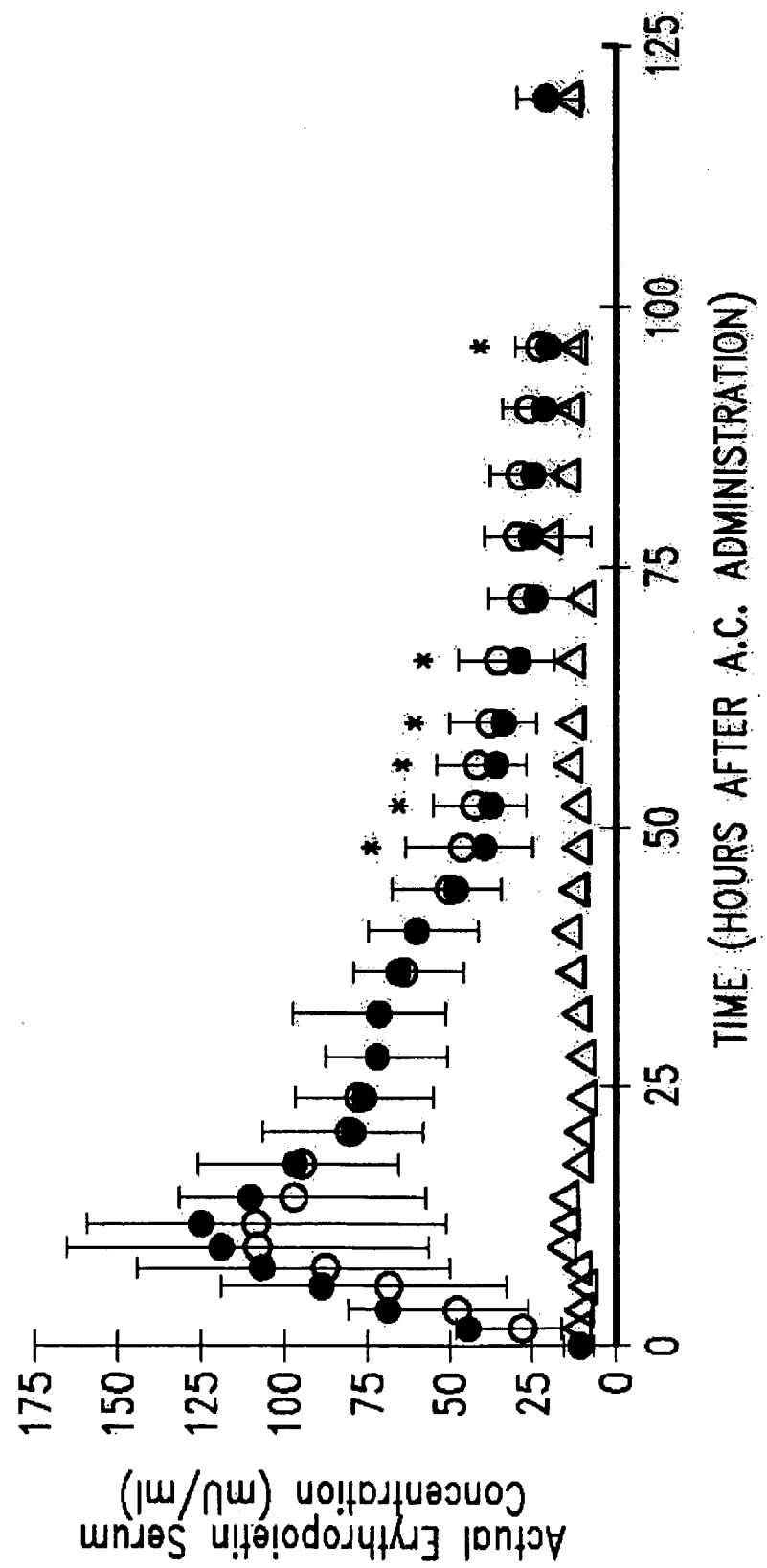

FIG. 9A–B illustrates the mean plasma erythropoietin concentration-time for 18 subjects given a single s.c. dose of 50 IU/kg, of Epoetin Omega in comparison to Epoetin Alfa. FIG. 9A shows comparative serum concentrations of rHu EPO, comparing Epoetin Omega (upper line) to Epoetin Alfa (lower line), illustrating that over time, the serum concentrations in patients in vivo is 2.5 times more by area for Epoetin Omega over Epoetin Alfa. FIG. 9B shows comparative serum concentrations of rHu EPO Alfa and Beta, illustrating that the serum levels of Alfa and Beta are almost identical.

Figure 10A:
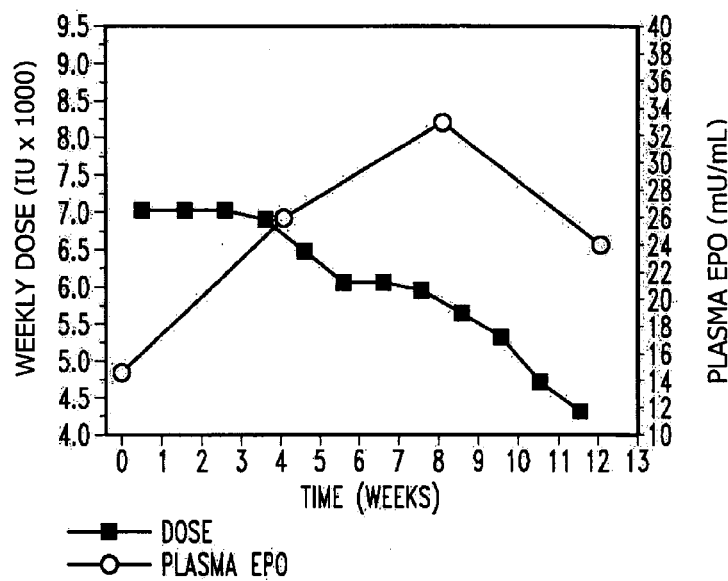
Figure 10B:
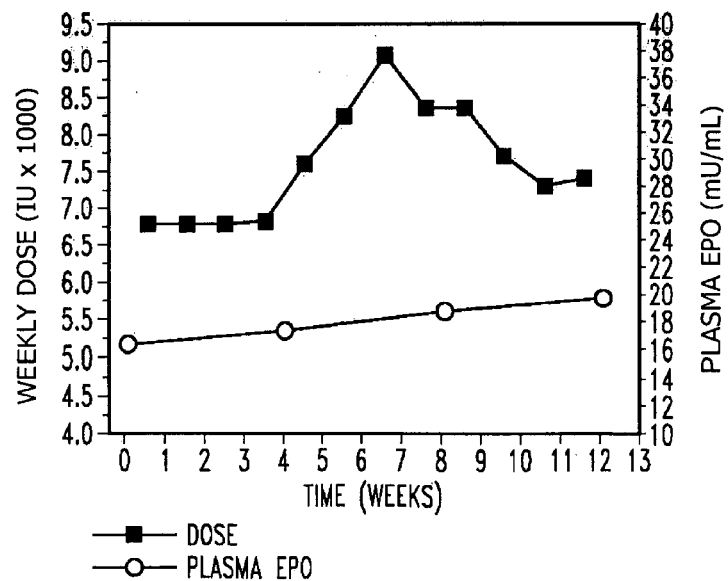

FIG. 10A–B illustrates absolute weekly doses and mean plasma erythropoietin concentrations in patients treated with Epoetin Omega (A), or Epoetin Alfa (B).

Figure 11:
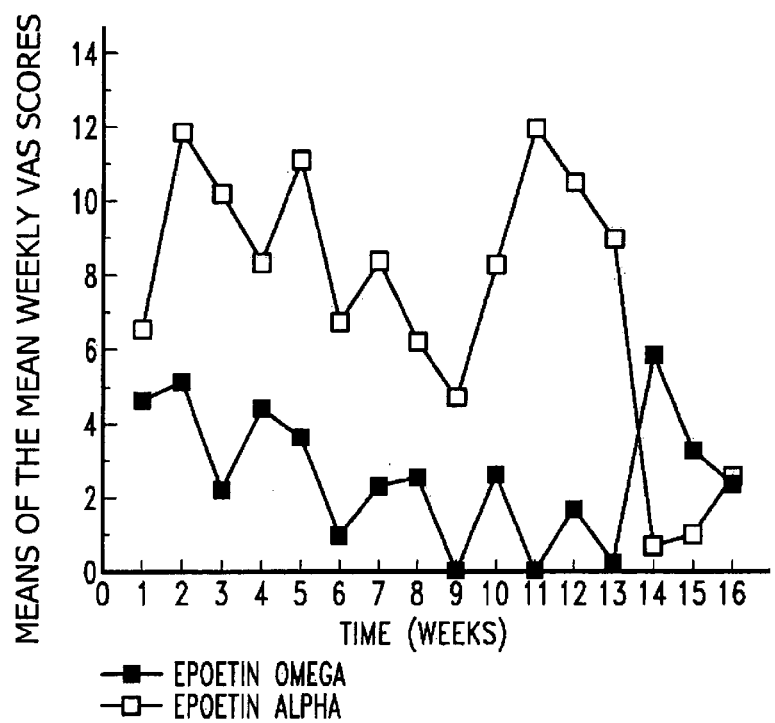

FIG. 11 illustrates a comparison on the pain experienced by patients treated by s.c. injection of Epoetin Omega or Epoetin Alfa. Pain is expressed as the mean weekly Visual Analogue Scale scores for pain at the injection site. (30 per group).

Figure 12:
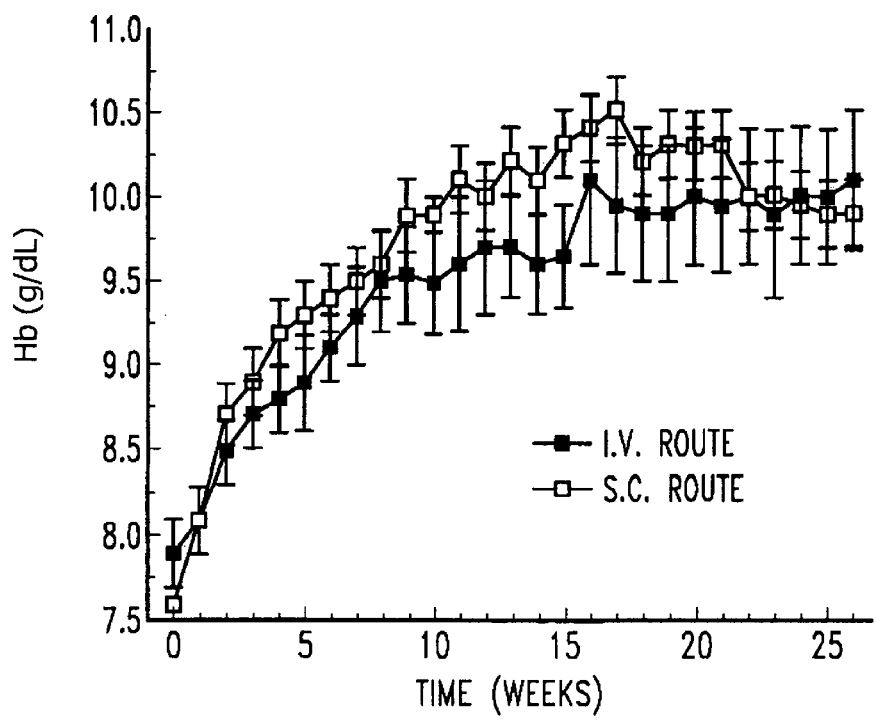

FIG. 12 illustrates rapid response in obtaining an increase in hemoglobin levels shown as the mean of 379 patients that were administered Epoetin Omega by i.v. injection or the mean of 450 that were dosed by s.c. injection. Error bars represent SEM.

Figure 13A:
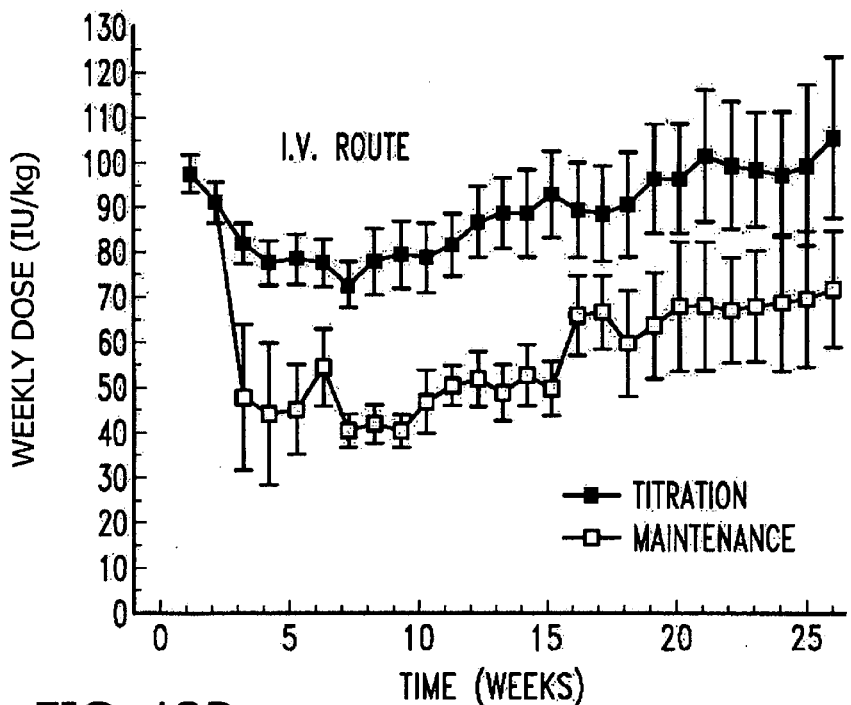
Figure 13B:
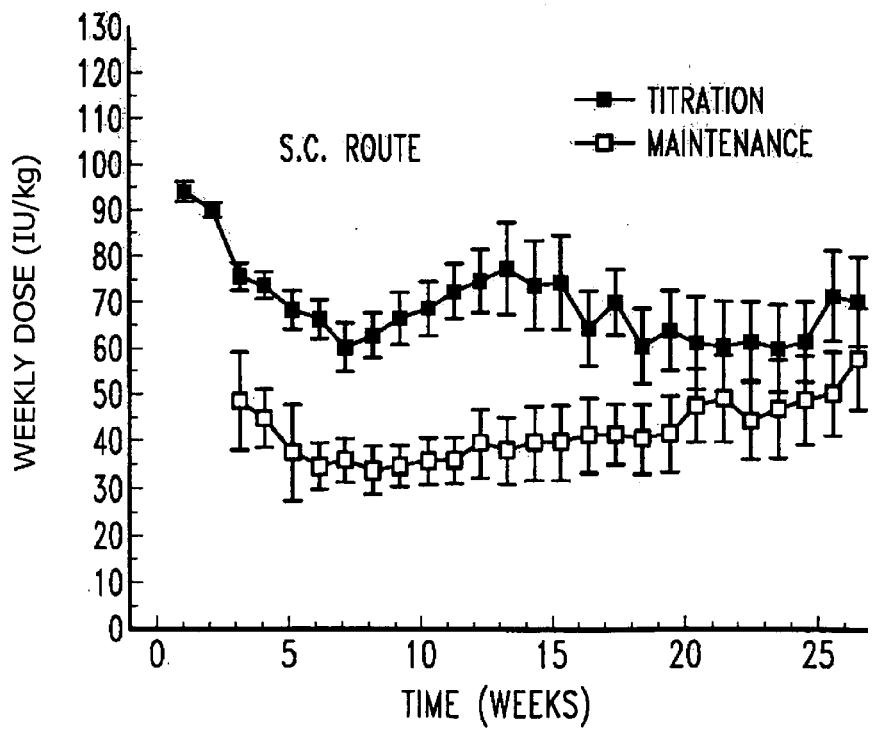

FIG. 13A–B illustrates the mean weekly titration and maintenance doses for patients administered Epoetin Omega by i.v. injection (A), or s.c. injection (B).

Figure 14A:
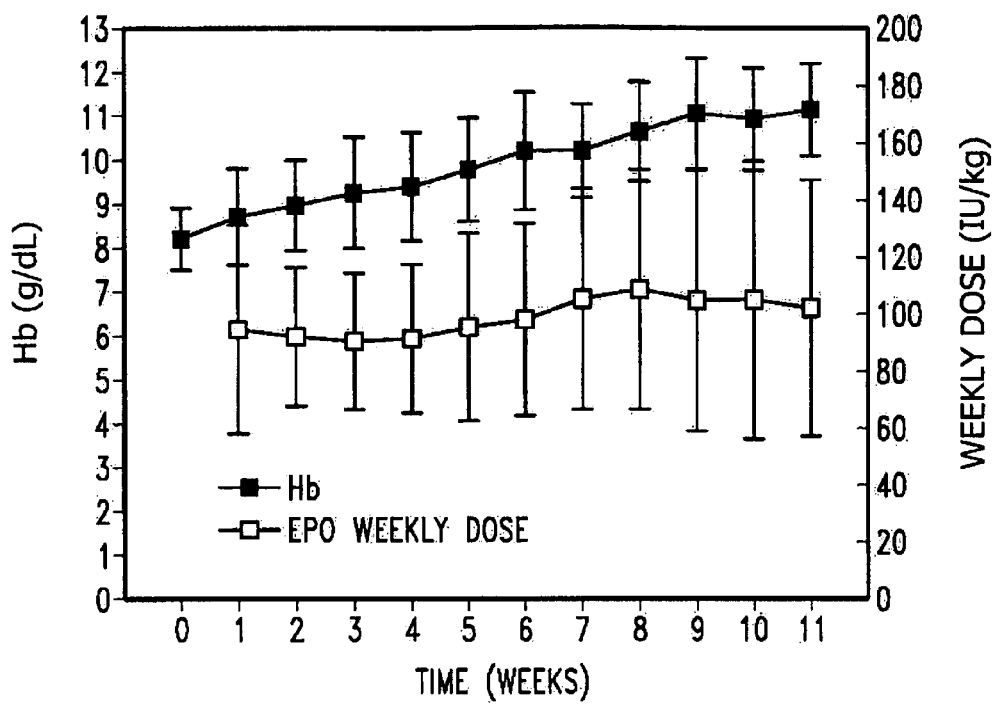
Figure 14B:
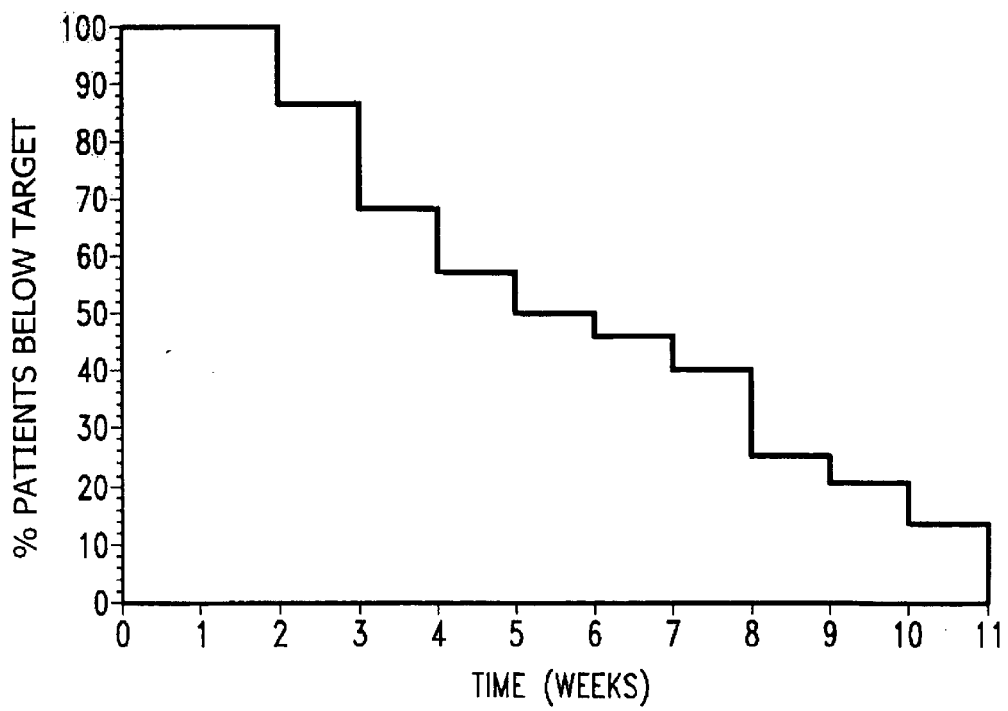

FIG. 14 shows results from a clinical trial illustrating that mean hemoglobin values continuously increase over 11 weeks of Epoetin Omega treatment.

Figure 15A:
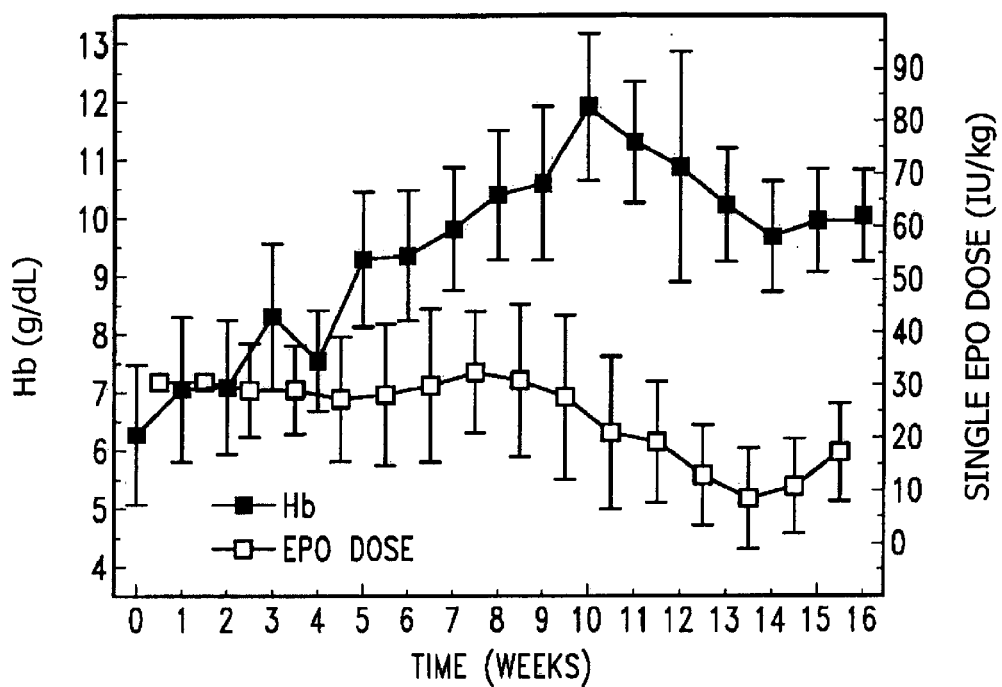
Figure 15B:
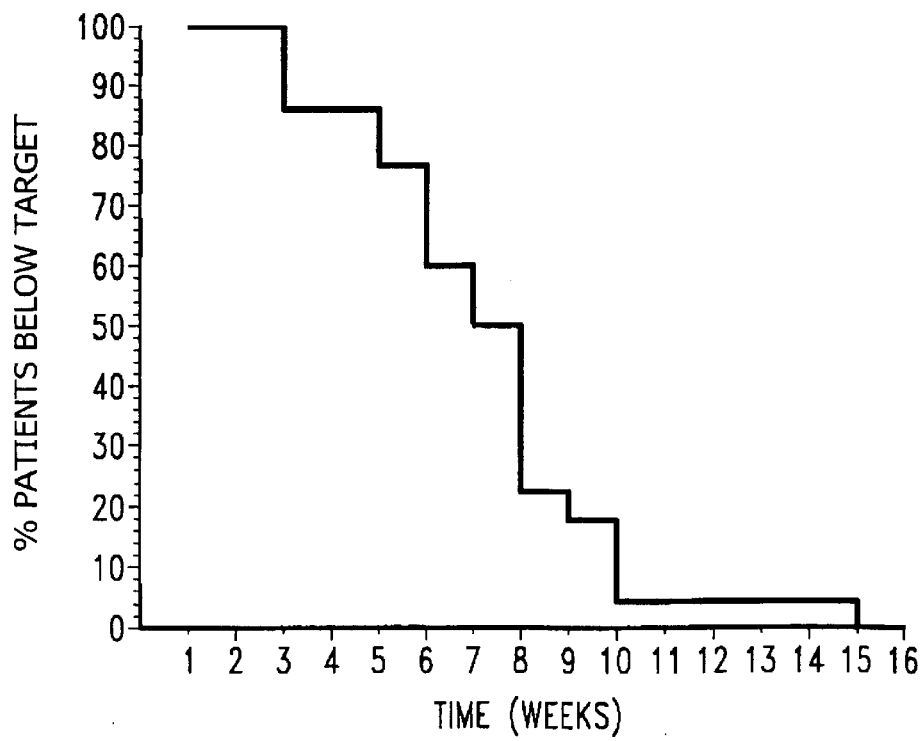
Figure 15C:
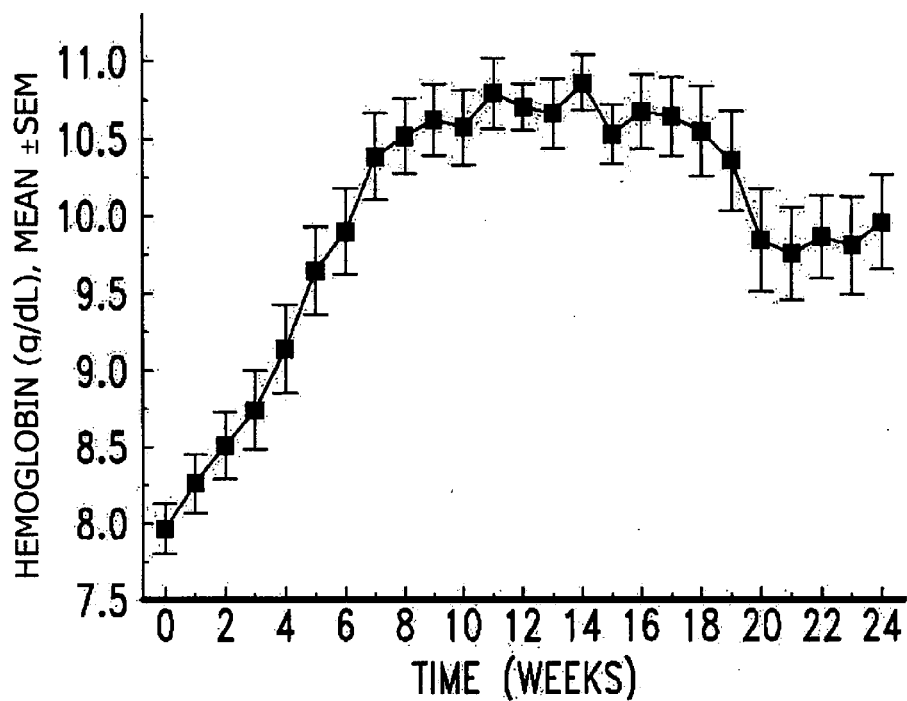
Figure 15D:
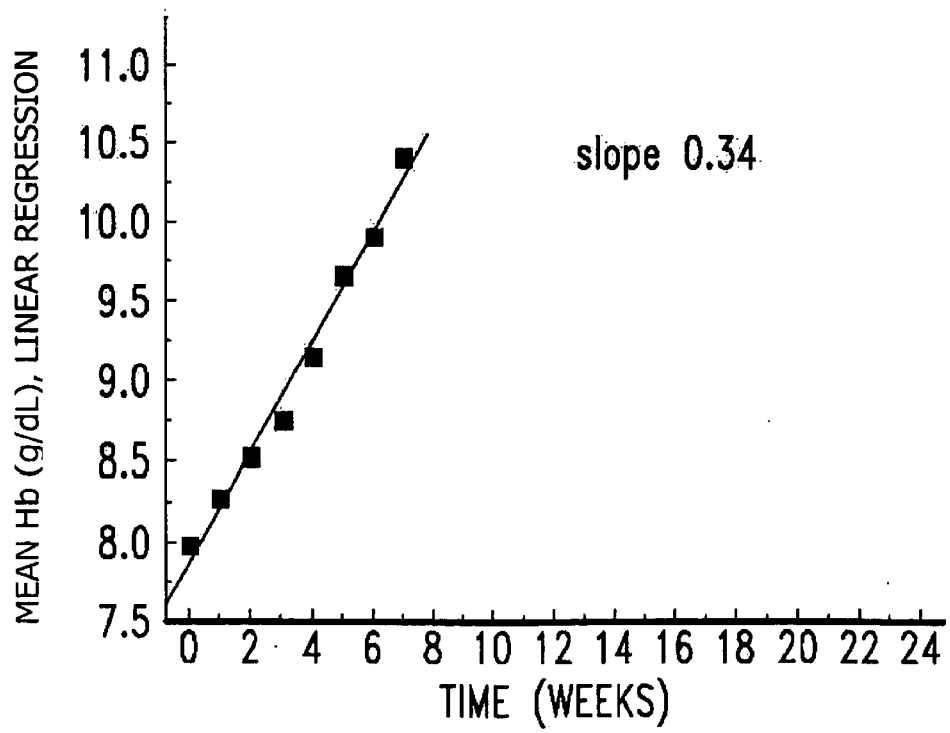
Figure 15E:
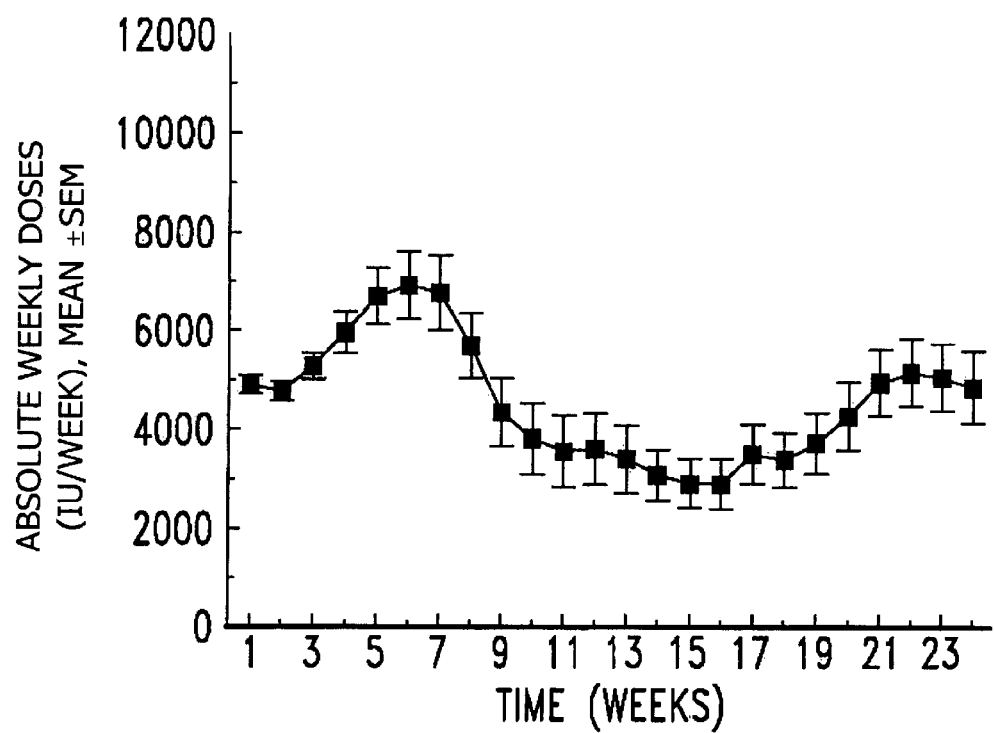

FIG. 15A–C illustrates a rapid response in obtaining an increase in hemoglobin levels using a single weekly dose of Epoetin (A), and percentage of subjects reaching a target hemoglobin level over time (B). FIG. 15C illustrates a rapid and linear increase in hemoglobin for the first 7 weeks of a treatment period of 24 weeks in a population of patients given an average dose of about 3×25 to about 3×33 IU/kg/week and shows a gradual decrease in the total mean weekly does required over the treatment period.

Figure 16A:
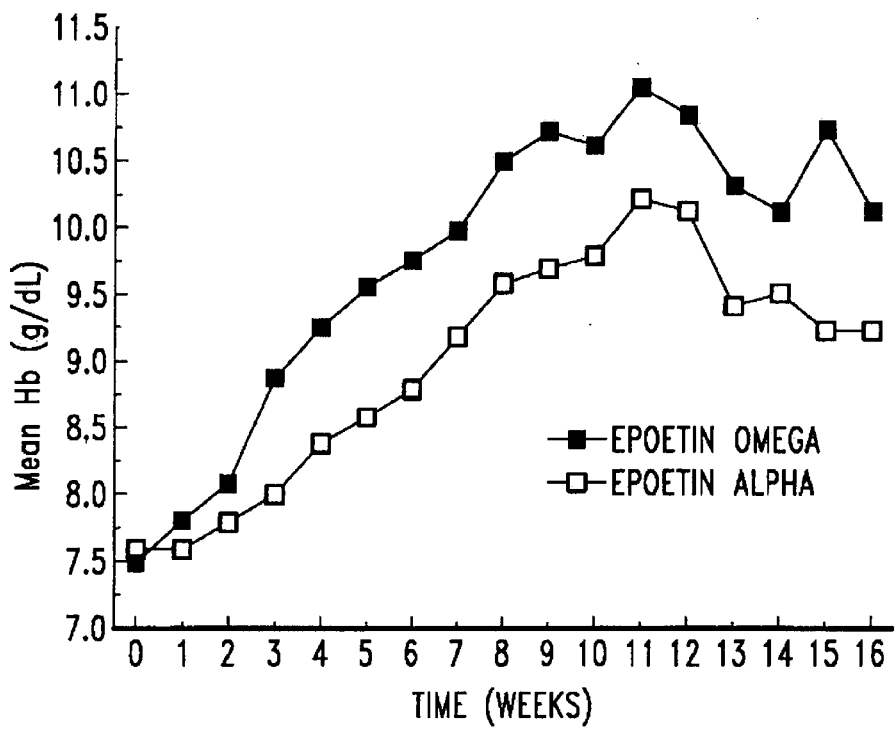
Figure 16B:
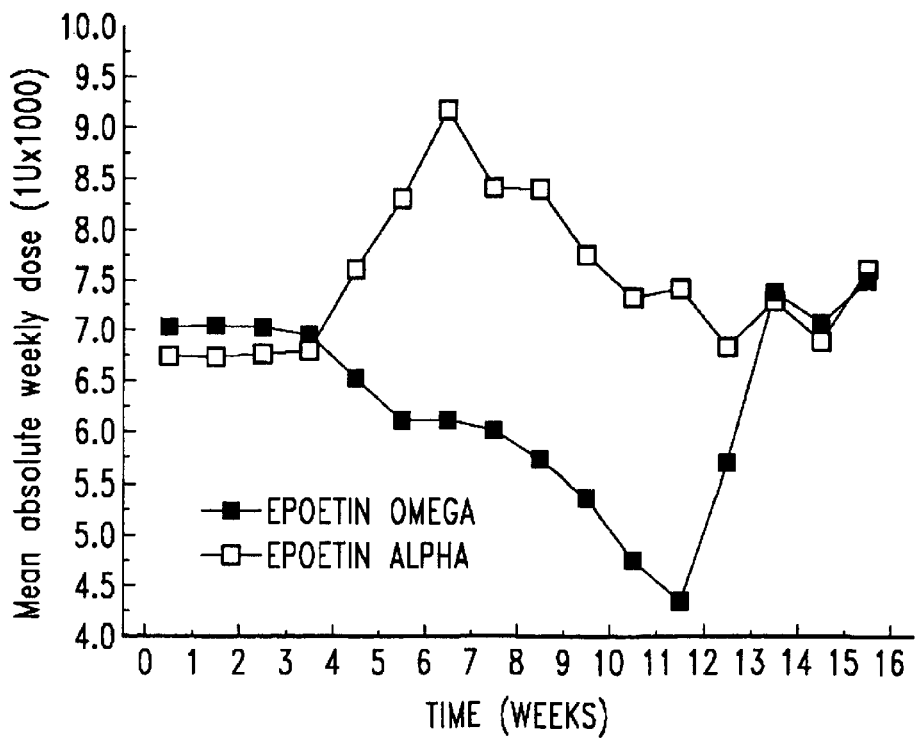

FIG. 16A–B illustrates a comparison of hemoglobin response levels in patients treated with Epoetin Omega or Epoetin Alfa by s.c. injection (30 per group) showing mean hemoglobin values (A) and mean absolute weekly dose required for maintenance (B).

Figure 17A:
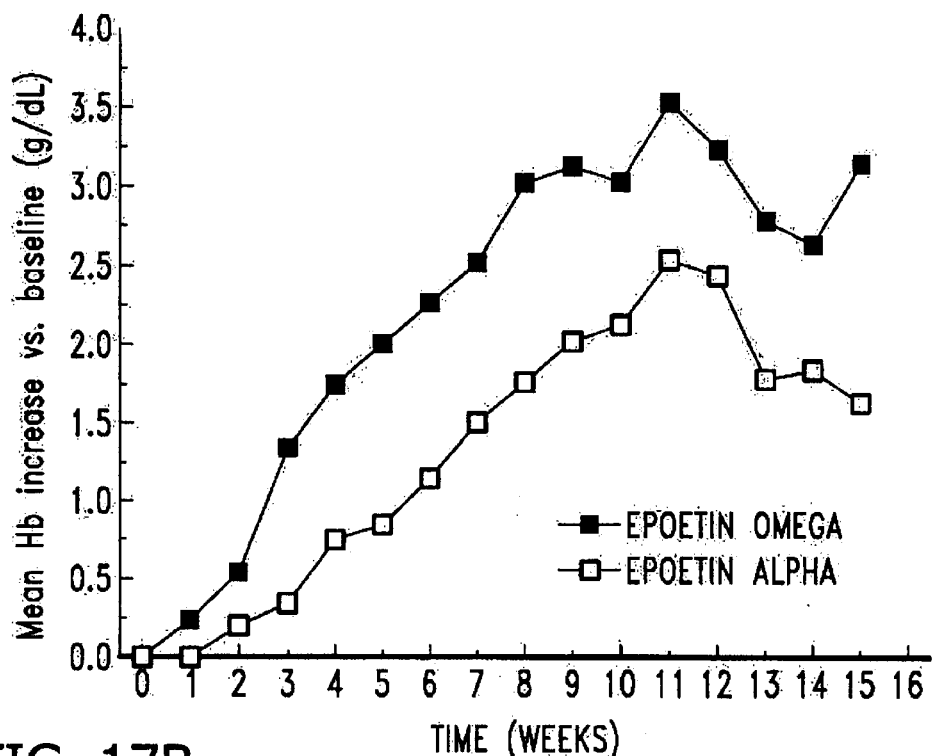
Figure 17B:
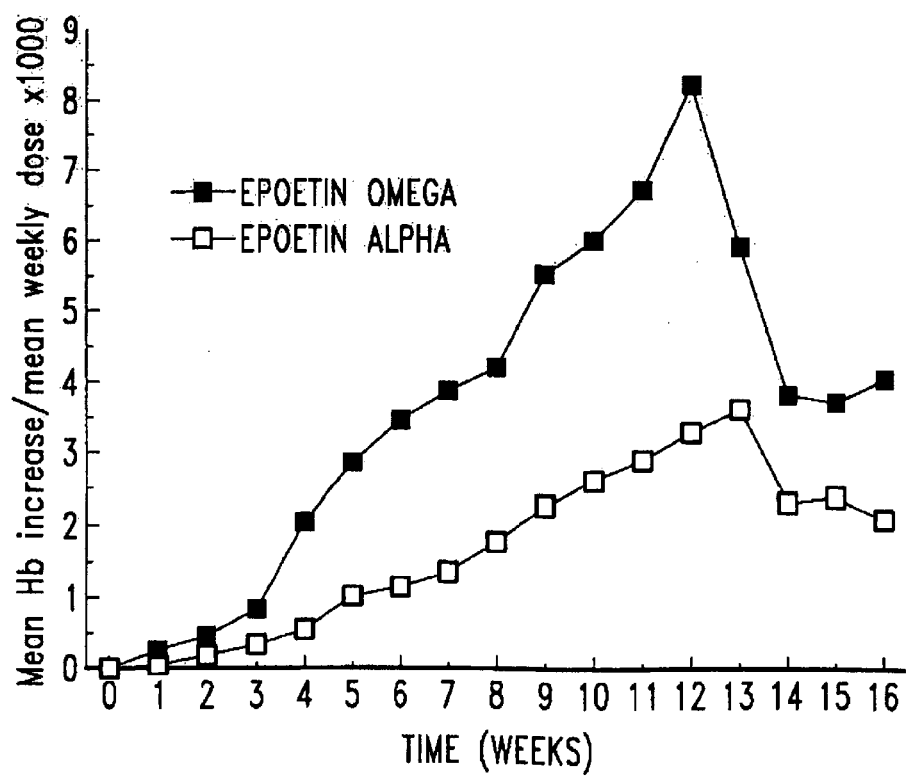

FIG. 17A–B illustrates a comparison of hemoglobin response levels in Epoetin Omega or Epoetin Alfa treated patients as a function of hemoglobin baseline (A), and the ratio of mean hemoglobin increase/mean weekly dose (B).

Figure 18A:
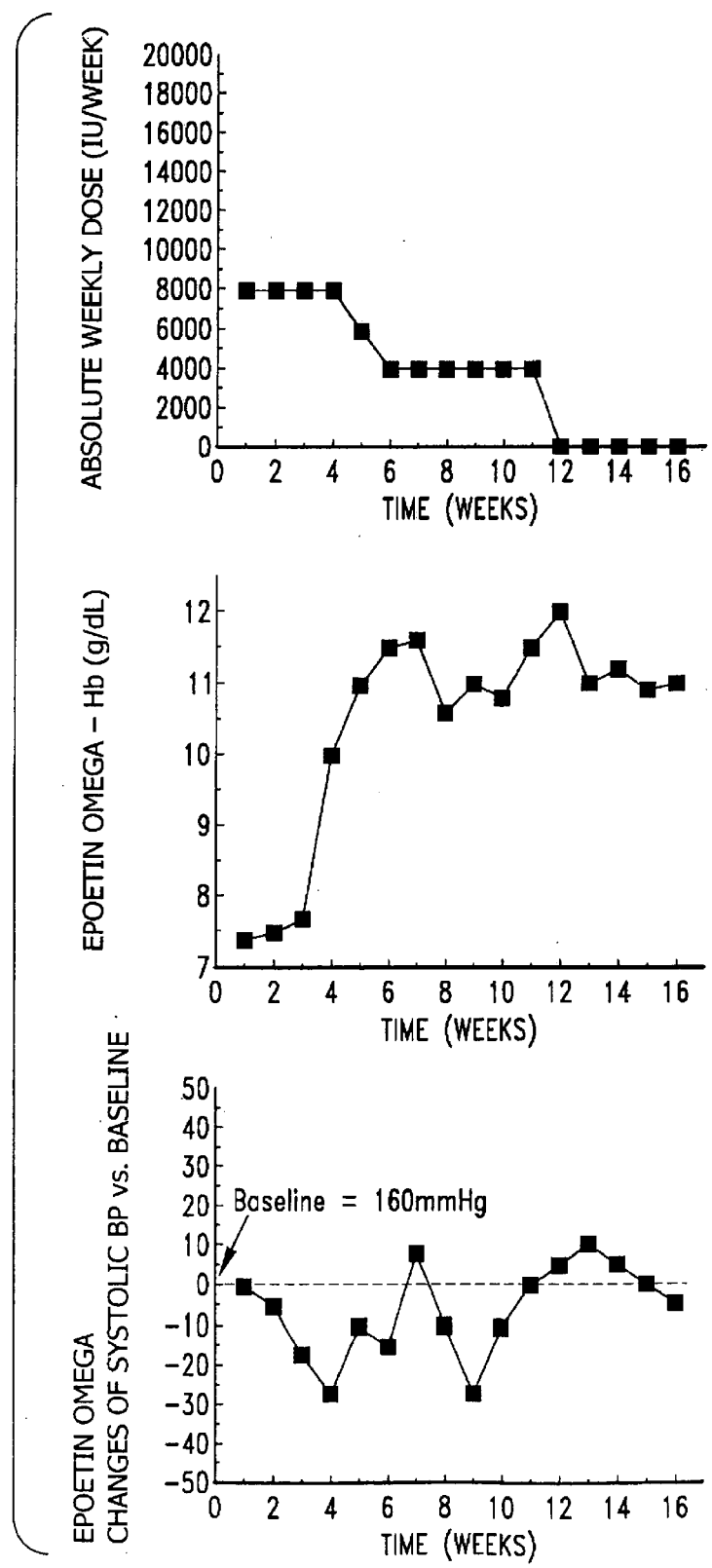
Figure 18B:
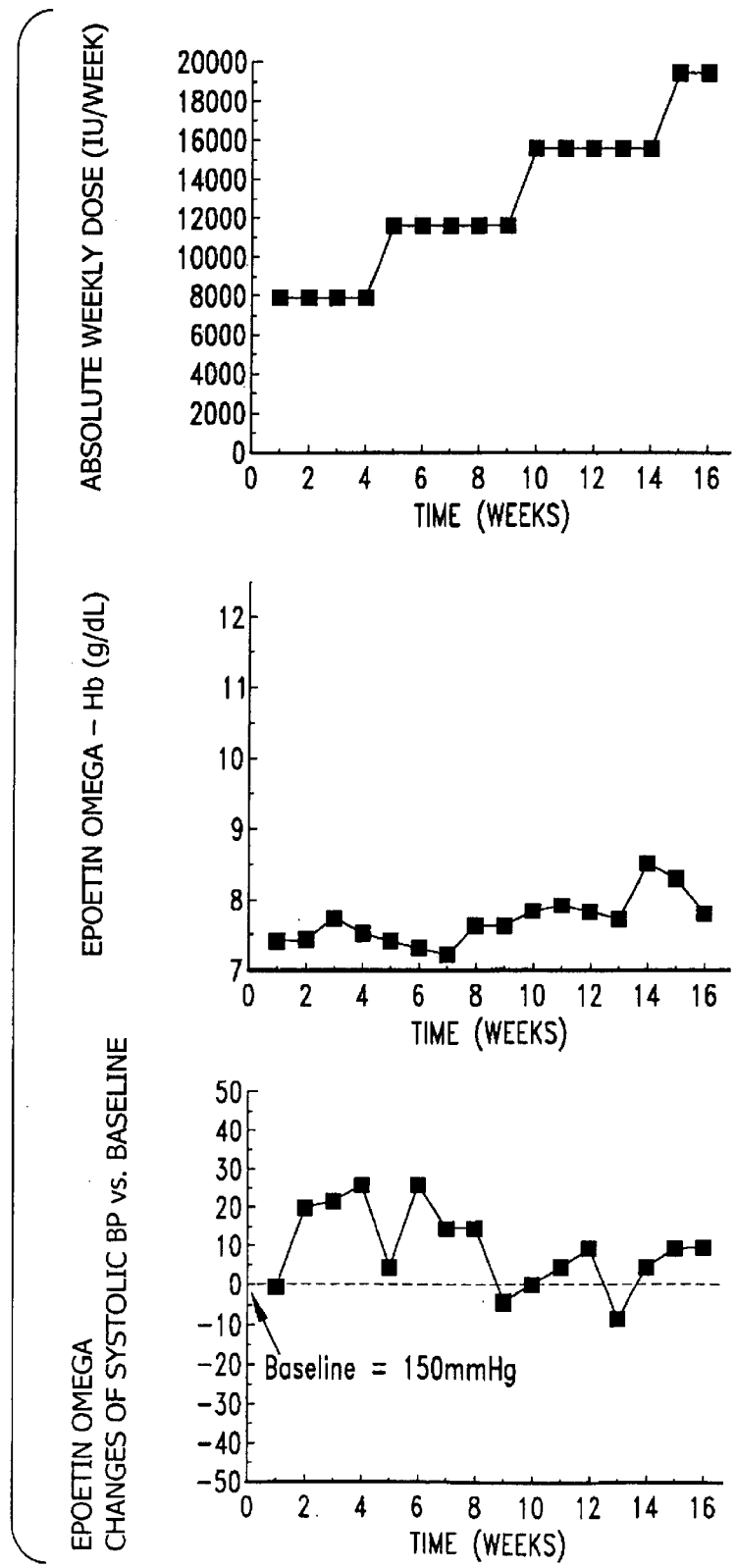
Figure 18C:
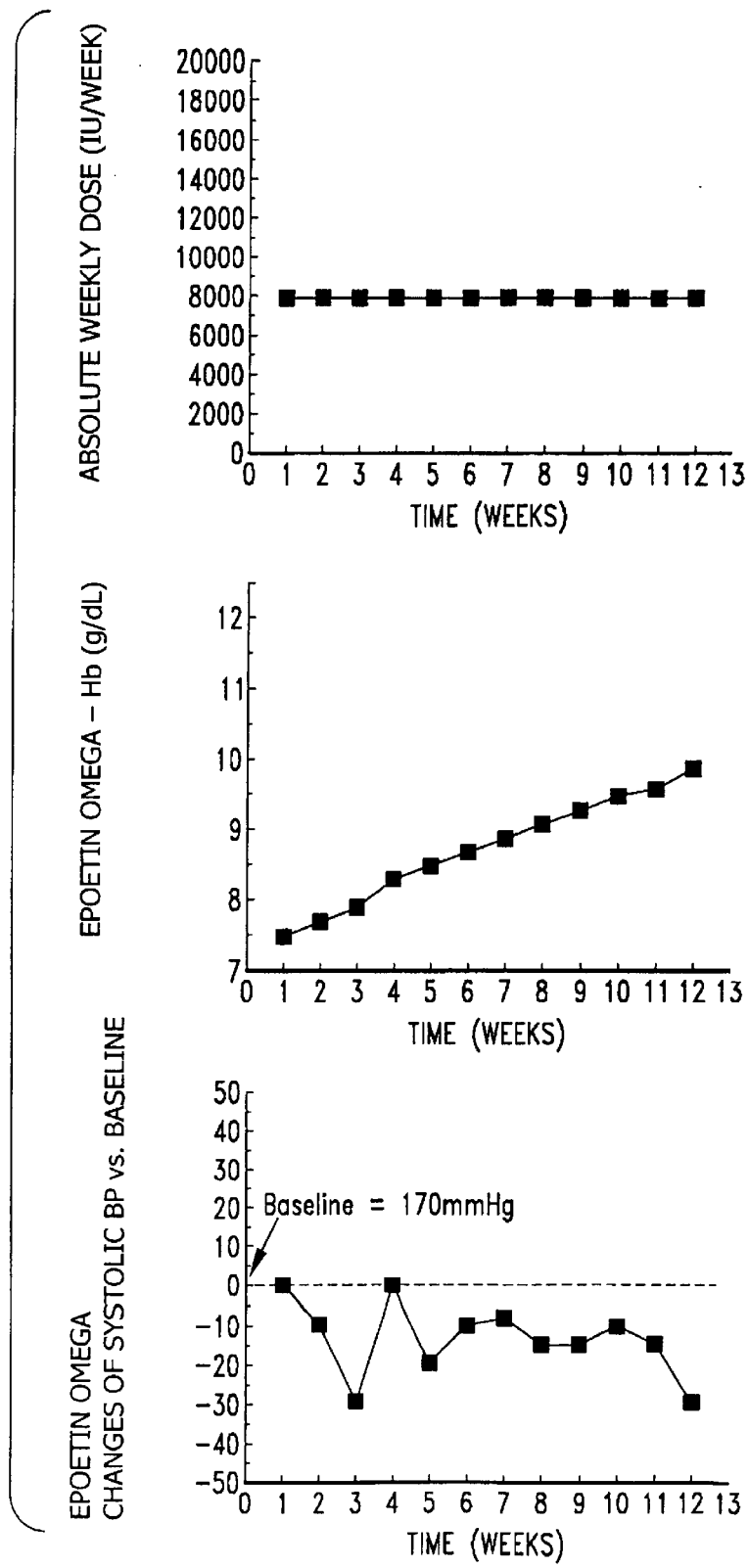

FIG. 18A–C illustrates results from a triple cross-over trial, showing that a subject non-responsive to Epoetin Alfa is highly responsive to Epoetin Omega. 18A shows an initial positive response to Epoetin Omega administered twice per week in a first phase; 18B shows non-response to Epoetin Alfa administered twice per week in a second phase; 18C shows response to Epoetin Omega administered once per week in a third phase. Top panels show total weekly doses, middle panels show hemoglobin count, and lower panels show effects on blood pressure.

FIG. 19A–D illustrates use of Epoetin Omega in a pre-operative procedure to prevent anemia in blood donation. A and B show hemoglobin levels for individuals in a treatment and control group, respectively. C and D show average linear rates of hemoglobin decline until final discharge, and up to the point of surgery, respectively.

Figure 20A:
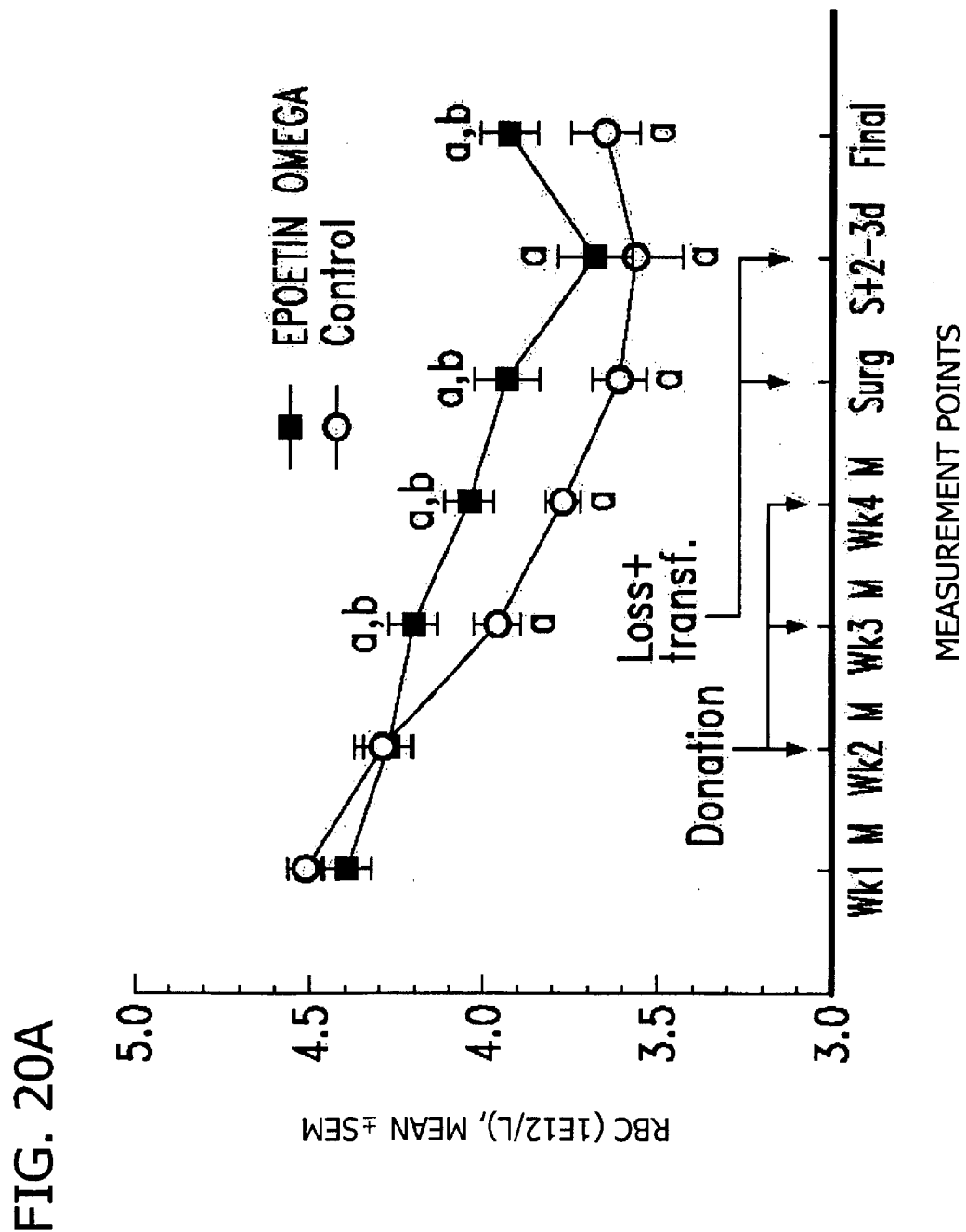
Figure 20B:
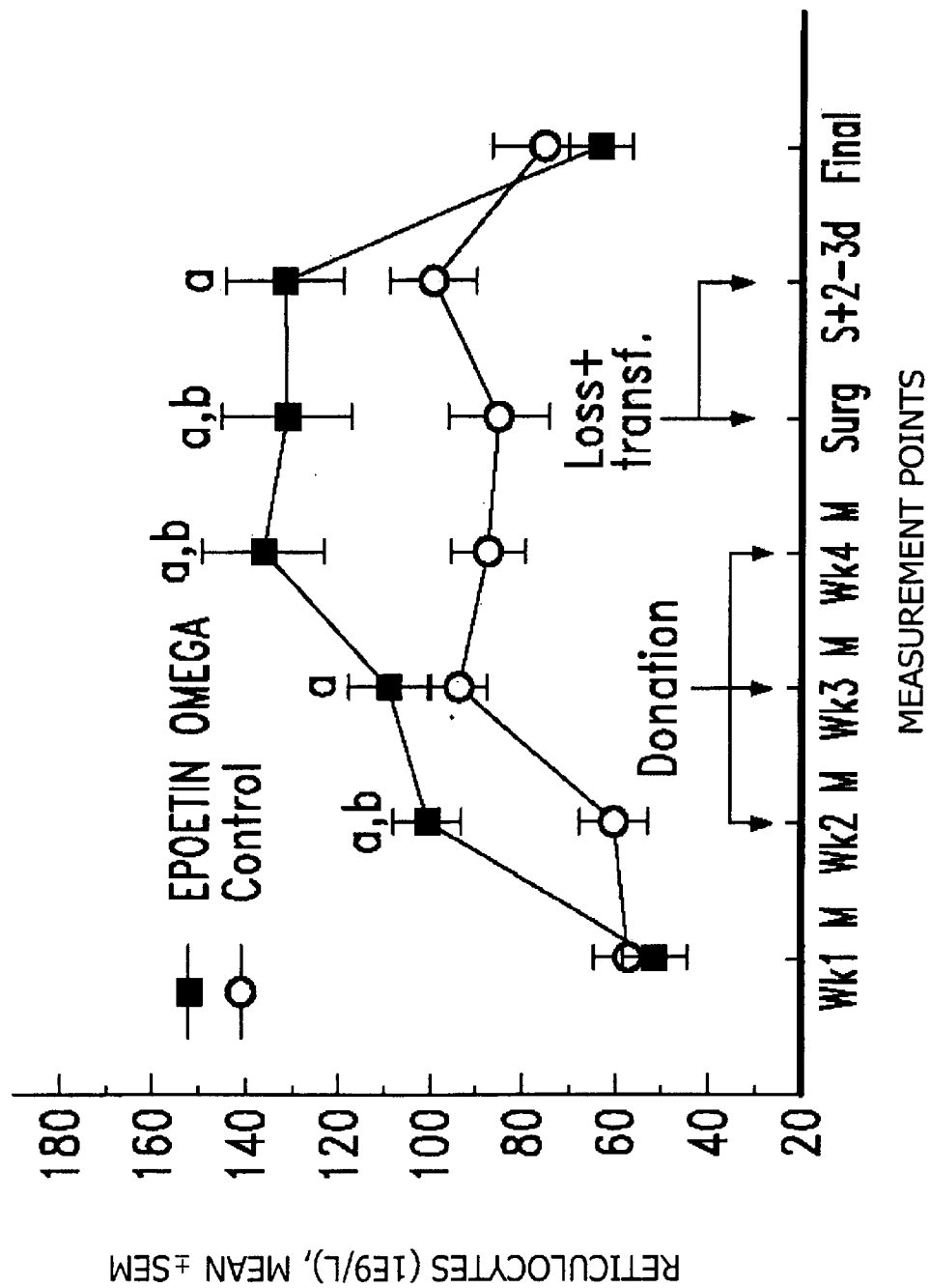
Figure 20C:
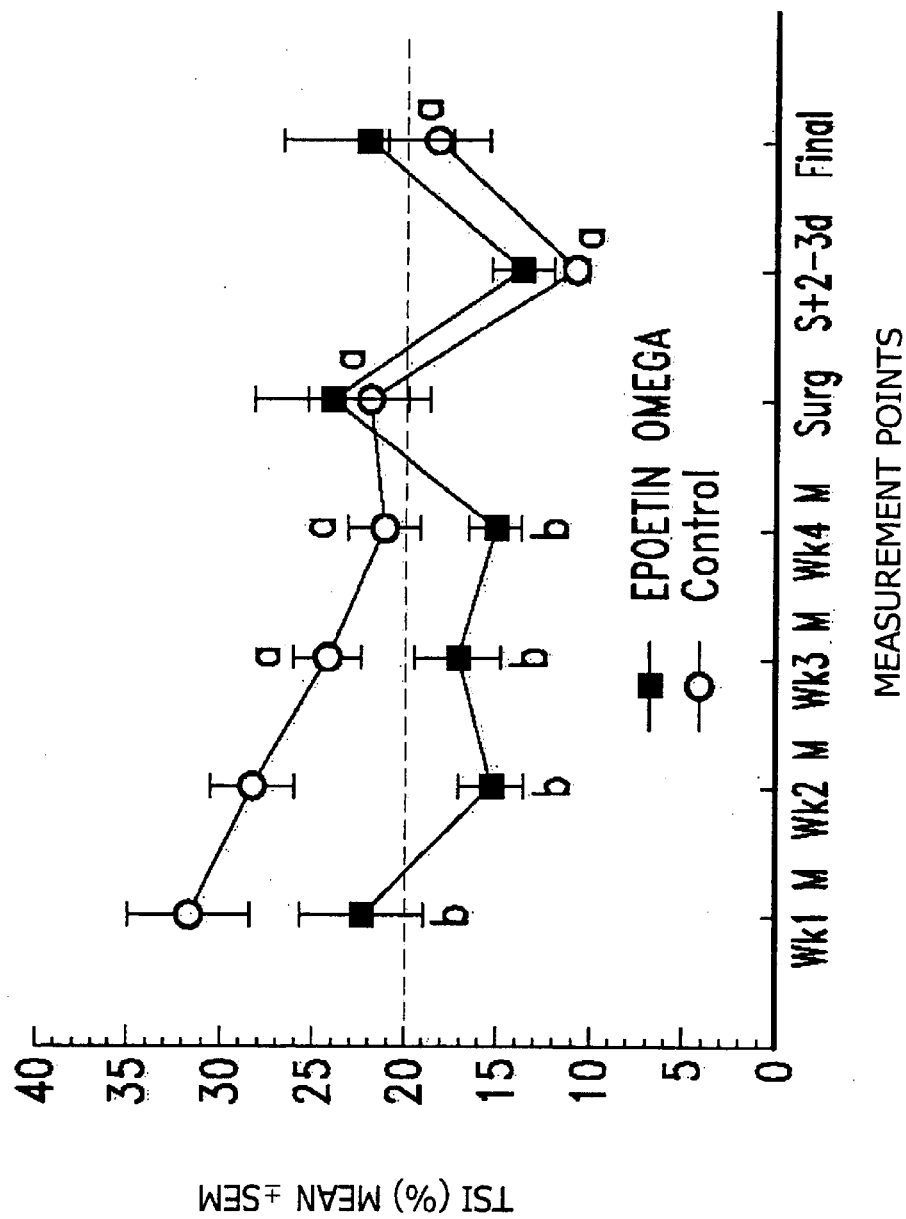

FIG. 20A–C illustrate an average RBC and reticulocyte count, respectively, for Epoetin Omega treated and control patients donating blood in a preoperative procedure. C shows an average total serum iron level (TSI) for treated and control patients until final discharge.

Figure 21A:
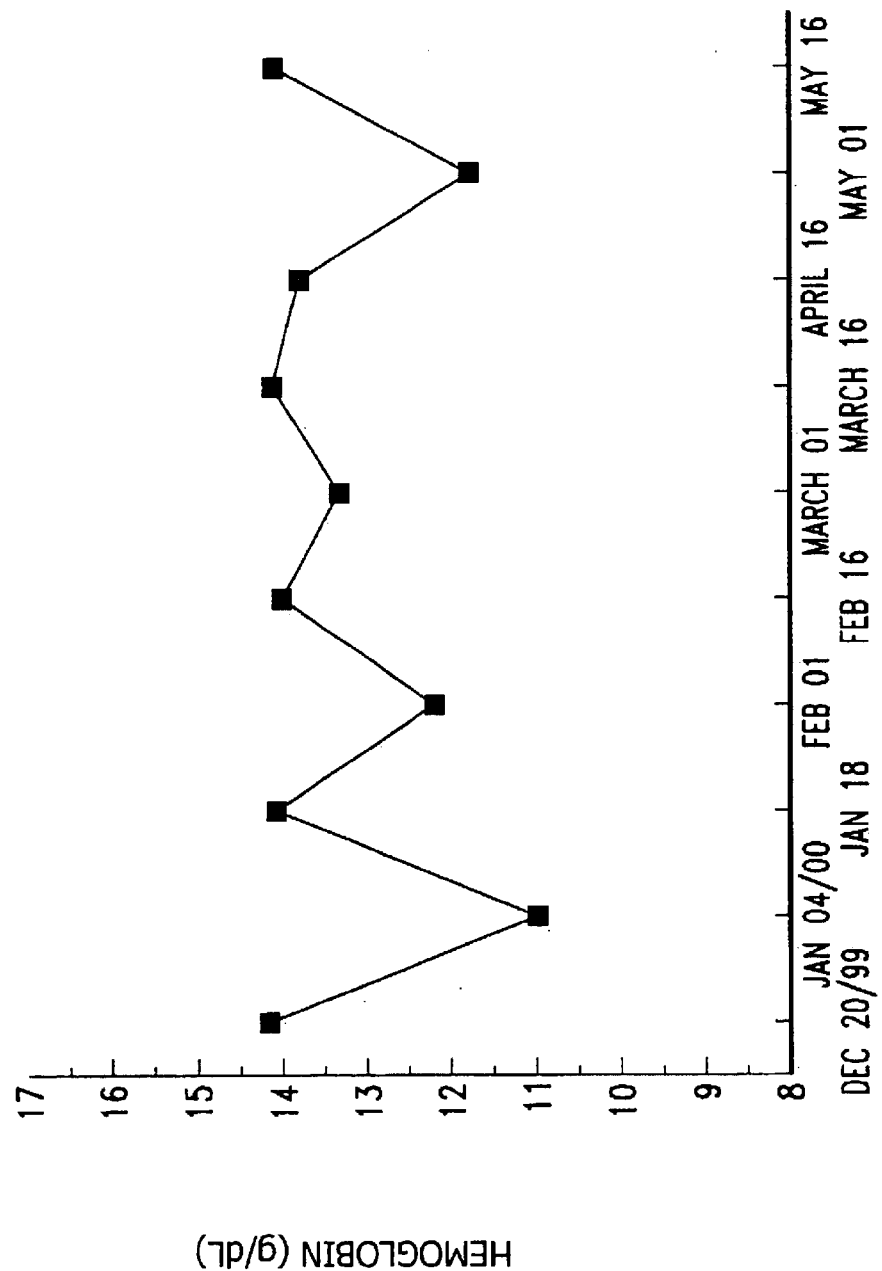
Figure 21B:
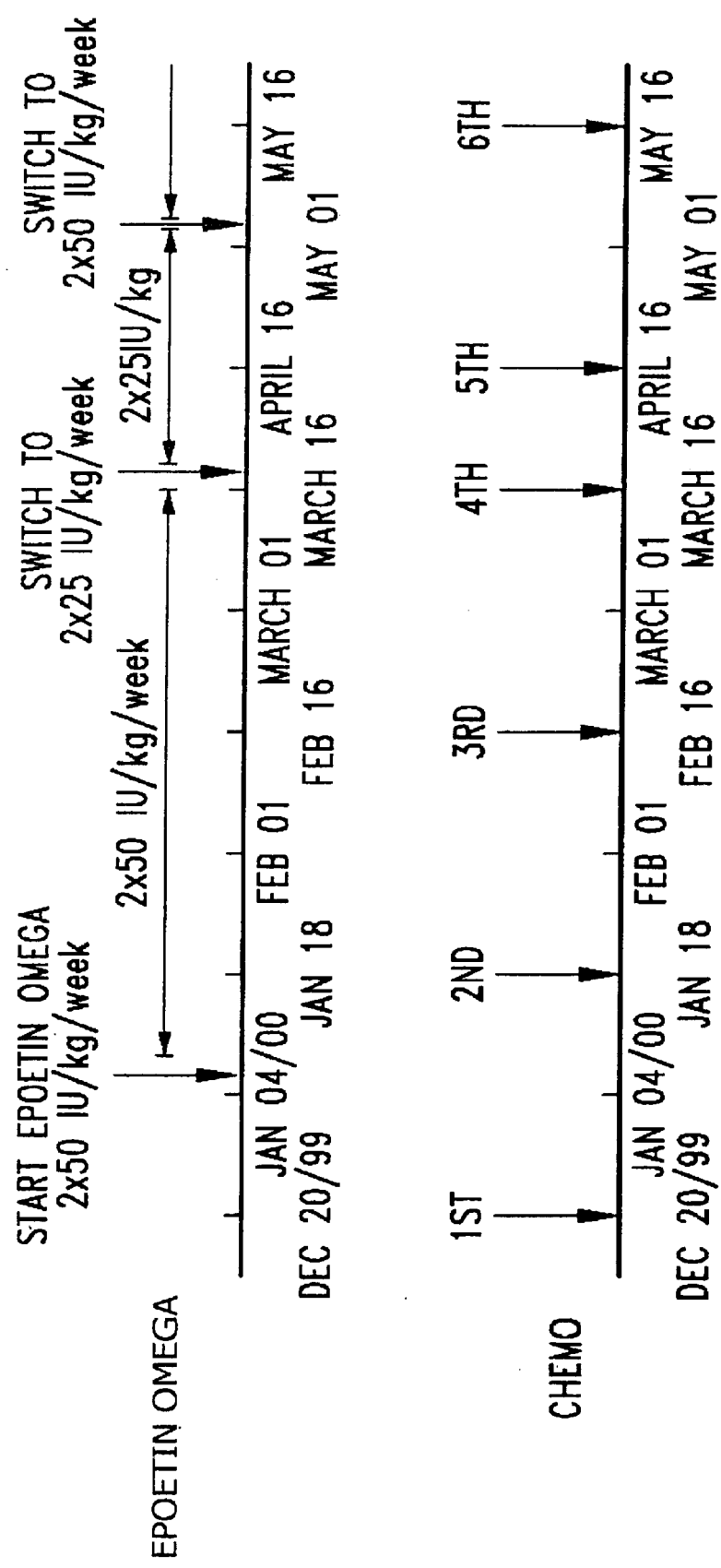

FIG. 21A–B illustrates use of Epoetin Omega to treat anemia associated with chemotherapy. 21A shows a variation of hemoglobin levels over a chemotherapy treatment period. 21B shows a schedule for administering Epoetin Omega and the chemotherapy treatment that results in the hemoglobin levels shown in 21A.

Figure 22:
Figure 23:
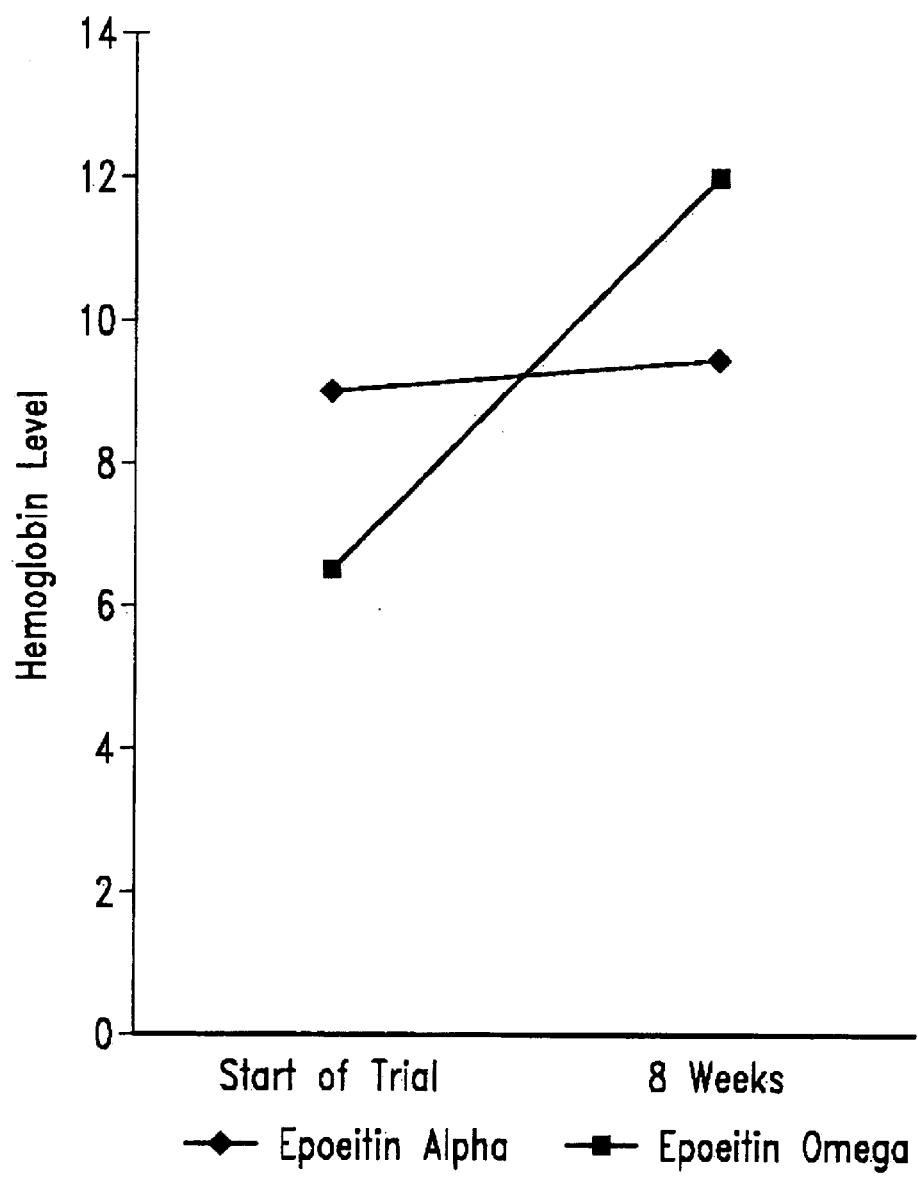

FIG. 22 illustrates a comparison of dose ranges required for treatment of anemia associated with chemotherapy patients obtained from a preliminary eight week study of treatment with Epoetin Omega in comparison to a similar treatment with Epoetin Alfa FIG. 23 illustrates a comparison of hemoglobin increase in Epoetin Omega treated chemotherapy patients obtained from a preliminary eight week study of treatment with Epoetin Omega in comparison to a similar treatment with Epoetin Alfa.

FIG. 24A–D illustrates effectiveness of Epoetin Omega in treating anemia of prematurity (i.e., anemia in premature infants) in a study of 23 infants. 24A shows that the group of Epoetin Omega treated infants needed fewer transfusions than the non-treated control group. 24B–D shows respectively, an increase in (B) RBC count, (C) hematocrit score and (D) hemoglobin level in the Epoetin treated group over the control group.

Figure 25:
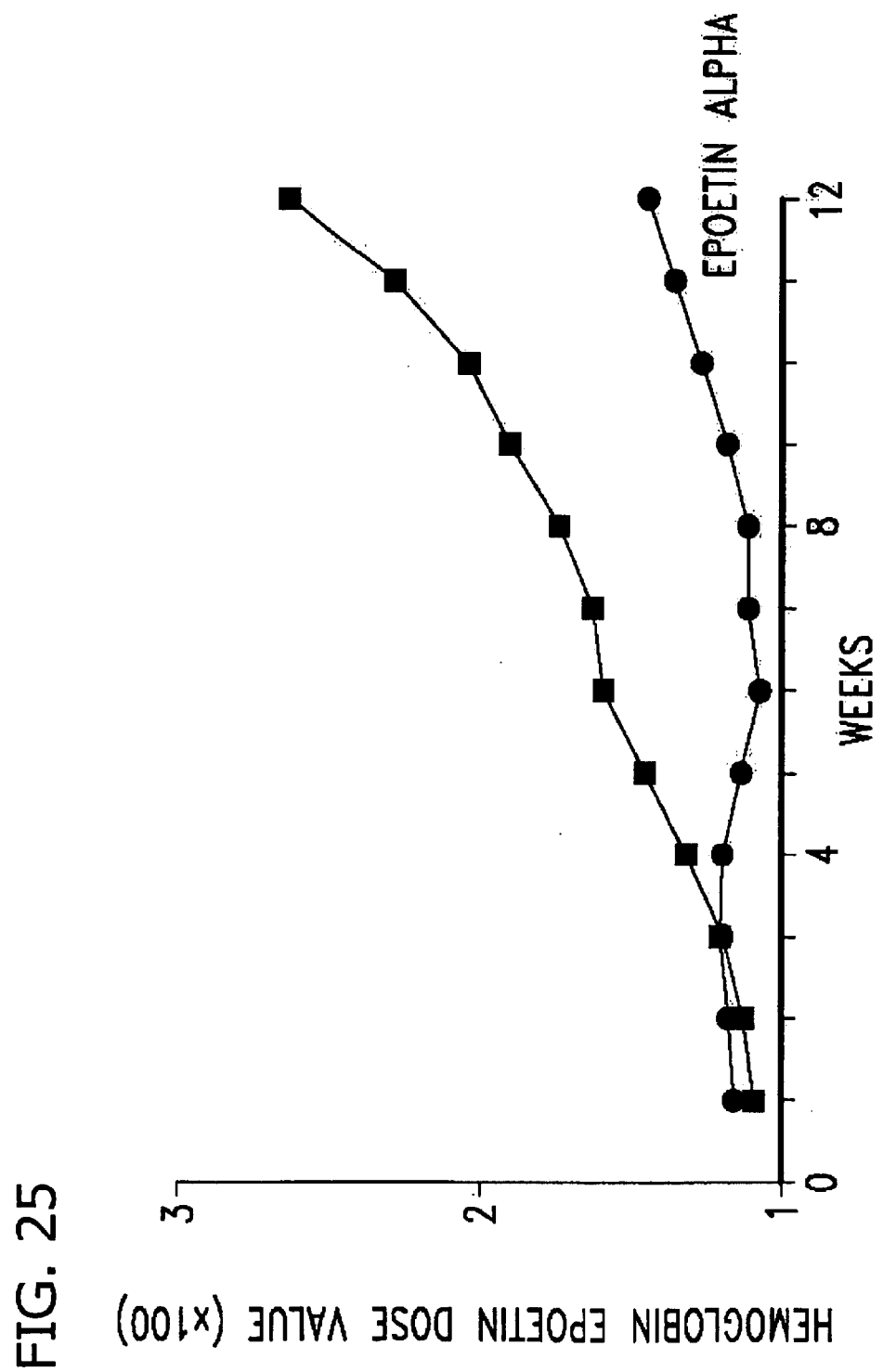

FIG. 25 illustrates comparative dose effectiveness required for treating renal dialysis patients over a twelve week period with Epoetin Omega versus Epoetin Alfa.

Figure 26:
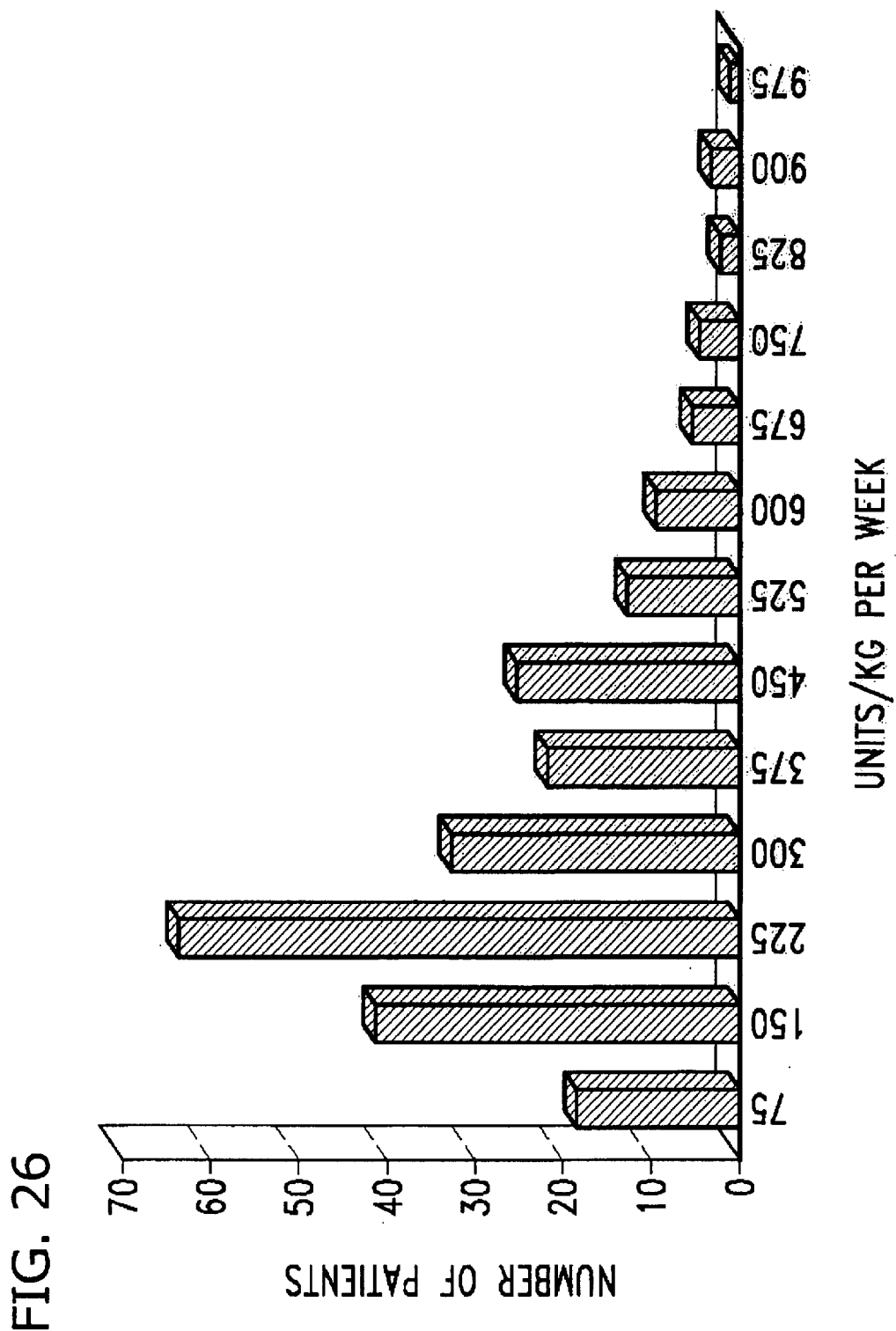

FIG. 26 illustrates a distribution of maintenance dose requirements in a population of renal dialysis patients treated with Epoetin Alfa.

DETAILED DESCRIPTION

Prior to setting forth the present invention in detail, the following definitions are provided to aid in the understanding thereof.

"A symptom associated" with a disease or condition is a symptom that occurs contemporaneously with the disease or condition, or as a result of a treatment of disease or condition. The relationship of disease or condition to the symptom associated therewith may be causal or not. More particularly, the symptom may be independent of disease or condition, or may be dependent on disease or condition because it is directly caused by disease or condition, is indirectly caused by an effect of the disease or condition, or is caused by a primary treatment of disease or condition.

"Adversely effected" or "adverse side effect" is an unwanted biological response, physiological condition, biological measurement, or increase risk thereof, that may occur following the administration of a pharmaceutical agent, particularly rHu EPO to a subject.

A "contraindicated condition" is a first condition or symptom for which the use of a therapy to treat a second condition associated with first, would pose a greater risk or increase the magnitude of an adverse effect than if the first condition was not associated therewith.

"Treating or preventing an anemic condition" means administering a therapy that is effective in preventing, reducing, ameliorating, or abolishing an anemic condition. In one aspect, treating applies to a preexisting anemic condition defined by a measure of anemia such as RBC, hemoglobin, hematocrit or other measure. In another aspect, preventing an anemic condition means treating to reduce or prevent an anemic condition that is statistically expected to occur in an individual as a result of a medical procedure or a medical condition often associated with anemia.

A "heart condition" is a pathological condition of the heart including, but not limited to, congestive heart disease, chronic heart failure, myocardial ischemia and myocardial infarction.

A "therapeutic benefit" is a positive outcome of treating a symptom and may include, for example, a beneficial change in a clinical index such as red blood cell count (RBC), platelet count, hematocrit (HCT), hemoglobin level (hemoglobin) as well as subjective indices such as reduced pain, reduced fatigue, improved vigor or betterment in sense of well being.

A "treatment period" is minimally, the time between first administering a therapy and detecting a therapeutic benefit of the therapy. A treatment period may be extended for a definite or indefinite period beyond the minimal time.

"Without producing or exacerbating an adverse effect" is to not cause an adverse side effect, to not worsen an existing adverse effect, or to not increase the risk of occurrence of the adverse effect by more than 15% over the risk encountered in not treating the subject. Risk may be determined by comparing the incidence of occurrence in a population of similar patients treated with Epoetin Omega to patients treated with a placebo. With regard to hypertension, the risk is less than about 15% that a patient with a "normal level" blood pressure will develop a blood pressure measurement of about 140/80–85 mm Hg or greater. With regard to blood pressure, an increase in diastolic or systolic pressure of less than 10 mm Hg over a pretreatment measurement is not significant.

A "normal level" is a value within a range of values of biological or clinical measurements that is considered by a clinician to be statistically normal in a population of healthy subjects. A list of normal levels can be found in numerous references, for example, *Harrison's Principles of Internal Medicine*. One of ordinary skill in the art will appreciate that what is a "normal level" will vary with such factors as age, weight, gender and may be subject to change with new understandings in the art.

An "IU" or "international unit," is standardized measurement of the amount of a specified biological effect of a drug or naturally occurring material. In particular, an IU for erythropoietin refers to the unit measurement from an in vivo ex-hypoxic polycythaemic mouse assay that is standardized using the World Health Organization's International Reference Preparation of Erythropoietin. The amount of material required to provide one IU for a given material will vary with the source, condition, quality, purity, and/or type of material. The relationship between IUs and other units such as defined by radioimmune assays, may be further understood by reference to Storring et al., *Brit. J. Haematol.* 100:79, 1998, incorporated herein by reference.

Structural Properties of Epoetins

As mentioned in above, erythropoietins prepared from different DNA (genomic or CDNA) and/or in different cell lines have different glycosylation patterns and other attributes resulting in glycoproteins with differing biological activities. In the case of Epoetin Omega, broad peak fractions selected from a final isoelectric purification step, in vivo assay results using a polycythemic mouse assay typically show a range from about 40,000 to about 65,000 IU/mg. More narrowly selected peak fractions have an in vivo activity in the range of 90,000 IU to 120,000 IU per mg. For Epoetin Alfa, in vivo activity of pharmaceutical preparations typically are in the range fo about 110,000 IU per mg. Pharmaceutical preparations are tested in a quality assurance/quality control process using the polycythemic mouse assay before being released for human use. 191:1069–1087), values ranging from about are observed for Epoetin Omega. Radioimmunoassay results indicate an in vitro biological activity in the range of about 200,000 to about 240,000 U/mg for Epoetin Omega. Purified urinary EPO has been reported to have an in vivo activity from about 45,000 IU upwards to about 75,000 or more per mg. In addition, there are likely corresponding differences in the secondary or tertiary structures of the recombinant Erythropoietins (i.e., protein structure/folding) as well as the established differences in carbohydrate composition and bonding strength thereof, as well as stability of the various glycoproteins even though the primary protein sequence may be identical. Each known from of recombinant erythropoietin is a glycoprotein having a myriad of complex carbohydrate chains that include sugars that are N-linked to amino residues and/or O-linked to hydroxy residues. However, the content amount, number, position, bond strength, structure and composition of the carbohydrate linkages differ between the different recombinant erythropoietins and between urinary human erythropoietin. The structure and composition of Epoetin Omega carbohydrate residues has been described for example, by Nimtz et al. *Eur. J. Biochem.* 213:39, (1993); Tsuda et al. *Eur. J. Biochem.* 188:405, (1990); and Sytkowski et al., *Biochem. Biophys. Res. Comm.* 176:698, (1988) each of which are incorporated herein by reference in their entirety.

Sytkowski, et al., reports the results of sodium dodecyl-sulfate polyacrylamide gel electrophoresis (SDS-PAGE) of the Epoetin Omega, which estimates that the glycoprotein has an average molecular weight (ca. 35 kDa) which is comparable to that found for urinary human erythropoietin glycoprotein (34–39 kDa; see, e.g., Miyake, T. et al., in *J. Biol. Chem.* (1977) 252:5558–5564). Additional studies under isoelectric focusing conditions show that Epoetin Omega is comprised of multiple isoforms (i.e., by IEF, about 6–8 isoforms in broad cut fractions and about 6 isoforms in peak fractions) which indicate differing types and amounts of glycosylation and in particular, different amounts of sialylation. In the case of both Alfa and Beta, the isoforms appear to be from 2 to 4 in total number as measured by comparative IEF.

Nimtz, et al., has observed that Epoetin Omega an O-linked oligosaccharide content of less than 1 mole per mole of glycoprotein. In fact, the O-linked oligosaccharide content of Epoetin Omega can be substantially less than 1 mole per mole of glycoprotein, and while the degree of O-glycosylation may vary from batch to batch, it is generally about 0.6 to about 0.7 mole per mole of glycoprotein. Still further investigations on the physiochemical characteristics of Epoetin Omega show that a phosphorylated oligomannosidic moiety is present at the Asn-24 N-glycosylation site. (See, Nimtz et al., in FEBS Letters (1995) 365:203–208 also incorporated by reference.). Epoetin Omega is believed to have three N-glycosylation sites at amino acid residues Asn-24, Asn-38 and Asn-83 and further believed to have an O-glycosylation site at amino acid residue Ser-126. And, unlike urinary human erythropoietin or Epoetin Alfa or Beta, Epoetin Omega, which is expressed from the Apa I fragment of human genomic erythropoietin DNA transformed into BHK host cells, retains substantially all of its in vivo biological activity even after being subjected to conditions that lead to substantial, if not complete, N-deglycosylation. (See, Sytkowski, A. J. et al., in *Biochem. Biophys. Res. Commun.* (1991) 176(2):698–704 also incorporated by reference.). Epetin Omega is unique in this regard because other Epoetins are similarly reported to lose in vivo activity upon N-deglycosylation. Accordingly, the methods disclosed herein may be accomplished with any recombinant erythropoietin exhibiting these and other structural and/or functional characteristics of Epoetin Omega.

Figure 1:
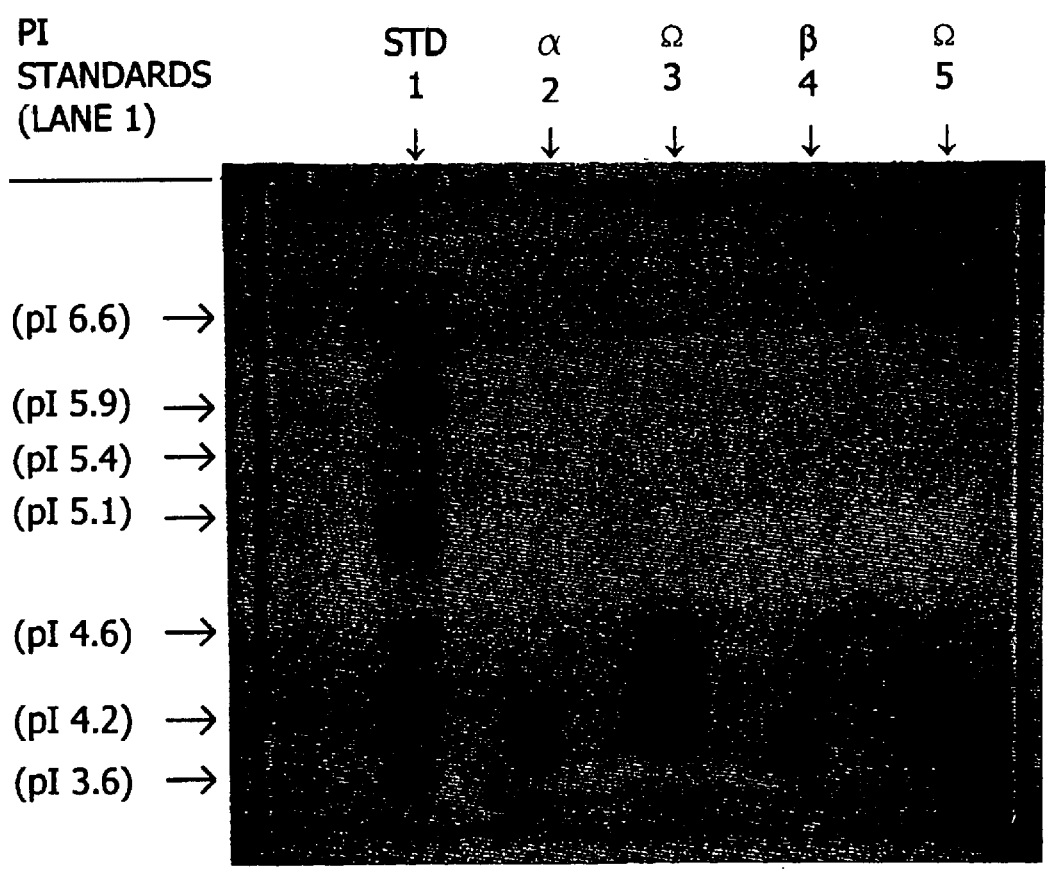
FIG. 1 depicts a Coomassie stained isoelectric focusing gel that illustrates different isoforms contained in sample preparations of epoetins Alfa, Beta, and Omega which result in-part, from different carbohydrate substituents.
Figure 2:
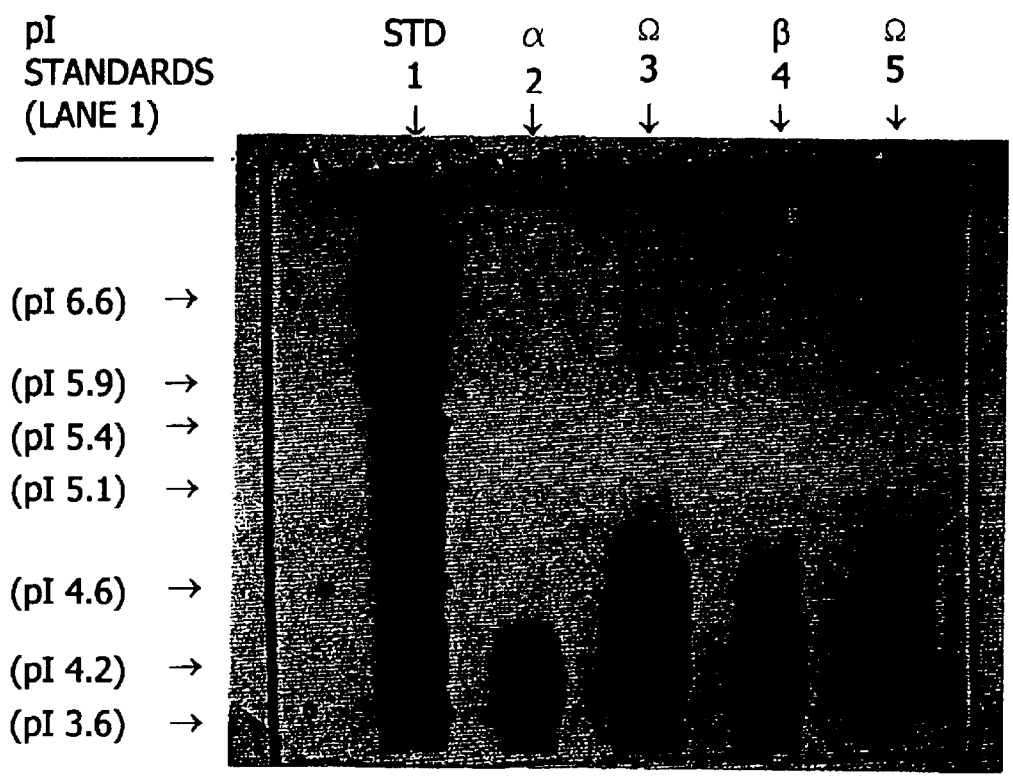
FIG. 2 depicts a silver stained isoelectric focusing gel that illustrates different isoforms contained in sample preparations of Epoetin Alfa compared to Epoetin Beta, and how these differ from Epoetin Omega.
Figure 3:
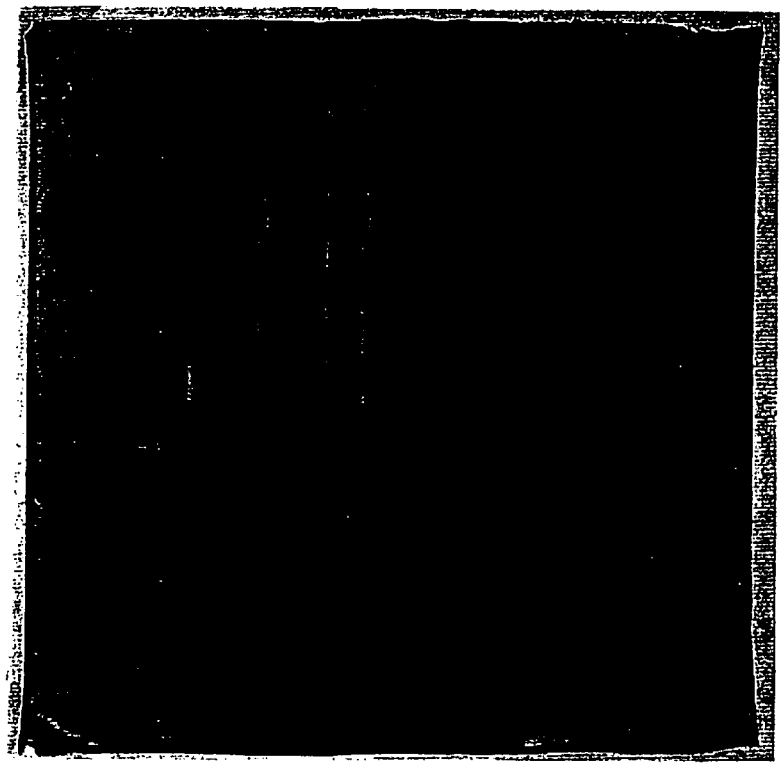
FIG. 3 depicts an SDS Polyacrylamide gel that illustrates different molecular weights in sample preparations of Epoetin Alfa, Beta, and Omega.

FIGS. 1–3 depict gel electrophoresis analyses that visually illustrate structural differences between epoetins Alfa, Beta and Omega FIG. 1 depicts a Coomassie stained isoelectric focusing gel that shows different isoforms contained in sample preparations of epoetins Alfa, Beta, and Omega. These structural differences result, in-part, from different carbohydrate constituents. Epoetins Alfa and Beta have similar compositions with four readily detected isoforms at pI 3.7, 3.8, 3.9 and 4.1. Of these, the major component isoforms for both epoetins Alfa and Beta are those with a pI of 3.8 and 3.9. Epoetin Omega has isoforms at 3.8, 3.9, and 4.1, however, Epoetin Omega also contains less acidic isoforms at pI 4.3, 4.5, and 4.6. In addition, the major isoform components of Epoetin Omega are those with a pI of 3.9, 4.1, 4.3, and 4.5.

FIG. 2 shows a more sensitive, silver stained isoelectric focusing gel which further reveals that Epoetin Beta has minor isoforms at pI 4.2 and 4.6. FIG. 3 shows a silver stained SDS polyacrylamide gel that illustrates one example estimation of different molecular weights in sample preparations of epoetins Alfa, Beta, and Omega. In this analysis, the average molecular weight for the collection of Epoetin Omega isoforms was estimated at 39 kD regardless whether the preparation is dilute, e.g., formulated for therapeutic use (lanes 4 and 5) or from bulk concentrate (lanes 8, 11, and 12). In contrast, for epoetins Alfa and Beta, the collected isoforms were estimated to have molecular weights of 41 for dilute preparations (lanes 6 and 7) or 42 kD, for concentrated preparations (lanes 9 and 10). These estimates are based on one analysis, however other analyses will show other estimates in molecular weights or isoforms. The method of estimation will effect the analysis, however, any thorough analysis will show a difference between the molecular weight of Epoetin Omega and Epoetin Alfa or Beta. While not being bound by theory, it is believed that one explanation for the difference in molecular weights for the dilute and concentrated forms of epoetins Alfa and Beta, is that these erythropoietins are more susceptible to proteolysis or carbohydrate hydrolysis than is Epoetin Omega.

Antigenic Responses

In addition to susceptibility to proteolysis or hydrolysis, the antigenicity of a recombinant drug such as erythropoietin can effect its effectiveness, dose responsiveness, and/or bioavailability over time. The presence of neutralizing IgG anti-EPO antibodies has been reported in some hemodialyzed anemic subjects that fail to respond to Epoetin Alfa or Epoetin Beta treatment. See for example, *New England J Med.*, 1996, 335:523; and *Pharmacol. Res.* 41:313, 2000 incorporated herein by reference. In contrast, Epoetin Omega appears to be less antigenic because at least three clinical trials (herein called the ECU, Brazilian and Argentinean trials described hereafter in greater detail) showed that although all patients were screened for neutralizing antibodies, none were found. While again not being bound by theory, it is believed that the glycosylation pattern of Epoetin Omega possibly results in a molecule more similar to naturally occurring human Erythropoietin or a molecule that is structurally different but simply less antigenic than endogenous EPO found in human serum. In addition, it is likely that differences in tertiary protein structure may contribute to differences in antigenicity. In any case, the antigenic evidence indicates that Epoetin Omega is less likely to be recognized by a human immunosurveillance system than other rHu EPOs. In a recently published study, users of Epoetin Alfa were reported to have anti-rHu EPO antibodies appearing in about 66% of patients on therapy. In contrast, less than about 1% of patients treated with Epoetin Omega across several studies showed the presence of anti-rHu EPO antibodies. While again not being bound by theory, the higher antigenicity of Epoetin Alfa may be at least be part of the cause of reported increasing doses (creeping dose requirements) and/or a lower Area Under the Curve (AUC) measurement of available rHu EPO in patients undergoing a prolonged treatment with Epoetin Alfa. A recently published report from Italy indicates that over 60% of patients treated with Epoetins Alfa or Beta show the presence of antibodies to recombinant EPOs. (Castelli G., et. al, *Detection Of Anti-Erythropoietin Antibodies In Haemodialysis Patients Treated With A Recombinant Human Erythropoietin*, Pharmacol Res. 2000 Mar. 41(3): 313–8 incorporated herein by reference).

Further, it is noted that expression of EPO from the Apa I fragment in cultured cells (BHK and COS) produces millions of units per liter of culture media, indicating a very rapid rate of translation prior to post-translational glycosylation. In contrast, the production rates for systems expressing Alfa and Beta Epoetin are typically in the range of 1400 IU per liter of culture fluid. In the case of Epoetin Omega, it is believed that use of the Apa I genomic fragment produces MRNA that is more efficiently translated within the cell which likely effects the three dimensional structure of the pre-glycosylated protein resulting a protein that is different from other rHu EPOs or urinary EPO despite having the same amino acid sequence. It is now established that receptors for various cytokines are highly sensitive to the higher order protein structures of the signaling factor/cytokines that are able to activate the receptor. Thus, the differences in the clinical or medical effects of Epoetin Omega may not be related solely to the differences in carbohydrate structure, but may be related to other structural factors such as secondary or tertiary structure of the protein.

Adverse Effects Generally

The differences in structure of different epoetins contribute to different therapeutic properties and different risks and magnitudes of adverse side effects. As mentioned above, provided herein are methods for use of Epoetin Omega in treating or preventing an anemic condition without significantly increasing the risk of an adverse side effect, especially increased blood pressure or hypertension. These methods are useful in treating or preventing anemia in patients having a preexisting condition of high blood pressure, and/or in treating patients having associated conditions such as cancer, a heart condition, autoimmune disease, liver dysfunction, cirrhosis, sclerosis of the liver, hepatitis, or renal dysfunction, without significantly producing or exacerbating an adverse side effect. Other adverse side effects include may thrombosis, increased blood platelets, nausea or pain at the injection site resulting form the treatment.

Figure 4:
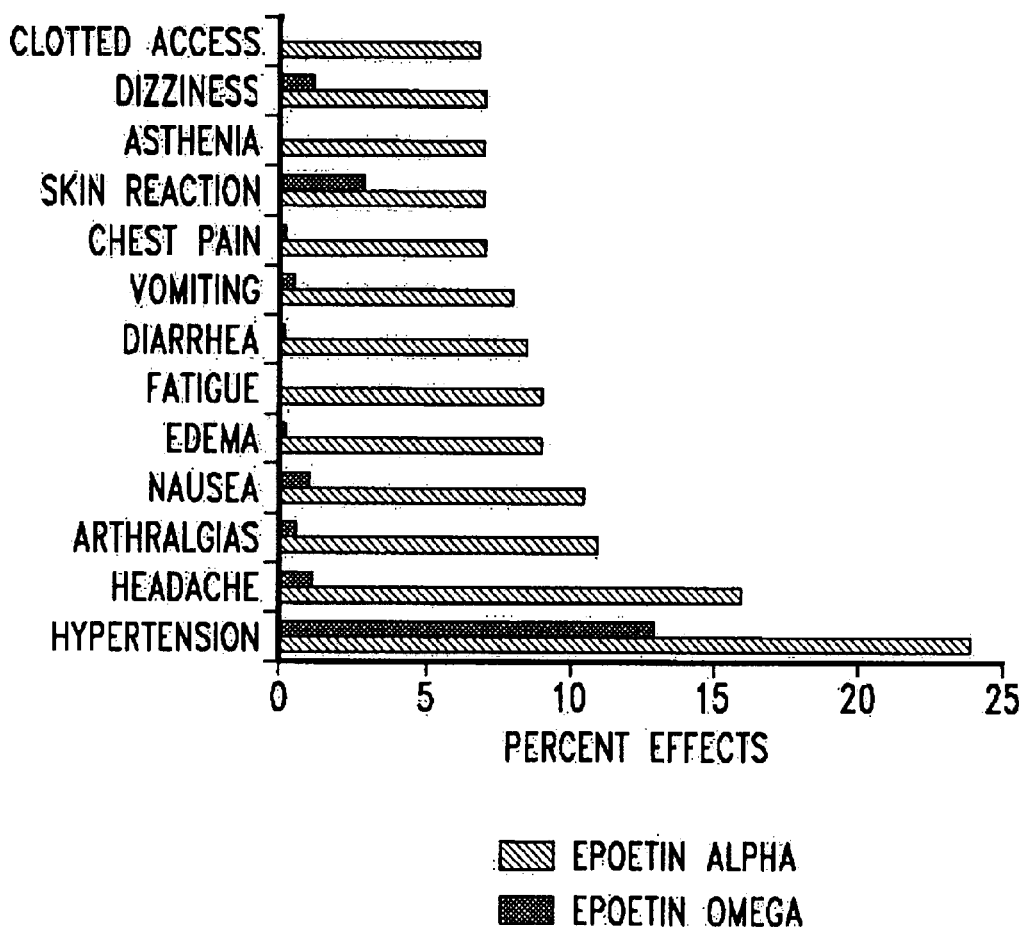
FIG. 4 illustrates clinical trial data showing the occurrence of several adverse side effects in patients treated with Epoetin Omega in comparison to patients treated with Epoetin Alfa.

FIG. 4 shows that the percentage occurrence of the most commonly reported adverse side effects in patients treated with Epoetin Omega is significantly lower than in patients treated with Epoetin Alfa. Of particular importance to the present invention is the occurrence of hypertension. Hypertension is exacerbated by increases in blood pressure which is one risk associated with all erythropoietin treatments. Fatigue is often associated with anemia or with a condition such as liver dysfunction or cancer, or with a primary treatment of such diseases. Nausea is common symptom of certain primary therapeutic treatments such as chemotherapy and radiation therapy.

Hypertension and Blood Pressure

Hypertension, which may be manifested as an aggravation of a preexisting condition and/or newly established hypertension, is the most frequent adverse effect observed in anemic hemodialysis patients treated with Epoetin Alfa and occurs in 25–35% and 40–60% of patients respectively.. Generally a sustained increase of 20 points in blood pressure can be expected in most cases treated with Epoetin Alfa. Generally, treatment with any erythropoietin tends to produce some pro-hypertensive action. According to the current art, Epoetin Alfa and Beta stimulate secretion of endothelian 1, one of the most important endogenous vasoconstrictors from vascular endothelial cells, it inhibits production and release of NO from vascular endothelium, which is an important vasodilating mediator. Epoetin Alfa/Beta effect the rennin-angiotensin-aldosteron system which is a humoral system regulating blood pressure through intravascular volume (aldosteron) and vascular tone (angiotensin II). It increases sympathetic tone and responsiveness of blood vessels thereto. It improves hemoglobin levels leading to a reversal of vasodilation in peripheral tissues that occurs as a local adaptation mechanism to low hemoglobin. All these effects are more pronounced, more frequent, or both in subjects that have reduced renal function or are already more hypertensive than "normal." In contrast, hypertension occurred in only 12.7% of patients treated with Epoetin Omega according the present disclosure (regardless of the route of administration) as shown in clinical trials described in more detail hereafter. Further, it appears that the appearance of hypertension or increase in blood pressure with Epoetin Omega is essentially similar to a placebo (essentially none occurring), which suggests no causal increase due to Epoetin Omega is to be expected.

Accordingly, the methods provided herein include treatments with Epoetin Omega wherein the risk of developing hypertension is less than about 15%. Depending on the severity of the condition treated as well as the dose and duration of treatment the risk is less than about 10% or less than about 5%. In another embodiment, the increase in diastolic blood pressure by treating with Epoetin Omega is less than about 5 to about 10 mm Hg and typically, less than about 7 mm Hg over a treatment period. In another embodiment, the average expected increase in diastolic blood pressure for a population of subjects treated with Epoetin Omega is less than about 5 mm Hg. In another aspect, the increase in diastolic or systolic blood pressure is less than 1.0 mm Hg, and more typically, less than 0.8 mm Hg per unit rise in hemoglobin count (g/dL). In a similar aspect, the increase in diastolic blood pressure is less than 0.5 mm Hg per unit rise in hemoglobin count. These advantages are provided by administering a therapeutic amount of Epoetin Omega in a dose of about 5 to about 150 IU/kg or more typically about 25 to about 75 IU/kg one to three times a week as described in more detail hereafter.

In a trial comparing the effects of Epoetin Omega to Epoetin Alfa on increase in blood pressure (BP) over baseline values, results showed that BP increase was more pronounced in Epoetin Alfa patients. The mean amount of systolic BP increase versus baseline was continuously higher than in Epoetin Omega patients. In addition, despite oscillations, the mean amount of systolic BP increase vs. baseline rose linearly during the trial in Epoetin Alfa patients but not in Epoetin Omega patients. FIG. 5 shows that the area under the mean increase vs. baseline/time curve in Epoetin Alfa patients was 2-fold greater than in Epoetin Omega patients. A similar difference was recorded for the mean increase in diastolic BP but was less pronounced.

FIG. 6A and B shows that this feature becomes more important when considered with the simultaneous and significantly more pronounced effect of Epoetin Omega on hemoglobin levels. More specifically, the ratio of undesirable increase in blood pressure to the desirable increase in hemoglobin is substantially more favorable with Epoetin Omega than Epoetin Alfa. During the first 4 weeks of the trial (fixed doses) the ratio of the mean systolic BP increase/mean hemoglobin increase in Epoetin Alfa patients was between 2.5 and 6.5, and the ratio of the mean diastolic BP increase/mean hemoglobin increase was between 1 and 2.75. This indicates that, on average, for each unit of hemoglobin increase vs. baseline, Epoetin Alfa induced 1 to 6.5 units (mm Hg) rise in BP. In the Epoetin Omega-treated patients, on average, systolic BP showed a 0.2 to 0.8 mm Hg increase, and diastolic BP showed less than a 0.5 mm Hg increase for each unit of hemoglobin increase. During these first weeks of the trial, the ratios in Epoetin Alfa patients were 4 to 12-fold greater than the ratios in Epoetin Omega patients. Therefore, relative to the effect on hemoglobin, Epoetin Omega had markedly less effect on blood pressure than Epoetin Alfa.

This difference between epoetins Alfa and Epoetin Omega effects on systolic and diastolic blood pressure relative to the effects on hemoglobin, was most prominent during the first 8 weeks of the trial, the period when the hemoglobin increase was most marked. The overall difference between the two drugs is also illustrated by the fact that the areas under the ratio/time curves in Epoetin Alfa patients were 4.5 and 2.3-fold greater than in Epoetin Omega patients (for systolic and diastolic blood pressure, respectively). Moreover, with careful monitoring and dose adjustments of Epoetin Omega during a prolonged period, both diastolic and systolic blood pressure can actually show a slight but linear decrease over time as illustrated in FIG. 6C. FIG. 6D further shows that while mean hemoglobin increases over a treatment period, the mean arterial blood pressure decreases during the same period, along with a decrease in the mean dose of Epoetin Omega required to obtain the therapeutic benefit.

Because the reported occurrence of hypertension in Epoetin Alfa or Beta treated patients is at least 2-fold higher than that observed in Epoetin Omega patients, it is certain that the risk of occurrence of hypertension in Epoetin Omega patients is lower for Epoetin Omega treated subjects. The aforementioned trial data established that the effect of Epoetin Alfa on blood pressure was more pronounced than the effect of Epoetin Omega, in terms of the absolute amount of BP increase vs. baseline over a whole treatment period. Further, for each g/dL of hemoglobin increase Epoetin Alfa caused up to 12 times greater BP increase (in mm Hg) than Epoetin Omega. Hence, although the exact increased risk of BP elevation for any single patient is uncertain, it is clear that this risk of hypertension and/or the magnitude of BP increase is lower with Epoetin Omega than with Epoetin Alfa.

The absence or reduction of risk for hypertension or increase in blood pressure is important at all patients, but especially in patients who may not be expected to achieve any response from Epoetin Alfa or Beta. For example, chemo/radiation therapy patients considered for treatment with Epoetin Alfa or Beta present the health professional with the likelihood of little or no therapeutic benefit in the face of high doses (with attendant high costs) and a wait of at least 4 weeks (and sometimes longer than 6 weeks) before any response, if forthcoming at all, can be expected. This presents an increased risk of side effects with little expectation of any increase in RBC, hematocrit, or hemoglobin. In addition, where such therapeutic benefits may occur, the average expectation is about a 10% increase over base levels, e.g., an increase in hemoglobin count from about 8.0 to about 8.8 g/dl hemoglobin, which is substantially below a desired target value of 12 g/dl or above.

An increased risk of hypertension or an increase in blood pressure is a significant adverse side effect of erythropoietin treatment for patients suffering from heart conditions such as chronic heart disease. This is also true when the patient suffers from vascular problems such as arterial sclerosis where the occurrence of high blood pressure may contribute to increase risk of serious side effects such as stroke, CVA, myocardial infarction or death. This is even further complicated in patients at increased risk of thrombosis due to other risk factors connected to coagulation/anticoagulation processes such as platelet count, platelet aggregation, prothrombin time, thrombin time, fibrin/fibrinogen levels, fibrinogen degradation levels, antithrombin 3 levels, etc. These factors operate in concert to form a complex system regulating coagulation and vessel blockage/restriction phenomena. Erythropoietin has a central therapeutic effect of stimulating erythropoiesis which contributes to increased blood viscosity and thus can lead to increased chance of coagulability because erythrocytes tend to occupy the central part of the blood flow and, therefore, tend to "push" platelets aside thereby potentially leading to a higher probability of contacting endothelial cells in 'turbulent flow' leading to a trigger for platelet aggregation and intravascular clotting.

Prior art treatments with Epoetin Alfa, discussed for example under EPOGEN, in the *Physicians Desk Reference*, 53 Ed. (1999), have shown that increased mortality was observed in patients treated with doses of Epoetin Alfa sufficient to achieve a higher hematocrit of 42% than with doses sufficient to obtain a lower hematocrit of 30%. In addition, the incidence of myocardial infarctions, stroke, vascular access thromboses and other thrombotic events were also increased. In a related study, the incident of death in patients undergoing coronary artery bypass surgery and treated with Epoetin Alfa, was 7 per 126 patients versus no deaths among 56 patients receiving a placebo. Four of the 7 deaths occurred after treatment with Epoetin Alfa and each of these four deaths were associated with thrombotic events.

In addition there was a study done on vascularly impaired patients (those with clinical evident cardiac disease, i.e., with chronic heart failure or ischemic heart disease) with Epoetin Alfa, to take them to 42% or above in hematocrit count. That trial was halted by the investigators after only approximately 6 weeks because of results that showed 35% of the patients targeted to a hematocrit of 42% died, while 29% of the patients targeted for a hematocrit of 30% died. Thus, of 1265 patients, of the 42% hematocrit target group there were 221 deaths out of 634 patients; and of the 30% hematocrit target group, 185 died of 631 patients. In addition, vascular access (scribner dialsysis access shunt) thrombosis was reported at 39% and 29% for the high targeted group and low targeted group respectively. Further, other thrombotic events occurred in 22% and 18% of the cases respectively. Finally, of those not having a fatal heart attack, 3.1% and 2.3% respectively had a non-fatal myocardial infarction (heart attack). These results with Epoetin Alpha are summarized below:

Adverse Effects in Treatment of Patients Having Heart Conditions with Epoetin Alfa.*

| Adverse Event | Hematocrit 42% Group | Hematocrit 30% Group |
| --- | --- | --- |
| Death | 35% | 29% |
| Non fatal myocardial: | 3.1% | 2.3% |
| Access Thrombosis | 39% | 29% |
| Other Thrombosis: | 22% | 18% |

*See Amgen web site at www.amgen.com under full prescribing information for physicians, and Source Breaking news release Jun. 25, 1996.

While no similar clinical trial of patients with heart disease being targeted to specific hematocrit counts has yet been conducted with Epoetin Omega, to date there have been thousands of patients across several clinical studies, several of which were vascularly impaired or suffered from heart diseases, who have achieved high hematocrit readings, and there have been no reports of of heart attack or thrombotic events in any case. In a related aspect, with Epoetin Omega there is consistently reported no significant increase in platelet count. In fact, there are numerous cases, including the patients described hereafter in Examples 2 and 4, who had chronic heart failure and tolerated Epoetin Omega well with no adverse events of thrombosis or heart attack or death.

The relationship of thrombotic events to treatment with erythropoietins may be understood, in part, from studies of patients undergoing hemodialysis (HD) who have received erythropoietin treatments. Because of the use of shunts, these patients ordinarily receive heparin or other medication, even including aspirin, in order to maintain a prolonged prothrombin time to prevent A-V shunt thrombosis and clotting in the dialyzer. A-V shunt thrombosis and dialyzer clotting (or clotting in other HD equipment) are not rare in HD patients, and are mainly due to poor monitoring and inaccurate heparin dose adjustments, although an increase in a tendency of thrombosis may contribute to a corresponding increase in the risk of shunt thrombosis.

These general characteristics of shunt thrombosis occurrence also appears applicable to Epoetin Omega. Shunt thrombosis occurred in 10.3% of the i.v. treated and 7.8% of the s.c. treated patients in one multicenter trial (379 i.v. and 450 s.c.-treated patients), which is comparable to reports on other epoetins. Thrombosis or dialyzer clots were not reported in two other trials. One case of dialyzer clotting was reported in the comparative trial vs. Epoetin Alfa. If all the s.c. treated patients from these trials are pooled, then A-V shunt and/or dialyzer clots occurred in 36/530 or 6.8% of the patients (over 11-16-26 weeks Thrombosis incidents are the second most frequent adverse effect in anemic HD patients treated with Epoetin Alfa or Beta and have been reported to occur in 7% to 18% of the patients treated with epoetins Alfa or Beta. A certain percentage of patients have been reported to have significantly altered laboratory tests indicating increased tendency to clotting (platelet number and/or adhesion, prothrombin time etc.). Studies in vitro, in animal models, healthy volunteers, HD or other patients suffering from renal anemia, and "non-renal" patients treated with recombinant epoetins (Alfa and Beta) have identified that treatments with these erythropoietins may have a wide variety of effects on coagulation parameters, such as platelet formation or aggregation, bleeding time, antithrombin levels, fibrinogen levels etc., although each occurs inconsistently and rarely.

However, FIG. 7 shows that treatment of patients with Epoetin Omega does not show any significant increase in the level of blood platelet counts. Platelet counts remain in the normal range throughout a typical treatment protocol. While not being bound by theory, it is believed that the lack of incidence of increase in platelet count may contribute to an overall lower risk of thrombotic events in patients treated with Epoetin Omega than with epoetins Alfa or Beta. This permits Epoetin Omega to be used in treatments of anemic conditions associated with heart conditions without significantly increasing the risk of an adverse thrombotic event. This is an important indication for use of Epoetin Omega without inducing unwanted thrombotic episodes in patients at risk of a thromobosis which is unrelated to a shunt access. In such cases, it would be considered important by a medical professional, to have an EPO available for use that does NOT increase platelets and thus poses no meaningful enhanced risk to thrombosis or restriction of vessels in the EPO targeted patient (other than the natural and foreseeable risk of more red blood cells and thus blood viscosity increased).

Treatment in Patients With Cancer

Treating patients having malignant diseases with Epoetin Omega contributes to the overall prognosis of the disease for a variety of reasons. First, there may be fatigue, nausea, body pain, and the anemia associated with the malignant diseases. The association may be either as an independent or secondary disease condition, a condition caused by the cancer, or a condition that results from a primary therapy for the cancer, such as chemotherapy or radiation therapy. Treatment and improvement of an anemia associated with a cancer, in general, boosts the natural defense mechanisms of the body, boosts the body's ability to function at a "normal" level to fight the disease and oxygenate the tissue, increases the tolerability of a primary treatment (chemo/radiation and associated medicaments) which allows for extended and full application of the indicated primary treatment and/or higher doses, and lowers the risk or occurrence of the adverse side effects of the treatment. Second, treatment with Epoetin Omega is able to relieve fatigue, reduce/eliminate nausea, and/or relieve pain. Third, the aforementioned benefits in turn provide a patient with a more "normal" life, and betterment in mood and sense of well being (i.e., treating the depression, despair/hopelessness or poor mood associated with cancer/treatment) which is a positive outlook that further aids in the prognosis of the treatment.

In addition, a well tolerated treatment regiment with less suffering from the treatment will act as a positive factor for patients deciding to accept additional regiments of treatment with chemo therapy or radiation, or deciding to accept further rounds of treatment if the cancer returns and another course of treatment is prescribed. A patient who has done well or had less "suffering" from the cancer treatment, is more inclined to accept a course of re treatment or alternative treatment, rather than to refuse treatment on the recurrence of cancer rather than suffer again from the treatment itself. It is noted that the following applies to cancer treatment without Epoetin Omega: 76% fatigue, 54% nausea, 23% depression, 20% pain. Thus, as Epoetin Omega works in anemia of cancer, and works to reduce pain and nausea independently from hemoglobin increase, Epoetin Omega adds a valuable and much needed therapy to oncology.

An anemia associated with malignant disease is very similar to the anemia of chronic illness. It is sometimes called uncomplicated hypoproliferative anemia of malignant disease, which is typically a chronic, moderate, normochronic, mormocytic anemia with normal MCV, MCH, and MCHC levels, with hemoglobin levels of 8–10 g/dl and reticulocytoperia and lowered serum iron and TSI, with normal or elevated ferritin. Normal precursors and normal or increased iron stores are found in the bone marrow. It can be multifactorial, but is primarily hypoproliferative anemia. There is a lack of erythropoietin without kidneys being physically affected, and erythropoietin levels are low compared to hemoglobin, i.e., there is no linear inverse relation of hemoglobin to erythropoietin. Cancer patients need more pronounced hypoxia to induce endogenous erythropoietin production. Therefore there is the pronounced need for a replacement and supplementation to endogenous Erythropoietin.

While not being bound by theory, it is believed that part of the explanation for chronic anemia associated with malignant disease includes production or lack of production of various cytokines, and the use of cytotoxic agents, for example cisplatinum or other chemotherapeutic agents in the primary treatment of the cancer. In addition, iron metabolism may be altered, i.e., iron stores cannot be utilized in the most effective way. Reactivity of bone marrow to erythropoietin may often be blunted without bone marrow being affected by the cancer, but rather as a result of the action of various cytokines/cytotoxins/radiation. The life span of RBC is somewhat shorter even without hemolysis or other ways of causing RBC waste due to the action of cytokines in activating macrophages. At any time, chronic malignant anemia can be complicated by several factors. These include (a) infection and/or other inflammatory disease (b) autoimmune hemolytic anemia which induced by some tumors and some cytostatic/cytotoxic agents like methotrexate commonly used in chemotherapy, (c) microangiopathic hemolysis which may be induced by some tumors (d) bleeding and (e) hyperspleenism which very frequently occurs with solid tumors, and (f) bone marrow suppression by cytostatic agents/radiation or tumor tissue.

As illustrated in FIG. 4, Epoetin Omega generally produces significantly lower incidents of adverse side effects than Epoetin Alfa even at dose ranges of about 150 IU/kg per week. The effectiveness of lower doses and reduced adverse effects also provides for more frequent doses as needed, for example up to 7 times a week or more. Treatment of an anemic condition associated with a cancer with epoetins Alfa or Beta typically would require a dose of about 450 to 3500 or more IU per Kg per week. In contrast, treatment using Epoetin Omega is effective at doses that are significantly lower in terms of international units. Treatment with Epoetin Omega may started before, after, or during a primary treatment with a cancer therapy for example, chemotherapy or radiation therapy. The data shown in FIGS. 22 and 23 were taken from patients commencing Epoetin Omega therapy after already arriving having an anemic hemoglobin count of 6.5, which was increased to normal hemoglobin levels (12 or above) in eight weeks. A doctor may treat a patient that is severely anemic and expect a response from Epoetin Omega within a week, rather than to wait 4 to 6 weeks before any response may be hoped for with Epoetin Alfa. In the best situation, Epoetin Omega treatment is started before the commencement or simultaneously (within 3 weeks) as to cancer therapy and may be successfully continued during and follwing the cancer therapy. Typical dose ranges for treatment with Epoetin Omega are described hereafter.

Doses

Each of the treatments using Epoetin Omega according to the present invention use lower doses than required by use of Epoetin Alfa or Epoetin Beta. The lower doses are effective both during an initial titration period (ramp up) where a starting dose to increase hemoglobin is optimized for an individual, and during a maintenance period where a dose is adjusted for prolonged and continuous therapy. In broad embodiments, the treatments use Epoetin Omega administered at a dose of about 5 to about 150 IU/Kg, one to three times per week, or about 25 to about 150 IU/Kg per week In one practice, Epoetin Omega is administered at a dose of about 10 to about 100 IU/Kg per week or about 10 to about 75 IU/Kg, one to two times per week. In another practice, the Epoetin Omega is administered at a dose of about 25 to about 60 IU/Kg, or about 25 to about 35 IU/Kg, two times per week. In still another practice, the Epoetin Omega is administered at a dose of about 50 to about 150 IU/Kg, or about 75 to about 100 IU/Kg, once per week.

These Epoetin Omega doses are less than in typical treatments using epoetins Alfa or Beta., both in dose amount and in frequency. More specifically, epoetins Alfa and Beta are typically administered 3–7 times a week at doses commencing at 150 –>450 IU/Kg per dose, or from 450->3,000 IU/Kg per week (titrated into as many as 6 doses, or given almost daily). In contrast, lower doses of Epoetin Omega and a lower frequency of 1–3 times per week are provided herein, with the long sought after success of once per week dosing proven effective with Epoetin Omega. A typical therapeutic treatment period includes a titration period where Epoetin Omega is administered at an initial dose of about 50 to about 150 IU/kg per week and is adjusted during the titration period to achieve the target therapeutic benefit. In this case it is not unusual for a patient to reach hemoglobin levels of 15 or above up to 19 with no adverse reactions. One example target therapeutic benefit during the titration period is to obtain a hemoglobin count of about 10 to about 12 or more g/dl in hemoglobin. A typical treatment also followed by a maintenance period titrated to sustain the target hemoglobin value. In one example practice, the Epoetin Omega is administered at a dose of about 20–60 IU/kg per week during the maintenance period.

An example comparison of dose requirements in using Epoetin Alfa/Beta versus Epetin Omega in treating anemia in renal dialysis patients is as follows:

|  | Omega | Alfa/Beta |
| --- | --- | --- |
| Initial Dosing per Kg week: | 75 to 120 | 150 to >900 |
| Maintenance Dosing per Kg/Week: | 25 to 75 | 100 to >900 |

For contrast, FIG. 26 illustrates an example distribution of maintenance dose requirements in a population of renal dialysis patients treated with Epoetin Alfa.

In the treatment of anemia associated with oncology, (i.e., associated with chemotherapy or radiation therapy where patients are treated with rHu EPO in an attempt to prevent the need for blood transfusion, a comparison of required doses is as follows:

|  | Omega | Alfa/Beta |
| --- | --- | --- |
| Initial Dosing per Kg week: | 75 to 150 | 500 to 3,500 |
| Maintenance Dosing per Kg/WEEK: | 20 to 150 | 500 to >3500 |

In this comparison, it should be noted that treatment with Epoetin Alfa was effective in raising hemoglobin to a sufficient level to avoid transfusions in less than 40% of the patients, while all patients receiving Epoetin Omega obtained hemoglobin levels raised to levels sufficient to avoid transfusion.

FIG. 22 visually illustrates a comparison between high and low dosing requirements of Epoetin Omega and Alfa in treating anemia in chemotherapy patients who were treated over an eight week period with Epoetin Omega in comparison to similar studies of treatment of chemotherapy patients with Epoetin Alfa. The dosing amounts shown are adjusted for an average patient weight of 70 kg. The epoetins were administered at a frequency of two doses per week. The Epoetin Omega treated patients required a total weekly dose of between about 4000 and 12,000 IU in comparison to a total weekly dose of 40,000 to 100,000 or more IU required for the Epoetin Alfa patients treated. It is notable in this example that Epoetin Omega achieves or sustains target hemoglobin, where Alfa/Beta have 60% non responders at virtually any dosage. When adjusted for the average 70 kg patient, the dose per administration was about 28 to 86 IU/kg for Epoetin Omega in comparison to about 285 to 571 IU/kg for Epoetin Alfa. Thus, Epoetin Omega is about 6.6 to about 10 times more potent in dosing regiment than Epoetin Alfa on a unit by unit basis in the treatment of anemia associated with chemotherapy. In addition, FIG. 23 illustrates that Epoetin Omega was significantly more effective in raising hemoglobin levels than Epoetin Alfa, in that Epoetin Omega worked on the anemia. After the end of 8 weeks, the Epoetin Omega treated patients achieved an increased hemoglobin count from an average starting value of about 6.5 g/dl to the target value of 12 g/dl. In contrast, the Epoetin Alfa treated patients on average achieved only a modest increase from about 9.0 to 9.5 g/dl over the same period. Because biological pharmaceuticals such as erythropoietins are typically sold on a unit basis, the greater potency of Epoetin Omega practically translates into a substantial cost savings for erythropoietin therapy. For example, at the time of this application, 100,000 IU per week of Alfa translates into 1,000 USD at $10 per 1,000 IU. Compared to 4,000 IU to 12,000 of Epoetin Omega, if priced competitively, at 40 to 120 USD for the week. Over 8 weeks of therapy, Epoetin Omega at 8,000 IU per week would be about $80 per week ×8 weeks or $640 USD; compared to 100,000 or more IUs (e.g., 25 vials of 4,000 per week) or 1,000 per week or $8,000 USD over 8 weeks of use.

Dosing may be adjusted according to the condition being treated and the response of the subject. In treating fatigue or pain, a lower initial dose of 5–50 IU/kg per week, or more typically 20–60 IU/kg is administered once or twice a week for an initial titration period of 1 to 4 weeks. During the titration period, the subject is assessed for reduced pain or fatigue. If the subject complains of continued symptoms, the dose is adjusted upward in increments that typically increase by ½ the initial dose. Alternatively, the initial dose is administered twice a week. Conversely, if the subject reports reduced pain or fatigue, the dose may be adjusted downwardly by about 10 IU/kg to obtain a minimal dose that is effective for a maintenance period without unnecessarily increasing a risk of adverse side effects.

For treatment of common dialysis anemia, the average titration dose for Epoetin Alfa is typically about in the range of about 150–450 IU/kg per week divided into three doses per week, with an average of about 200 IU/kg or more per dose. Similarly, the typical maintenance dose for Epoetin Alfa is 225 IU/Kg per week divided into two or three doses, with 25% of patients requiring more than 600 IU/Kg per week. In contrast the average titration dose for Epoetin Omega invention is about 32 IU/kg two to three times per week and the average maintenance dose is 23 IU/kg two to three times, or 40 to 100 IU/kg per week divided into one, two or three times per week; and the average Epoetin Omega maintenance dialysis dose is 20 to 70 IU/kg per week divided into one, two or three doses per week. This is illustrated, for example, in FIG. 8, which shows high, low, and average dose requirements for Epoetin Alfa in comparison to Epoetin Omega for treatment of anemia during the maintenance period for dialysis patients. A typical maintenance dose for Epoetin Omega applied after a target hemoglobin value has been reached is about ½ to about ⅓ the amount used during the titration phase. The dose can be reduced to a lesser dose frequency than with Epoetin Alfa or Beta, in part because of the longer bioavailability and increased potency of Epoetin Omega. An increase in a dose during the maintenance phase is seldom needed for Epoetin Omega. The doses should be adjusted in small amounts, typically by about 5 to about 25 IU/kg per week. A typical weekly Epoetin Omega dose for 60–70% of hemodialysis patients was about 40 to about 60 IU/Kg/week. Approximately 45% of the patients could maintain a target hemoglobin level without any drug at all for one or two or even three weeks. Therefore, with Epoetin Omega once weekly injections of about 50–150 or 40–100 IU/kg can also be used for a large number of patients. Since aversion to injections/needles is a normal conditon for dialysis or chronic disease patients, this lower frequency of actual administration is a big advantage, especially if the dose must be given s.c. route (more painful because of needles and nerves in the skin) to achieve yet a lower total weekly dose. This differs substantially from any known treatment with Epoetin Alfa or Beta where dose frequency of once a week is not effective so that even at doses as high as 200 IU/kg are not sufficient to maintain hemoglobin levels in the target range. The use of much lower doses of Epoetin Omega and less frequency of injection/administration results in several concomitant advantages, including lower total cost of therapy, reduced risk of EPO dose related side effects, and less to no likelihood of "creeping" dosage requirements than are exhibited by patients treated with Epoetin Alfa or Beta.

Another important feature of the Epoetin Omega treatments provided herein is the lack of lag time in achieving a response in comparison to use of other epoetins, meaning virtually immediate response or no latency. For example, FIGS. 15C, 16 and 17 illustrate that hemoglobin levels increase after the first week of administration of Epoetin Omega. This contrast with Epoetin Alfa which typically does not show a hemoglobin increase until at least after the second week of treatment in the anemia of dialysis, and 4 weeks or longer in the case of attempted treatment by Alfa/Beta in the anemia of oncology. Accordingly, the titration and maintenance doses for Epoetin Omega can be established more rapidly and with greater certainty, than for epoetins Alfa or Beta.

The lower and less frequent doses required for Epoetin Omega further contribute to a lower incidence or risk or magnitude of adverse side effects such as increased blood pressure, hypertension, platelet stimulation/increase, body pain, injection site pain, or thrombosis, in comparison to other epoetins. In addition, the lower doses and higher bioavailability coupled with essentially no to low risk of any adverse event, permit Epoetin Omega to be administered to treat mild symptomatic conditions such as fatigue or body pain. These conditions may be treated whether or not they are associated with anemia, or whether or not they are associated with congestive heart failure, cancer, autoimmune disease or liver dysfunction or other chronic disease.

Clinical Trials of Treatment of Anemia Associated With a Disease

Traditionally, anemia of end stage renal disease is the major indication for use of recombinant human erythropoietin(s). This is mainly because endogenous EPO is made in the kidney. In the condition of kidney disease whether pre-ESRD or ESRD, the kidney slows or stops its EPO production, making hormone (erythropoietin) replacement therapy a treatment method that is required to address the anemia. Efficacy and safety of Epoetin Omega in this indication has been investigated in several trials involving adult hemodialyzed (HD) patients. While the results described herein relate to anemia associated with renal disease, the low doses, rapid responses, and low frequency of side effects indicate that Epoetin Omega is useful for treating anemia associated with other conditions, especially conditions which may be contraindicated for epoetins Alfa and Beta because of the high doses, slower responses and more severe side effects.

A single-dose, single-blind, cross-over trial comparing s.c. Epoetin Omega to Epoetin Alfa tested 18 regularly dialyzed anemic patients (13 M/5 F, age 33–75, 51.8±10.8 years) showed that Epoetin Omega has greater relative bioavailability than Epoetin Alfa. Patients were randomly assigned to receive either 50 IU/kg Epoetin Alfa (n=9) or Epoetin Omega (n=9) s.c. After a 7-day wash-out period, Epoetin Alfa—patients were switched to Epoetin Omega and vice versa with the same dosages. Baseline Erythropoietin values were determined immediately before each drug administration. Plasma erythropoietin was measured by a commercially available EPO-ELISA kit (Boehringer Mannheim, cat. no. 1693417, monoclonal anti-EPO antibody, "CHO Epoetin" calibrated against the WHO IRP standard).

Both the mean $C_{max}$ and the mean area under the concentration curve ($AUC_{0-120}$) were considerably higher after Epoetin Omega injection than after Epoetin Alfa injection. As shown in Table I, and graphically represented in FIG. 9, the mean plasma levels of erythropoietin was greater and sustained over a longer period of time than for Epoetin Alfa. More specifically, the $t_{1/\beta}$ had a longer duration after Epoetin Omega injection In individual patient data for 16 of the 18 patients, $C_{max}$ and AUC after Epoetin Omega injection were both higher than after Epoetin Alfa injection. Also, the $t_{1/2\beta}$ was extended in 12 of 18 patients after the Epoetin Omega treatment.

TABLE I

Pharmacokinetic data on Epoetin Omega and Epoetin Alfa after a single s.c. injection (50 IU/kg). AUC and elimination half-life were calculated on plasma concentrations corrected for the baseline values.
Values are X ± SID.

|  | $t_{max}$(h) | $C_{max}$(IU/L) | $AUC_{0-120}$(IU × h/L) | $t_{\frac{1}{2}\beta}$(h) |
|---|---|---|---|---|
| Epoetin Omega | 25.1 ± 9.8 | 57.4 ± 25.2 | 1933.9 ± 943.6 | 23.4 ± 9.6 |
| Epoetin Alfa | 23. ± 7.6 | 35.1 ± 15.1 | 981 ± 614.6 | 17.8 ± 5.3 |
| Epoetin Omega/ Epoetin Alfa | — | 1.72 ± 0.72 | 2.43 ± 1.81 | 1.41 ± 0.68 |

The aforementioned data illustrates the greater relative bioavailability of Epoetin Omega after s.c. injection (based on AUC comparisons). The $C_{max}$ data and the plasma concentration-time curve, together with the observation that the elimination phases of the two drugs were not so dramatically different, suggests that the difference is due to absorption differences between the two types of erythropoietin. Based on this and other available data, it has been estimated that the half absorption time ($t_{1/2\alpha}$) for Epoetin Omega (estimated by fitting to first order kinetics) was about 5 hours and that the average Epoetin Alfa $t_{1/2\alpha}$ was approximately 60% longer. These data show that a single dose of an equal amount (IU/kg) of Epoetin Omega and Epoetin Alfa results in about a 1.72 fold higher erythropoietin plasma level using Epoetin Omega. Further, Epoetin Omega is eliminated from plasma more slowly as illustrated by an average 1.41 fold ratio in terminal elimination half-life. This contributes to markedly greater bioavailability of Epoetin Omega as illustrated by the 2.43 ratio in AUC value for Epoetin Omega in comparison to Epoetin Alfa.

FIG. 10 shows that when doses of the two erythropoietins are adjusted to maintain a therapeutic response for a maintenance period of 12 weeks after an initial dose of 2×50 IU/kg/week s.c. that was fixed during the first 4 weeks, the mean plasma concentration remains higher for Epoetin Omega (FIG. 10A) than Epoetin Alfa (FIG. 10B) resulting in a need for a lower doses of Epoetin Omega over the maintenance period. More specifically, FIG. 10, shows that Epoetin Omega (mean) doses continuously decreased during the trial, while the erythropoietin plasma concentrations rose. In contrast, after the first period of fixed dosing, Epoetin Alfa doses needed to be increased, and erythropoietin plasma concentrations increased little. The consequence is that Epoetin Omega doses were continuously lower than the Epoetin Alfa doses, and plasma erythropoietin concentrations in Epoetin Omega patients were continuously higher.

This Epoetin Omega vs. Epoetin Alfa difference in the dose to plasma concentration effect was most clearly observed seen during the first 4 weeks of treatment. Although identical doses (i.e., 2×50 IU/kg) were applied, there was no rise in erythropoietin plasma concentrations in Epoetin Alfa patients while there was a significant almost 2-fold rise in Erythropoietin plasma concentrations in Epoetin Omega patients. The fact that the plasma concentration continued to increase despite the reduction in Epoetin Omega doses, indicates better accumulation of Epoetin Omega than Epoetin Alfa during the course of a therapeutic treatment. It is usually preferred that doses be administered by s.c. injection rather than i.v. injection because s.c. administration tends to lengthen the time that erythropoietin remains above baseline levels, however, it is believed that these accumulation and availability differences between Epoetin Omega and Epoetin Alfa will also be observed for i.v. administration.

The aforementioned data (and other data not presented herein) show that that Epoetin Omega is better absorbed than Epoetin Alfa because a significantly higher $C_{max}$ is obtained (Table I), and the absorption half-life appears significantly shorter. A comparison of this data to a study of Epoetin Beta, for example, as published in *Drugs*, 1995; 49:232, incorporated herein by reference, shows that Epoetin Omega half-life is also 2-3-fold lower than that reported for Epoetin Beta.

Clearance time for Epoetin Omega also differs significantly from other epoetins, e.g., the clearance time for Epoetin Omega is prolonged in comparison to Epoetin Alfa. More specifically, a clearance rate of approximately 0.26±0.12 mU/min/mL was observed for Epoetin Omega in comparison to a clearance rate of 0.68±0.31 mU/min/mL of Epoetin Alfa, as reported by Storring et al. Clearance time, like absorption, also appears to be dose independent.

In initial trials, Epoetin Omega was applied intravenously. As discussed above, administration of erythropoietin, however, is now preferably by the s.c. route. However, as summarized in Table H, the open, uncontrolled i.v. trials evaluated over 100 patients and clearly showed that Epoetin Omega effectively stimulated erythropoiesis in subjects having anemia associated with end stage renal disease. The administration of very low doses of Epoetin Omega had remarkable effects on both hemoglobin and HCT, which were at low baseline levels even though iron metabolism parameters may not have been idea. Individual data from two trials (the Brazilian and the Argentinean trial) reveal, that no patient involved received more than 230 IU/kg/week. In addition to the effects on hematological parameters the Argentinean trial and a third set of Indian trials showed that 4 weeks of Epoetin Omega treatment effectively increased the work performance and effort tolerance of patients, as evidenced by significantly increased working capacity and oxygen consumption.

FIG. 11 shows that the incidents of pain at the s.c. injection site using a visual analogue scale (VAS) was significantly less for Epoetin Omega treated patients than those treated with Epoetin Alfa. The mean weakly VAS score from weeks 1 to 14 of the trial was significantly higher in the Epoetin Alfa than in the Epoetin Omega group. The difference between the drugs is also illustrated by the fact that the area under the means of the mean weekly VAS scores/time curve was 1.7-fold larger in Epoetin Alfa than in Epoetin Omega group. These data suggest that Epoetin Omega was better tolerated than Epoetin Alfa with respect to the local pain after an s.c. injection.

TABLE II

Efficacy of i.v. epoetin omega in correcting renal anemia in HD patients.
Summary of the results of 6 open, uncontrolled trials.

| Trial (Reference) | Duration | No. of patients and dosing (IU/kg) | Iron | Baseline Hb (g/dL) and/or HCT (%) | Dose variations during trial | End point Hb and/or HCT | Other notices |
|---|---|---|---|---|---|---|---|
| India 1) | 12 weeks | 20, 3 × 25 i.v. 8 weeks, then 3 × 36 | 400 mg/day p.o. + Folic acid 5 mg/day | Hb 6.0 ± 1.0 HCT 18.3 ± 3 | — | Hb 9.9 ± 1.4 HCT 29.9 ± 4.7 | 9/20 reached 10.0 g/dL Hb Continuous rise in Hb and HCT |
| India 2) | 12 weeks | 13, 3 × 25 i.v. 8 weeks, then 3 × 36 | Iron dextran i.v. from 2. week on | Hb 6.1 (mean) HCT 18 (mean) | — | Hb 8.0 (mean) HCT 26 (mean) | Continuous rise in Hb and HCT |
| India 3) | 12 weeks | 15, 3 × 25 i.v. 8 weeks, then 3 × 36 | Not stated | Hb 5.6 ± 1.1 HCT 16.5 ± 3.3 | — | Hb 7.9 ± 1.4 HCT 23.5 ± 4.6 | Continuous rise in Hb and HCT |
| India 4 | 12 weeks | 22, 3 × 25 i.v. 8 weeks, then 3 × 36 | 150–300 mg/day p.o. + 200–300 mg/week i.v. | Hb 5.9 ± 1.1 HCT 18.2 ± 3.4 | — | Hb 8.4 ± 1.9 HCT 26 ± 6 | 3/22 reached 10 g/dL Hb Continuous rise in Hb and HCT |
| Brazil | 16 weeks | 15, 3 × 50 i.v. (high dose, HD) 15, 3 × 25 i.v. (low dose, LD) Single dose ⇑ by 25 IU after week 4 if Hb rose ≦ 1.0 g/dL, and during trial according to response. When Hb 10.0 g/dL, dose⇓ by ⅓ - i.v. or s.c. (50%) | According to ferritin, i.v. or p.o., or without (ferritin >500 mg/mL) | HD: Hb 6.4 (mean) HCT 20 (mean) LD: Hb 7.0 (mean) HCT 22.5 (mean) | HD group (IU/kg/wk): wk 1–6: 145–155 wk 7–12: 100–110 wk 12–16: 70–100 LD group (IU/kg/wk): wk 1–4: 70–75 wk 5–13: 100–110 wk 14–16: 90–95 Overall average | HD: Hb 10.4 (mean) HCT 32.2 (mean) LD: Hb 10.2 (mean) HCT 32.1 (mean) | Continuous rise in Hb and HCT in both dosage groups, but more rapid and prominent with the higher dose. HD group patients all reached 10.0 g/dL Hb. Time to target 7.4 ± 2.7 weeks |
| Argentina | 16 weeks | 9, 3 × 25 i.v. | 160 mg/day p.o. | Hb 5.7 ± 1.0 | | Hb 8.9 ± 1.1 | Continuous rise in Hb and HCT |
| | | 9, 3 × 50 i.v. Single dose ⇑ by 25 IU in 2-wk intervals, according to response in Hb | according to ferritin | HCT 17.0 ± 3.2 | wk 1–3: X = 100–115 SD = 30–36 wk 4–9: X = 80–95 SD = 20–45 wk 10–13: X = 100–120 SD = 50–60 wk 14–16: X = 120–145 SD = 55–60 | HCT 26.7 ± 3.2 | HCT regardless of the initial dose. |

A fourth open, uncontrolled European trial included more than a 1000 HD patients. In total, 829 patients were evaluated for 26 weeks. Of these patients, 379 were administered Epoetin Omega by i.v. injection and 450 were administered by s.c. injection.

In a pilot study using an initial dose of 3×40 IU/kg/week, either i.v. or s.c., both hemoglobin and HCT rose quickly, leading to a reduction in the dose as early as after two weeks of treatment in majority of the patients. Accordingly, for the main part of the trial, initial doses of 3×30 IU/kg week i.v. or s.c. were used. Included patients had hemoglobin $\leq 9.0$ g/dL, HCT $\leq 27\%$, and all standard inclusion/exclusion criteria for efficacy/safety trials of rHu EPOs.

The main objective of the trial was to increase and maintain hemoglobin at 10.0–12.0 g/dL, or at least to induce a rise in hemoglobin $\geq 2.0$ g/dL and HCT >6% over the first 12 weeks of the trial. Dosing was divided in two periods: a titration period (needed to achieve the target) and a maintenance period (needed to keep hemoglobin and HCT within the target values with as little variability as possible). Dose adjustments were made every two weeks according to hemoglobin response and tolerability (single dose up or down by 5–20 IU/kg). Iron was supplemented orally or intravenously, depending on the iron status, so as to keep ferritin >150 µg/L and transferrin saturation >20%. It is noted that in this study, patients were screened for the presence of EPO antibodies, and only two patients in the 1,000 showed presence of antibodies. Thus, the incidence of antibody formation with Epoetin Omega seems to be less than 0.2%.

FIGS. 12 and 13 illustrate changes in hemoglobin as a result of this trial. Changes in HCT followed the same pattern, i.e., the same dynamics and (relative) increase during the trial. A rapid rise in hemoglobin was seen in both treatment groups, but the response was generally better in the s.c. group. In contrast to known responses from treatment with of epoetins Alfa and Beta, there was no latency in Epoetin Omega response. The rise in hemoglobin was significant after the first week in the s.c. group and after the second week of treatment in the i.v. group. The mean hemoglobin values increased continuously throughout the trial in both groups. The increase (in terms of the slope and the maximum mean values reached) was greater in the s.c. group. In detail, during the first 4 weeks of the trial the mean hemoglobin in the i.v. group rose, on average, by 0.4 g/dL over 2 weeks (R=0.98), while the slope in the s.c. group indicated a 0.8 g/dL increase over 2 weeks (R=0.98). Subsequent increases in the mean hemoglobin slowed due to the dose reductions. During the first 11 weeks the mean hemoglobin in the i.v. group rose, on average, by 0.3 g/dL over each 2-week period (R=0.97), while the slope of the mean hemoglobin increase in the s.c. group indicated a 0.4 g/dL /2 weeks increase. As illustrated in FIG. 13, this smaller i.v. vs. s.c. difference was due to larger dose reductions in the s.c. group.

The "titration" doses were generally low in both groups. However, they were consistently lower in the s.c. than in the i.v. group. The maximum weekly "titration" dose in the i.v. group was 106±15 IU/kg (week 26) and the overall mean weekly "titration" dose was 96±4 IU/kg. In the s.c. group, the maximum mean weekly "titration" dose was 95±2 IU/kg. The overall mean weekly "titration" dose in the s.c. group was 78±3 IU/kg.

In terms of dose adjustments, trends in dose alterations during the trial reflected the therapeutic response. In the i.v. group, the mean weekly "titration" dose decreased continuously during the first 7–10 weeks of the trial indicating a rapid and significant rise in hemoglobin (requiring dose reductions). However, from week 10 onward, the "titration" dose in the i.v. group gradually rose. This trend indicates that some patients were poor responders and needed more time and more Epoetin Omega to achieve the target. The proportion of patients still on "titration" regime at week 26 was about 10%. In contrast, the mean weekly "titration" dose in the s.c. group continuously decreased during the whole trial (with some oscillations between weeks 7 and 14), indicating a better response in this group, The proportion of patients on "titration" regime at week 26 in the s.c. group was <5%.

Changes of weekly doses (FIG. 13) indicate that some patients had reached the target hemoglobin and hence started the maintenance dosing by week 2 in the i.v. group and week 3 in the s.c. group (probably due to somewhat lower baseline hemoglobin in the s.c. group). In general, at any given time during the trial a larger proportion of s.c. than i.v. treated patients were on "maintenance" dosing.

"Maintenance" doses were lower than titration doses in both groups. The mean weekly "maintenance" doses in the i.v. group varied from <40 IU/kg to approximately 70 IU/kg and the overall mean "maintenance" dose was 70±4 IU/kg/week. In the s.c. group, the mean "maintenance" weekly doses were between 30 IU/kg and 50 IU/kg. The overall mean "maintenance" dose was 49±3 IU/kg/week (FIG. 13). Therefore, in general it may be stated that the maintenance dose of Epoetin Omega is typically about 30 to about 70 IU per Kg per week, with an average in the range of about 45 to about 70 IU per Kg per week. In contrast, the typical maintenance dose of Epoetin Alfa is about 150 to about 600 IU per Kg per week, with a reported average USA dose of about 200 to about 225 IU per Kg per week. Thus, an "average" dose of Epoetin Omega may be stated to be about 55 IU per Kg per week, compared to the "average" dose for maintenance of 225 IU per Kg per week for Epoetin Alfa. Accordingly, Epoetin Omega is about 400% more potent than Epoetin Alfa in accomplishing the same hemoglobin/hematocrit maintenance in a renal dialysis patient. This drastically higher potency is highly unexpected given than in medicine generally, a difference of from 10 to 25% in the potency of a class of medication is considered to be sufficiently different and to make a new compound "different" and "superior".

Three other additional open trials confirmed the efficacy of s.c. Epoetin Omega in anemic HD patients. The first was a Slovenian trial that included 27 adults with hemoglobin $\leq 8.5$ g/dL and HCT$\leq 27\%$ over 11 weeks. The second was a Macedonian trial that included 22 adults with hemoglobin <8.5 g/dL and HCT <27%. Both trials were evaluated over 16 weeks. Other inclusion/exclusion criteria were standard for rHu-EPO trials. Iron was supplemented i.v., depending on serum ferritin and transferrin saturation. In both trials, the initial dose was 3×30 IU/kg/week s.c. Doses were adjusted gradually (single dose up or down by 5–20 IU/kg), in 2-week intervals according to hemoglobin response. The goal was to achieve and maintain hemoglobin 10.0–12.0 g/dL and HCT 30–35%. The main outcomes are summarized in FIG. 14 and FIG. 15. Although only changes in hemoglobin are shown, changes in HCT followed the same pattern.

FIG. 14 shows results from the Slovenian trial illustrating that the mean hemoglobin value continuously increased over 11 weeks. The slope (R=0.98) indicated a 0.52 g/dL mean hemoglobin increase over each 2-week period. During this period, the mean dose did not change significantly. The first 3 patients (11.1%) reached the target by the end of week 3.

By the end of week 6, 54% of the patients had reached the target. After the week 10, there were only 3 patients still below the target. Two of those had achieved ≧2.0 g/dL hemoglobin increase vs. baseline, and only one was a "poor responder" (this patient) did not respond to previous Epoetin Alfa treatment, either). Four other "poor responders" to Epoetin Alfa responded very well to Epoetin Omega (did not differ from the rest of the group).

FIG. 15 shows results from the Macedonian trial illustrating that the mean hemoglobin also rose rapidly and linearly over the first 10 weeks of the trial (R=0.98). The slope indicates a 1.05 g/dL/2 weeks increase over that time. Doses were very similar during the first 8 weeks and then decreased. The first 3 patients (13.6%) reached the target hemoglobin by the end of week 3. Half of the patients were "within" the target hemoglobin range by the end of week 7, and there were only 5 (22.7%) patients below the target after week 8 of treatment. Only 1 patient was below the target after week 10. All 5 patients who needed more than 8 weeks to target had TSI continuously <20%. The last patient to reach the target (by the end of week 15) did so only after his TSI had risen beyond 20%.

The third was a Polish open trial that included 29 patients over 24 weeks treated with Epoetin Omega. FIG. 15B illustrates results of this trial showing a rapid rise in mean hemoglobin with no latency period (upper panel). This rise was especially rapid and linear during the first 7 weeks (middle panel) with a simultaneous decrease in the required mean weekly dose of Epoetin Omega over the treatment period (lower panel). The initial titration dose was 3×25 IU/kg/week and doses are expressed as total weekly amounts. In this trial, the maximum mean doses used was about 6900 IU/week corresponding to a dose about 100 IU/kg/week or 3×33 IU/kg/week.

Still another trial was conducted, which was a single blind, randomized, cross-over trial with two 16-week parallel treatment periods (and an 8-week "wash out" in-between) comparing Epoetin Omega and Epoetin Alfa. The trial included adult HD patients (age 18–80 years) with hemoglobin <8.5 g/dL and HCT <27%. Other exclusion/inclusion criteria were standard for rHu-EPO clinical trials. Patients were assigned to receive Epoetin Omega or Epoetin Alfa (30 patients in each group) for 16 weeks (phase 1). After the "wash-out", Epoetin Omega patients were switched to Epoetin Alfa and vice versa, for another 16-week treatment period (phase 2). Both phases of the trial have been completed, but only the first phase is discussed herein. The initial dose was set to be 2×50 IU/kg/week s.c. of either drug. Doses were fixed during the first 4 weeks of treatment. After that, doses were adjusted (single dose up or down by 25 IU/kg) according to hemoglobin response and tolerability. Iron was supplemented i.v., in order to keep TSI >30% and serum ferritin >500 ng/L. The aim was to reach and maintain hemoglobin levels within 10.0–12.0 g/dL range.

FIGS. 16 and 17 illustrate comparative advantages of Epoetin Omega over Epoetin Alfa in hemoglobin response versus dose over time. Both drugs induced hemoglobin increase, but difference between them was apparent as shown. FIG. 16 shows that hemoglobin levels were continuously higher (except at baseline) in Epoetin Omega patients. Changes in hemoglobin were more rapid and prominent. The mean hemoglobin rose during the very first week while there was no effect of Epoetin Alfa in this period. During first 4 weeks (fixed dose 2×5O IU/kg/week) mean hemoglobin in Epoetin Omega patients increased by 0.47 g/dL/week (on average) and by 0.2 g/dL/week in Epoetin Alfa patients. After that, mean hemoglobin in Epoetin Omega patients continued to increase rapidly (average weekly increase during first 11 weeks 0.32 g/dL although the mean dose linearly decreased. hemoglobin rose in Epoetin Alfa patients, as well, but slower (average weekly increase of the mean hemoglobin during first 11 weeks 0.25 g/dL). Epoetin Alfa dose, however, was significantly higher at that time—between weeks 5 and 12 the mean weekly dose of Epoetin Alfa was 1.2 to 1.8-fold higher than that of Epoetin Omega.

Significantly higher mean hemoglobin levels were reached in the Epoetin Omega group, and target level was reached significantly sooner (by the end of week 7 vs. week 12 in the Epoetin Alfa group). Mean hemoglobin was successfully maintained beyond the lower target limit in Epoetin Omega patients throughout the trial. From week 13 onward mean weekly dose rose back to the initial values reflecting increments in a few patients that did not respond to treatment as markedly as the rest of the group. However, maximum mean weekly dose in the Epoetin Omega group did not exceed minimum mean weekly doses in the Epoetin Alfa group. The overall cumulative dose of Epoetin Omega used was about ⅓ lower than that of Epoetin Alfa, i.e., the total amount of IU needed for treatment of 2 patients with Epoetin Alfa equaled the amount of IUs needed for treatment of 3 patients on Epoetin Omega.

Differences in dose-effect relationship between the two drugs are even more pronounced when illustrated by increase of hemoglobin vs. baseline, and, especially, as a ratio of hemoglobin increase/weekly dose as shown in FIG. 17. At the end of week 4 (fixed dose interval) this ratio was 4-fold higher in Epoetin Omega than in Epoetin Alfa patients, and was continuously significantly higher (approximately 1.5 to 3.5-fold). The area under the ratio/time curve was 2.3-fold larger in the Epoetin Omega than in the Epoetin Alfa group.

This phase of the trial demonstrated greater dose and effect advantages of Epoetin Omega in comparison Epoetin Alfa. The same advantages of Epoetin Omega were observed in the switching phase of the trial, i.e., where patients who had previously been treated with Epoetin Alfa, are switched to Epoetin Omega and vice versa.

Anemia of Prematurity

Efficacy and safety of Epoetin Omega in the anemia of prematurity has been investigated in one randomized, open-labeled, controlled trial. The main objective was to determine whether administration of Epoetin Omega would reduce the need for packed red cell transfusions. Infants with age at birth <31 weeks and body weight at birth <1500 g were eligible for inclusion into the trial. Infants with major congenital malformations, intracranial hemorrhage, hemolysis, hemorrhagic polycythemia (venous Hct >0.6) and arterial hypertension were excluded. Fifty premature neonates were randomly assigned to either receive Epoetin Omega or not. There were 2 dropouts in each group due to recurrent infections.

If the body weight at birth was >1000 g, treatment started at postnatal age >1 week, otherwise treatment started at 30 weeks gestational age, and lasted 4 weeks, i.e., until 34 weeks of gestational age. Treatment included Epoetin Omega 3×100 IU/kg/week s.c. with initially 3.0 mg/kg/day ferric iron in food, subsequently modified according to serum iron and ferritin (to avoid iron toxicity), vitamin E at 0.5 mg/day orally, energy intake of 460–505 kJ/kg/day. Packed red cell transfusions were given if needed (Hct<35% or 30% or 20%, depending on the level of respiratory support and clinical signs of anemia). The control group received the same treatment, except for Epoetin Omega. Patients were closely observed for 4 weeks after treatment and then followed for up to 1 year of corrected age. In a longer term follow up patients were evaluated for psychomotor, neurological and somatic development.

Figure 24:
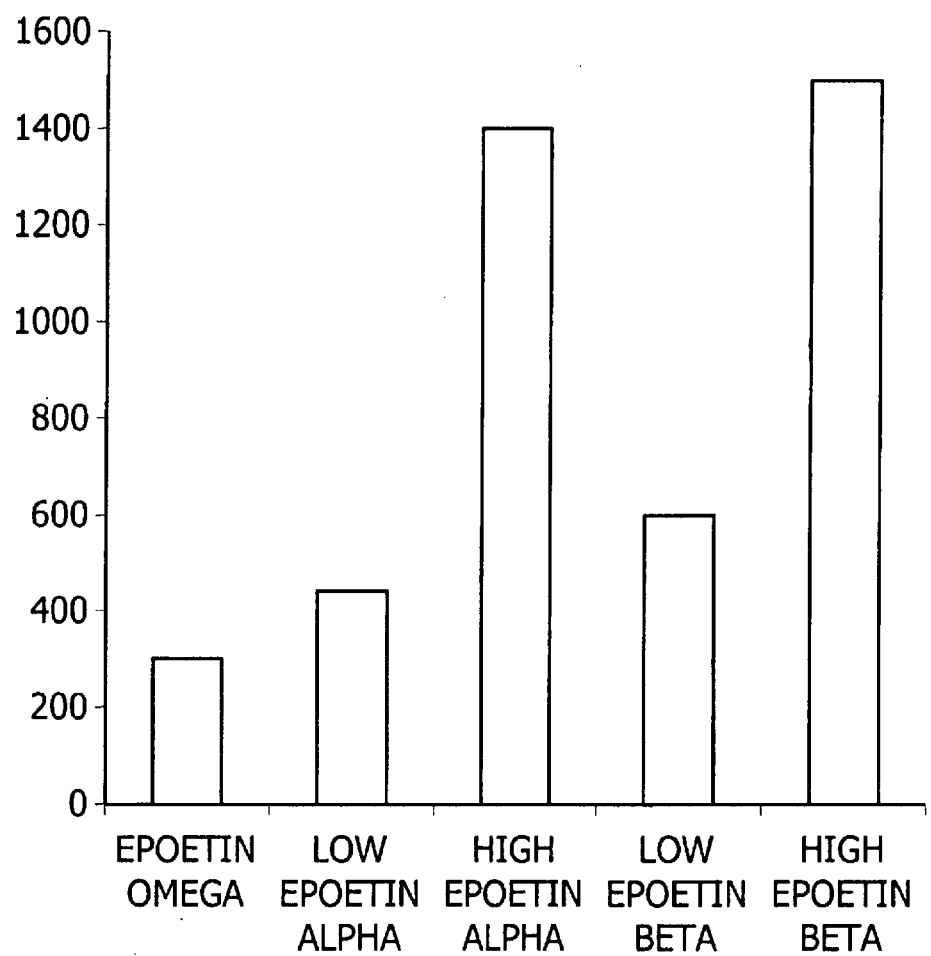

FIG. 24 illustrates results of the study. All treated patients responded well and there was no need to administer a dose increment. There was no difference between the groups regarding iron, energy and vitamin E intake. In the pretreatment phase infants were equally transfused. However, only 1 infant (4.3%) in the Epoetin Omega group needed PRC transfusion (1 unit) during the treatment phase vs. 8 infants (34.8%) in the control group (FIG. 24A). None of the Epoetin Omega-treated patients needed a transfusion in the one month follow up vs. 5 infants (21.7%) in the control group. Overall, during these 8 weeks only 1 infant received 1 PRC unit in the Epoetin Omega group vs. 13 infants in the control group (56.5%) (FIGS. III–12). Reticulocyte levels were continuously significantly higher in the Epoetin Omega-treated group (FIG. 24B). The area under the reticulocyte/time curve was 1.45-fold greater in Epoetin Omega-treated vs. control patients, and 8.3-fold greater if the baseline (beginning of treatment) reticulocyte count was subtracted. Further, the decline in Hemoglobinand Hct was markedly more pronounced in the control group than in Epoetin Omega patients. Mean Hemoglobinand Hct values in the Epoetin Omega group were significantly higher and were continuously kept beyond the lower desirable levels in the treatment phase than in the control group (FIG. 24C and D). Serum erythropoietin levels were significantly higher in the Epoetin Omega treated patients than in control patients at the end of treatment period. Serum ferritin decreased in both groups but the decline was more pronounced in Epoetin Omega-treated infants, probably a result of significantly more stimulated erythropoiesis.

Excluding the effect of Epoetin Omega on erythropoiesis, there was no other clinical or laboratory test difference between infants in the two treatment groups. No differences were observed regarding somatic, neurological and psychomotor development up to 1 year corrected age. Anemia of prematurity is a transient, iron and/or vitamin resistant, multifactorial, but primarily hypoproliferative anemia, due to an absolute or relative erythropoietin deficiency and hyporesponsivenes to (low) endogenous erythropoietin.

In comparison to trials involving thousands of preterm infants both Epoetin Alfa and Epoetin Beta also effectively correct anemia of prematurity however, these require substantially higher doses than the Epoetin Omega In terms of effective dose, Table III illustrates the range of doses that have been applied in trails in this indication using Epoetins Alfa or Beta. The dose used in the Epoetin Omega is lower than doses of either Epoetin Alfa or Epoetin Beta, listed in Table III which have been reported to be more effective than placebo. FIG. 24 illustrates the high and low doses of Epoetin Alfa required to be effective in comparison to Epoetin Omega. Doses of 300 IU/kg/week of Epoetin Omega' over four weeks (observation 8 weeks) almost completely abolished the need for transfusions (only 1 infant received 1 unit). Epoetin Omega undoubtedly stimulated erythropoiesis as shown by measurements of reticulocytes, hemoglobin and Hct. The data strongly suggest that Epoetin Omega is more effective than other Epoetins in treating anemia of prematurity.

TABLE III

Doses of Epoetin Alfa and Beta (s.c.) effective in the anemia of prematurity.

| Reference | Dose reported better than placebo or control |
|---|---|
| Pediatrics 1995; 95:1 | 5 × 100 IU/kg/wk Alfa |
| J Pediatrics 1992; 120:586 | 5 × 100 IU/kg/wk Alfa |
| Pediatrics 1994; 93:918 | 3 × 200 IU/kg/wk Alfa |
| Pediatric Res 1993; 34:675 | 3 × 150 IU/kglwk Alfa |
| J Pediatrics 1991; 119:781 | 200 IU/kg every other day/ 20 days Alfa |
| Ped Hematol & Oncol 1998; 15:415 | 3 × 300 IU/kg/wk Alfa |
| J Pediatrics 1997; 131:661 | 200 IU/kg/day over 14 days Alfa |
| NEJM 1994; 330:1173 | 3 × 250 IU/kg/wk Beta |
| Pediatrics 1993; 92:512 | 3 × 200 ≈ 3 × 300 IU/kg/wk Beta |
| J Pediatrics 1998; 132:866 | 3 × 250 IU/kg/wk ≈ 3 × 500 IU/kg/wk, Beta |
| J Perinatal & Neonat Nursing 1997; 11:57 | 3 × 200 or 5 × 200 IU/kg/wk (recommended) |

Summary of Clinical Trial Data

The comparative clinical trial data discussed above shows that there are several advantages of s.c. Epoetin Omega over Epoetin Alfa. In general, Epoetin Omega is more effective (more potent) in correcting anemia. More specifically, with Epoetin Omega the increase in hemoglobin is markedly more rapid and it begins during the first week of treatment, i.e., there is no "time lag" between the start of the treatment and the onset of response. There is a shorter time needed to reach the target hemoglobin values. In addition, if drugs are dosed according to their therapeutic response and tolerability, higher maximum levels of hemoglobin are achieved with Epoetin Omega than Epoetin Alfa. Moreover, the significantly better effects on hemoglobin, dynamics and absolute amount of hemoglobin increase, are achieved with significantly lower Unit doses of Epoetin Omega than epoetins Alfa or Beta. In all, in terms of correction of anemia, patients required about one third less (IU/kg) to achieve better results. Further, Epoetin Omega has less effect on blood pressure and hypertension than epoetins Alfa or Beta.

Thus, Epoetin Omega is significantly different in its pharmacological characteristics from other epoetins. In addition, the benefits of a pharmaceutical such as Epoetin are not only characterized by the type of positive action imparted (i.e., increase in RBC, hematocrit, hemoglobin or iron uptake) but also by its inherent potency which results in a lower bioload inflicted on the patient's body and/or the corresponding absence or lowering adverse side effects that may endanger the patient's life or otherwise make it impossible to use the pharmaceutical. This is especially apparent in the case of hypertension, which adversely effects the risk of severe occurrences such as myocardial infarction or stroke.

The following Examples are offered to further illustrates aspects of the methods, effects and advantages of treating symptoms in patients using Epoetin Omega:

EXAMPLE 1

DOSING PROCEDURE FOR EPOETIN OMEGA IN TREATMENT OF ANEMIA ASSOCIATED WITH A DISEASE

The following protocol represents a typical titration and maintenance procedure for administering a therapeutic amount of Epoetin Omega that is effective in treating the symptom of anemia associated with a disease without substantially producing or exacerbating an adverse side effect.

Epoetin Omega is typically formulated in doses of 2000 or 4000 IU/ml with a pharmaceutically acceptable carrier or diluent for subcutaneous (s.c) or intravenous (i.v) injection. An example carrier or diluent in a 1 ml volume might include: sodium chloride (NaCl) 8.18 mg, monobasic sodium phosphate (NaH$_2$PO$_4$xH$_2$O) 1.56 mg, sodium hydroxide (NaOH) to pH 7.2, and human serum albumin 1.0.

An initial titration dose 50–100 IU/kg/week (e.g. 2×30 IU/kg/week) is initiated, and is adjusted gradually, in 2-week intervals, according to the hemoglobin response and tolerability.

Epoetin Omega is typically formulated in doses of 2000 or 4000 IU/ml with a pharmaceutically acceptable carrier or diluent for subcutaneous (s.c) or intravenous (i..v) injection. An example carrier or diluent in a 1 ml volume might include: sodium chloride (NaCl) 8.18 mg, monobasic sodium phosphate (NaH$_2$PO$_4$xH$_4$O) 1.56 mg, sodium hydroxide (NaOH) to pH 7.2, and human serum albumin 1.0 mg.

A maintenance dosing procedure starts with a dose about ¼ to ⅓ lower than the last titration dose. The dose may be additionally decreased (in a single dose down by maximum 20 IU/kg) after prolonged periods of steady hemoglobin levels, or if clear trends towards the upper target limit are observed (>0.5 g/dL increase over any 2 week period). The dose should be increased if the hemoglobin decreases below the lower target limit (to the preceding level), or if a clear descending trend is observed but still within the desired range (hemoglobin decrease >0.5 g/dL over any 2-week period) a single dose up by a maximum 20 IU/kg/week should be used.

Treatment with Epoetin Omega should be transiently discontinued if the hemoglobin increases too rapidly (≧4.0 g/dL in any 2-week period) or if it goes beyond the upper target limit. Thereafter, Epoetin Omega should be resumed with up to 50% lower doses.

When switching to Epoetin Omega after treatment with other erythropoietins, the more potent effect of Epoetin Omega should be considered. If treatment with Epoetin Omega is to be started immediately after a treatment with Epoetin Alfa or Beta, doses should be adjusted downwardly accordingly. For example, if Epoetin Omega is to be introduced during maintenance after a titration dose of 3×150 IU/kg/week of Epoetin Alfa, the Epoetin Omega should be started at a maximum 60–100 IU/kg/week s.c., divided in 2 weekly injections. A formulation containing Epoetin Omega may be included with a kit containing instructions in this regard. The instructions may include for example, a reference table that compares a dose of Epoetin Alfa to Epoetin Omega for a given set of conditions.

EXAMPLE 2

TREATMENT OF ANEMIA ASSOCIATED WITH HYPERTENSION, HEART CONDITION AND CANCER

A 71 year old man of 128 pounds displayed congestive heart failure, coronary artery disease and generalized arteriosclerosis. In addition, the subject suffers from adenocarcinoma of the lung and colon is presented with an iron deficiency anemia and suffers from chronic fatigue among other symptoms. The subject patient has a history of diabetes mellitus and myocardial infarction. Primary treatment of both the lung cancer and the colon cancer includes resection. The patient is hypertensive and has been treated with LASIX and LISINOPRIL to manage his blood pressure. At intake, subject had a hemoglobin count of 12.9, a HCT count of 39.6% and a platelet count of 213 K.

During the course of the cancer therapy the subject is administered Epoetin Omega at a dose of about 3×2000 IU/wk, which corresponds to about 100 IU/kg/week at 33 IU/kg per administration. There was no significant increase in blood pressure, no thrombotic effects and no worsening of cardiac function. The response of this subject indicates that even for a patient having conditions associated with cancer that are counter-indicated for treatment with Epoetin Alfa, i.e., hypertension, chronic heart failure and coronary artery disease, the use of Epoetin Omega did not exacerbate preexisting hypertension nor produce any thrombotic episodes.

EXAMPLE 3

TREATMENT OF SUBJECTS HAVING ANEMIC CONDITIONS ASSOCIATED WITH CANCER

1. Fatigue with Breast and Bone Cancer

A subject complaining of chronic fatigue is a 125 pound, 85 year old woman with a long history of metastatic breast cancer to bone and the right pleural space has managed the cancer by treatment with the chemotherapeutic drugs AREDIA and ARIMEDEX. Further treatment with OXYCONTIN results in fatigue and somnambulism. In addition, the subject receives systemic low level radiation therapy in the form of a MATASTRON (strontium-89) injection. Prior to these treatments, she received primary treatment of the breast carcinoma by external beam radiation along with the chemotherapeutic agents CYTOXAN, ADRIAMYCIN and MEGACE. The subject suffers from shortness of breath, pain, weakness and fatigue which are exacerbated by the foregoing treatments. She also had symptoms of dyspnea and anemia which may be caused by the chemotherapy and/or from the underlying basis of the disease.

Hematology results show among other things, a RBC 3.68, hemoglobin 10.6, HCT 31.9% and platelets at 279 K/ul. atient commenced Epoetin Omega therapy about 1992. The subject was administered 4000 IU of Epoetin Omega (80 IU/kg) two to three times a week in addition to other therapies directed to managing spread of the cancer and removing fluids from the pleural space. After several months,the subject obtained normal RBC of 5.3 M/ul, (norm is 4.04–5.48 for females) hemoglobin of 14.1 g/dl (norm is 12.2–16.2 for females) HCT 46.37% (norm is 37.7–47.9 for females) and a blood platelet count of 228 K/ul (norm is 142–424). Within 2 weeks after commencement of therapy, the patient was visibly more alert, no longer complains of chronic fatigue and has relief from dyspnea. In addition she routinely stated that her pain was alleviated after commencing therarpy with Epoetin Omega. She was maintained on Epoetin Omega at a dosage of from one to three vials of Epoetin Omega until the time of death due to cancer about 7 years after the start of the Epoetin Omega treatment.

2. Anemia with breast cancer

A 40 year old female of 164 pounds has no prior history of serious illness and is presented with an inflammatory carcinoma of the right breast. Primary treatment included the chemotherapeutics methotrexate, VINCRISTINE, ADRIAMYCIN and 5-FU IV administered via a portable catheter, and is a very aggressive chemo therapy program, including maximum and concurrent adminstration of the chemo therapy. Ten days after commencement of therapy patient has a low hemoglobin of 11.4 a low HCT of 33.7, and a platelet count of 239 K. Following this onset of anemia, patient commencedtreatment at 150 IU/Kg per week. Further treatment continued using the Marty Abeloff chemotherapy regime that includes additional 5-FU followed by LECOVRIN and CYTOTAXAN subsequent to methotrexate. She also was treated with colony stimulating factor GM CSF to increase white blood cell count but which resulted in other adverse side effects associated with the combined GM-CSF and chemotherapy treatments.

After a month of the above treatments, subject has a RBC of 3.2, a hemoglobin 11.6, a hematocrit of 35.0 and a platelet count of 152 K. During a treatment period of about 3 months, the patient did not suffer from hypertension, but rather maintained a stable blood pressure of about 110–115/ 70–75 mm Hg. During the 3 month treatment period the patient shows an increasing HCT of 36.5% rising to 40% or more and shows an increasing hemoglobin of 11.4, 12.1 and ultimately reaching a hemoglobin level of 17 to 19 routinely in successive months. After continued treatment, doses of Epoetin Omega were reduced to as little as 4,000 IU every third week, the subject returned to a normal RBC of 4.62 M/ul, hemoglobin of 13.4 g/dl HCT of 41.4%

Although the aforementioned subject was a prime candidate for developing anemia of malignant disease due in-part to the aggressive/concurrent chemotherapy, the concurrent treatment with Epoetin Omega prevented the subject from developing the expected anemia, and in fact maintained the subject at above normal hemoglobin levels of 17 to 19. The subject also showed routinely a normal level of HCT, RBC and hemoglobin through out the treatment period. In addition, the subject demonstrated a lack of expected fatigue and generally exhibited a better sense of well being than expected for subject receiving such treatments.

In fact, the patient reported that there was no loss of appetite, but rather a normal appetite; reported no significant nausea and declined the prescribed routine nausea medicine. Patient also reported elimination or reduction of body pain associated with the injection of Epoetin Omega. This patient called the applicant after initial dosing to report that she feared a pain killing medicine had been furnished to her instead of EPO (when in fact it was Epoetin Omega that was given patient). The patient reported that pain departed from her body within one half hour after injection. The patient also suffered from the auto immune disorder of Lupus, and with arthritis, and chronic fatigue syndrome accompanied by fibro myalgia, which patient reports was symptomatically relieved or eliminated by Epoetin Omega injections. In fact, patient reported that after commencing Epoetin Omega therapy, she felt better, had more energy, a better mood and sense of well being, than she did at any time in several years prior, notwithstanding the onset of aggressive cancer, and the aggressive chemo therapy program she entered and maintained. While on aggressive chemo therapy and radiation, she routinely had the energy and desire to go hiking, river rafting, work in her yard, keep her house fully for her family, including meal preparation. The dose of Epoetin Omega administered to the subject was 4,000 to 8000 IU per week, and well below any dose of Epoetin Alfa indicated for possible treatment of anemia associated with chemo therapy. Patient was on therapy at the same time with the same doctor as a patient in the clinic who was dosing Epoetin Alfa at 6 doses of 4,000 IU PER DAY, 6 days a week, or 36 doses of 4,000 IU per week; with such companion patient reporting a hemoglobin of 10 to 11. The patient was the only patient in her program, out of 16 patients, who did not have to suspend chemo therapy. At this moment, patient is without active cancer present by medical tests.

3. Anemia associated with mesothelioma cancer

A subject 170 pound male of 63 yeas old was diagnosed with mesothelioma pleurae lateris dextri. The subject had a history of arterial hypertension, psoriasis and type II diabetes mellitus. At time of intake, subject had a normal RBC of 4.93, a normal HCT of 41%, a normal hemoglobin of 14.2 and a normal platelet count of 348 K and a blood pressure of 150/85. Primary treatment for the cancer included cis-platinum chemotherapy. As a result of chemotherapy treatment, RBC was reduced to 4.46, hemoglobin was reduced to 11.0, HCT was reduced to 36% and platelets were reduced to 296. Epoetin Omega was administered at dose of about 50 IU/kg twice a week over a period of two weeks. The subject also received a dose of peroral iron at about 300/mg/day for the duration of the Epoetin Omega treatment.

During the course of the concomitant chemotherapy, the subject's hemoglobin count was maintained in a normal range of about 12–14 g/dl despite the anticipated anemia associated with cisplatinum chemotherapy. The dose of Epoetin Omega was reduced to 2×25 IU/kg twice per week. His blood pressure was maintained at around 150/90 and even reduced to 140/80 during a brief period. At a later period, the chemotherapy dose was doubled, leading to a slight decrease in hemoglobin count to 11.8 g/dl whereafter, Epoetin Omega was again raised to a dose of 2×50 IU/kg twice a week. FIG. 21A shows the level of hemoglobin count over the course of the chemotherapy, and FIG. 21B shows the delivery schedule of Epoetin Omega relative to the chemotherapy treatment with cisplatinum. These results indicate that low doses of Epoetin Omega at low frequencies are effective at preventing an anemia typically expected from a harsh chemotherapy treatment such as cisplatinum that is known to suppress the erythroid lineage as part of its side effects.

4. Anemia of cancer with chemotherapy/single weekly dose of Epoetin Omega

Three patients in India, having solid tumor cancers fell to a hemoglobin count of about 6.5 to 8 g/dl due at least in-part to cisplatinum chemotherapy. After the application of a once per week dose of 12,000 IU of Epoetin Omega, each patient's hemoglobin count rose, over a period of five to six weeks to a value of about 12 or more g/dl, the target hemoglobin level. Thus, single weekly dosing with Epoetin Omega is shown to be effective in treating an anemia of oncology, particularly an anemia associated with chemotherapy, and more particularly with a cisplatinum based chemotherapy. In addition, the low dosing schedule was effective over a prolonged maintenance period and rather than merely "reducing" the need for transfusions, the treatment with Epoetin Omega was sufficient to raise hemoglobin counts to a normal level and maintain that level for the entire course of the chemotherapy.

EXAMPLE 4

TREATMENT OF A SUBJECT HAVING LIVER DYSFUNCTION/HEPATITIS-C

The patient was a 61 year old 200 pound female with 15 year history of progressively worsening chronic hepatitis-C infection. She was bed ridden, in an oxygen tent, had end-stage liver failure and complained of nausea, dizziness, fluid retention, abdominal pain, diarrhea and chronic fatigue.

She had been unable to take nourishment or tolerate food for several weeks. She also has hypertension. Her medications include SALSALATE, NADOLOL, PREMARIN, ALDACTONE, ENTEX and PRILOSEC. The patient begins a course of treatment with Epoetin Omega administered at 2000 IU (about 22 IU/kg) once every four days. Iron, at about 300 mg/day is also provided as an oral supplement and blood pressure is managed with LASIX and/or PRMARIN. Patient was near terminal condition, bed ridden, on oxygen, and given less than 7 to 21 days to live by her treating physicians, with liver impairment/failure estimated at 90% more. This patient also suffered with Chronic Heart failure.

Following commencement of therapy with Epoetin Omega, within 2 days she could speak again which she had not been able to do for several days prior. Within 3 to 4 days of commencing therapy she no longer required oxygen. Within 4 to 7 days she was out of the bed and returning to a more normal life. The patient continuously reported that within a half hour of injection of Epoetin Omega, the intense pain which was chronic, would leave her body. In fact, the absence of pain would last about 2 to 4 days, and would again disappear on injection of Epoetin Omega.

During a period of about 7 months of treatment with Epoetin Omega, subject did not display the type of anemia expected for her condition, i.e., anemia of chronic inflammatory disease. In contrast, the subject displayed a normal RBC of 4.11, a normal hemoglobin count of 13.4, a normal HCT of 38.2% and a low platelet count of 112. During the Epoetin Omega treatment, the pre existing hypertension exhibited by the subject was maintained at a relatively constant level. Within the first two weeks to one month of treatment, the subject reported substantial increase in energy, a return to substantially normal activity and had significantly decreased body pain, stating that she was without pain. Within 7 to 14 days of INITIAL treatment with Epoetin omega, and arguably with no significant increase in hemoglobin, the patient declined further oxygen treatment and was no longer bed ridden. Within 21 to 30 days the patient returned to a normal lifestyle, ultimately being able to host a wedding for 200 people, to return to her hobby of working in the garden on a regular basis, and resuming for all intents and purposes, a fully normal and active life for a patient of her age. Further, lab tests confirmed, that that the patient had improved liver function independent of a rise in her hemoglobin or RBC counts. In addition, she was able to travel within the USA by motor home to sight see and visit relatives, and to go to the auto race track, with the pit crew who worked for her husband on the racing team.

After about 22 months of continuous Epoetin Omega treatment, the subject was admitted to a hospital for symptoms related to sclerosis of the liver caused by further deteriorating function of the liver. A disease such as hepatitis, that is viral in nature, continues to work adversely on the patient. At time of admission, she still exhibited normal RBC, hemoglobin, and HCT levels with essentially no change in platelet counts since the time these values were last assessed. The patient discontinued use of Epoetin Omega during hospital stay where other therapies were administered for the failing liver condition. Over a short period, RBC count dropped to 2.99, hemoglobin dropped to 10.3, HCT dropped to 29.9 and platelet count dropped from 109 to 93. Subject again complained of increased fatigue and weakness and the course of the disease was then terminal on that stay.

EXAMPLE 5

TREATMENT OF A SUBJECT ADVERSELY EFFECTED BY VASCULAR PAIN ASSOCIATED WITH EPOETINS ALFA AND BETA, BUT NOT EPOETIN OMEGA

A 55 year old woman having terminal renal insufficiency resulting from chronic pyelonephritis suffers from chronic anemia with hemoglobin values of about 7 g/dl. The subject had previously received an unsuccessful kidney transplant. The subject was thereafter treated with a standard dose of 4000 IU of Epoetin Beta three times a week. Although the patient's hemoglobin was raised to a near normal value of 10 g/dl over a three month treatment period, the subject began suffering from a variety of vasculitic complaints (swelling, reddening, itching, spontaneous pain and pressure pain at the lower legs, upper legs and elbow). Treatment with Epoetin Beta was discontinued, and 14 days thereafter these symptoms improved. When Epoetin Beta treatment was renewed, the subject complained of exactly the same symptoms again requiring discontinued use of Epoetin Beta. Discontinued use of Epoetin Beta was again followed by relief of these symptoms, however, the subject's hemoglobin sank below normal levels.

Approximately one month after discontinued Epoetin Beta use, the subject was administered Epoetin Alfa at the same dose of 3×4000 IU/week. The subject showed an improvement in hemoglobin to 10 g % but again experienced the same painful vasculitc symptoms within 16 days requiring discontinued use of Epoetin Alfa.

Approximately two and half months after discontinuing Epoetin Alfa, the subject was administered the same dose of 3×4000 IU/week of Epoetin Omega. Within four weeks, the subject's hemoglobin had improved to a normal value of 14.7% and did not experience any of the adverse side effects of vasculitic pain. After a second kidney transplant which was again unsuccessful, the subject was maintained on dose of 3×2000 IU of Epoetin Omega for several years to keep her hemoglobin count stable in the range of 10–10.6% without any adverse side effects. Thus, the subject experienced no adverse side effects using the same dose of Epoetin Omega as was used with Epoetin Alfa, or Beta. In addition, the dose of Epoetin Omega was able to be reduced to half the amount needed to obtain the equivalent beneficial hemoglobin results obtained using the other Epoetin preparations.

EXAMPLE 6

TREATMENT OF A SUBJECT WITH EPOETIN OMEGA WHO IS NON-RESPONSIVE TO EPOETIN ALFA

A male subject, 46 years of age suffers from familiar gomerulonephritis and dysplasia patellae (incomplete Nail-patella syndrome). Renal histology from age of 13 showed gomerular hypercelularity, thickening of basal capsule, interitial fibrosis, partial tubular atrophy, and 10–20% gloumerular hyalisnation. Renal failure was diagnosed, and first dialysis was performed in 1993. Patient suffers from hyperlipoproteinaemia IIB, arterial hypertension, left ventricular hypertrophy, reduced diastolic relaxation, pericardial fibrosis, anemia, and Lopomata cutis. The patient also had one incidence of mild heart failure.

The above patient participated in a "wash-out" cross-over trial that compared Epoetin Omega to Epoetin Alfa treatment of the chronic anemia associated with renal failure and hemodialysis. Patients were randomized to receive either Epoetin Omega or Epoetin Alfa in a first phase for 16–20 weeks, followed by a wash-out period where no drug was administered for a period until hemoglobin levels returned to pre test (anemic) conditions, at which time in a second phase, the patient received the other of Epoetin Omega or Epoetin Alfa, whichever was not administered in the first phase. This was followed by a second wash-out period. In a third phase, the subject was returned to a different or similar dose of the drug used in the first phase. Thus, each patient served as his own internal control. The initial dose for either of the epoetins was 2×50 IU/kg/week. Doses were fixed during the first 4 weeks of a titration period, and then increased by 25 IU/kg, decreased by the same, or left unchanged depending on the adjustment needed to maintain a hemoglobin count in the target range of 10–12 g/dl.

The aforementioned patient began treatment with Epoetin Omega in the first phase. As shown in FIG. 18A, the response to Epoetin Omega was exceptional, hemoglobin rose from a low baseline of 7.4 and reached the target level within 4 weeks (18A, middle panel). The dose was reduced to 2×25 IU/kg/week during the 6 following weeks, then adjusted again to zero Epoetin Omega for a final period of 4 weeks (18A, top panel, values expressed as total IU/week for this 80 kg individual). Nonetheless, despite the reduction of Epoetin Omega to zero during the last month of the first phase, the patient maintained hemoglobin levels within the target range for the duration of the test phase. As shown in the bottom panel of FIG. 18A, the patient's systolic blood pressure which was borderline for hypertension, i.e., at 140–160 mm Hg, was unchanged or actually decreased during the treatment period with Epoetin Omega.

After a first washout period of several months, the patient's hemoglobin returned to 7.4 g/dl and the second phase was commenced using the same dose, but of Epoetin Alfa as shown in FIG. 18B, (top panel). This patient was non-responsive to Epoetin Alfa, as illustrated by a failure to obtain a target hemoglobin level (18B, middle panel) for the entire duration of the trial, which included repeated increase in doses of Epoetin Alfa to 2×75 IU/kg for 5 weeks, followed by another increase to 2×100 IU/kg and then finally to 2×125 IU/kg/week in the last two weeks of the trial. Not only did the patient fail to respond, but in stark contrast to treatment with Epoetin Omega, the systolic blood pressure of the patient rose substantially above normal by up to 30 mm Hg during the treatment period, which placed the patient in a hypertensive condition for several periods during the treatment.

After a second wash-out period, the patient was again treated with Epoetin Omega at a fixed dose of 1×100 IU/kg, once a week as shown in FIG. 18C (top panel). There was an immediate and steady rise in hemoglobin level that was linear over a 12 week treatment period reaching a near normal level of about 10 g/dl as shown in FIG. 18C, middle panel. Again, in stark contrast to the effects of Epoetin Alfa, the systolic blood pressure of the patient actually decreased rather than increased as shown in FIG. 18C, bottom panel. This data illustrate that some patients that are non-reactors to Epoetin Alfa, may in fact, be exceptionally responsive to Epoetin Omega. It also shows that Epoetin Alfa can contribute substantially to increase in blood pressure, even while providing little or no response to increase hemoglobin levels. Further, the data clearly indicate that Epoetin Omega has an immediate therapeutic benefit, even when administered in once weekly injections at a dose level not useful with Epoetin Alfa.

EXAMPLE 7

USE OF EPOETIN OMEGA IN AN OPERATIVE PROCEDURE TO PREVENT ANEMIA AND PROVIDE FOR AUTOLOGOUS BLOOD TRANSFUSION

Epoetin Omega was used to treat non-anemic patients undergoing elective orthopedic surgery in a randomized, open-labeled controlled trial. Patients were treated with Epoetin Omega at 2×50 IU/kg/week for four weeks s.c. prior to surgery, and supplemented with 2×100 mg iron/week i.v. Control patients were treated only with iron for the same period. The aim was to provide for donation of 3 units of blood (3×500 ml) during the preoperative procedure and to prevent the patient from becoming anemic prior to surgery (i.e., to prevent a hemoglobin of <10 g/dl). Blood donation was possible only if hemoglobin was >/=to 11.0 g/dl. Surgery was scheduled at the end of week 4 of the trial. Blood was donated on Mondays and measurement points for hematological parameters were Mondays and Thursdays preoperative, 2–3 days after surgery, and again 14 days after surgery (at discharge). The donated blood was used for autologous transfusion during surgery.

Figure 19A:
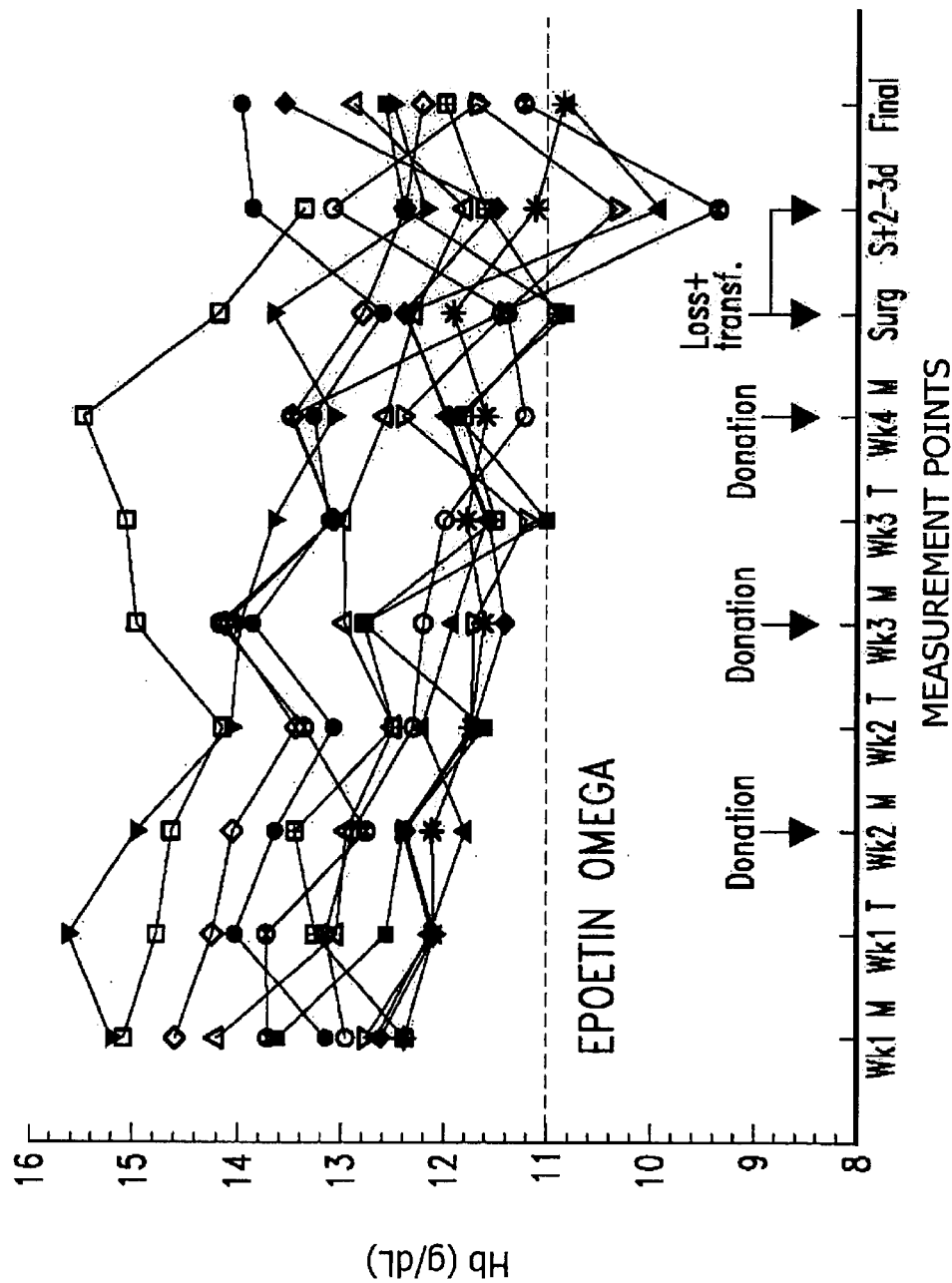
Figure 19B:
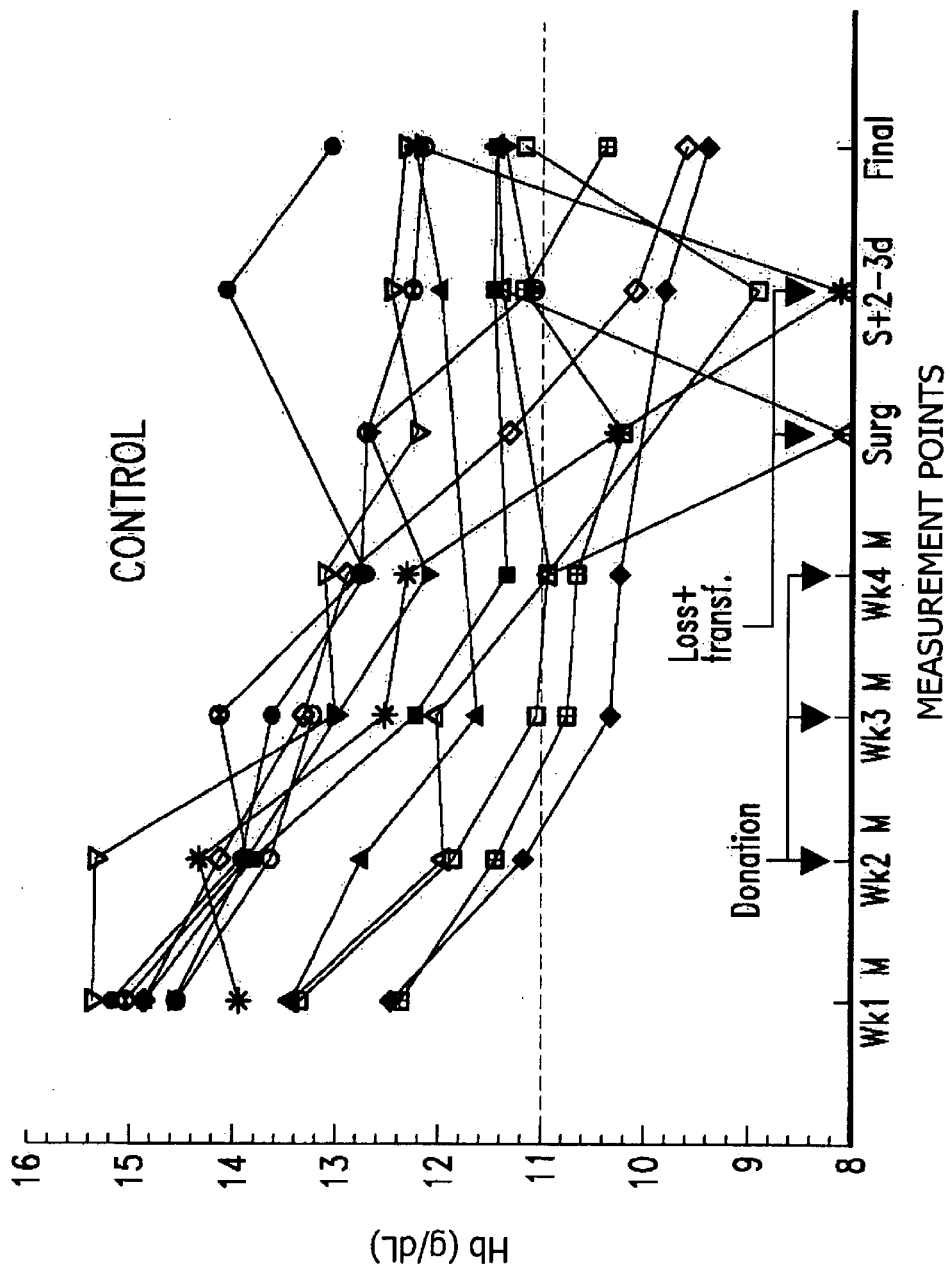
Figure 19C:
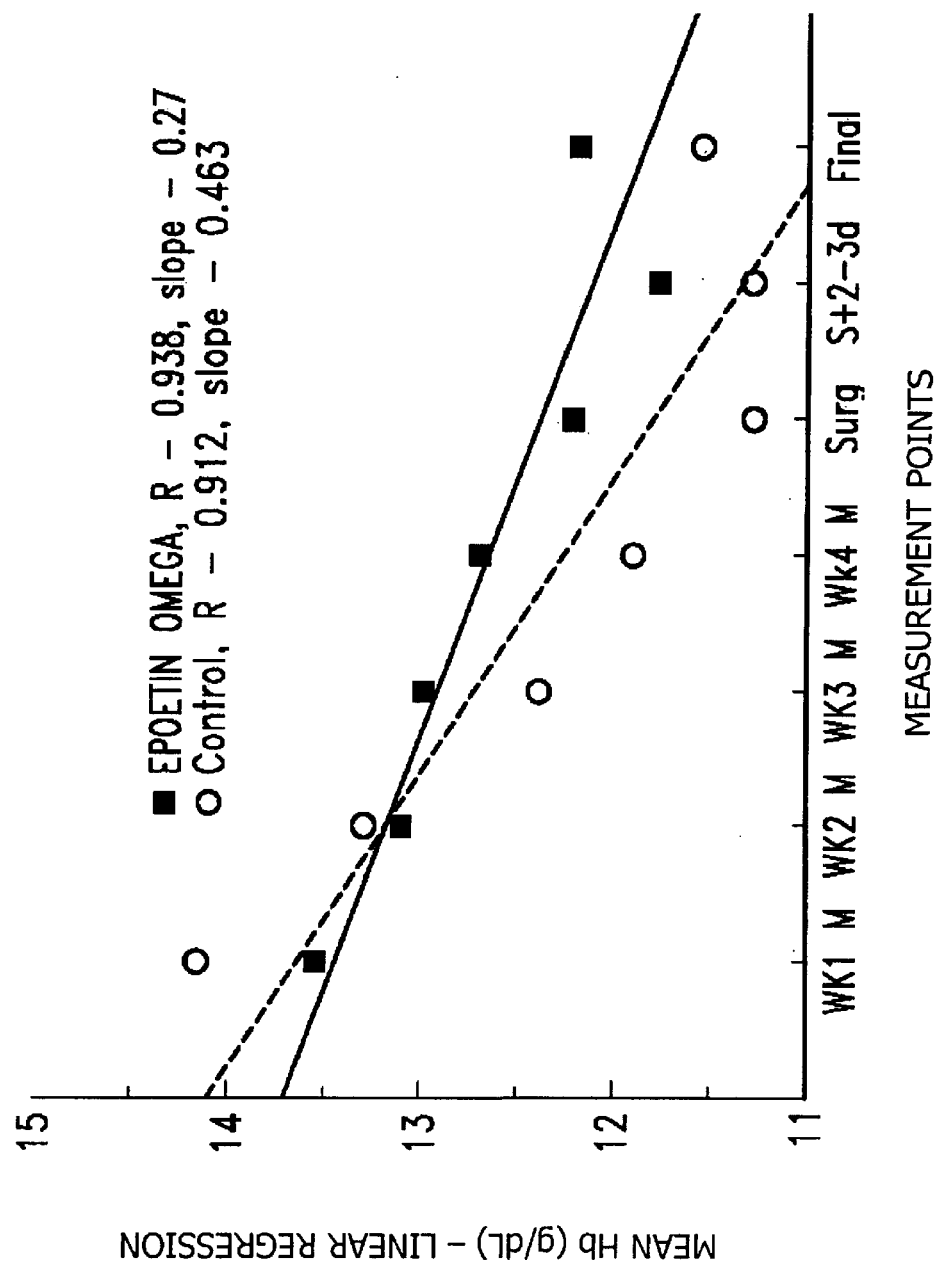
Figure 19D:
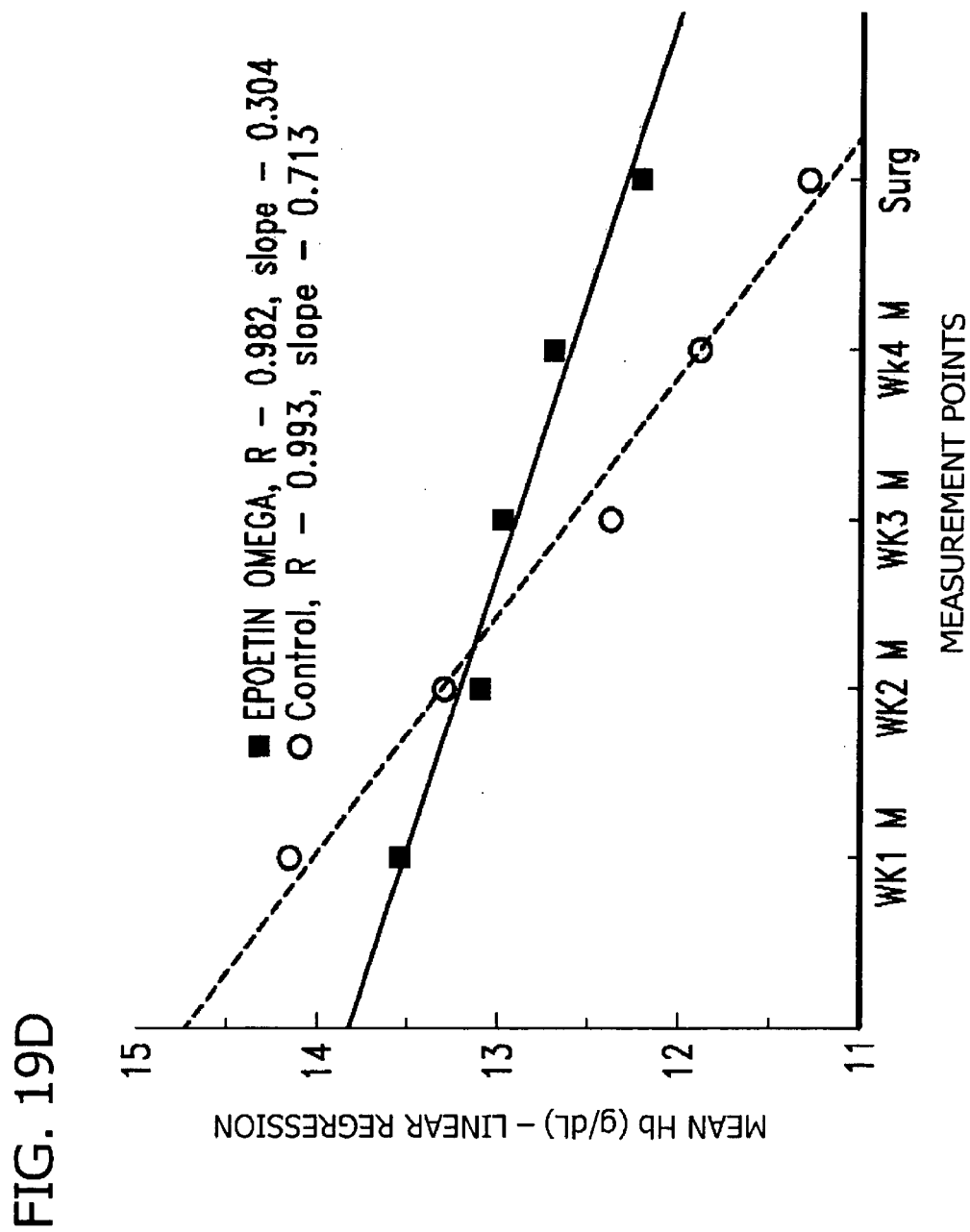

FIG. 19A and B shows individual hemoglobin values during the trial for treated and control groups respectively. Several of the control patients obtained a hemoglobin of less than 11.0 g/dl and were therefore unable to donate the planned amount of blood. In contrast, all of the Epoetin Omega treated patients were able to donate all the blood that was planned. Further, several of the control patients and none of the Epoetin Omega treated patients were anemic before surgery and some became transfusion dependent, i.e., obtaining a hemoglobin </=9.0 g/dl. In addition, the rate of hemoglobin decline was substantially more rapid in the control in comparison to the treated patients. FIGS. 19C and D show that although hemoglobin declined linearly throughout the trial in both groups, both in the period leading to surgery (FIG. 19D) and in the overall period including post surgery (FIG. 19C) the rate of hemoglobin decline was markedly steeper in the control group. FIGS. 20C and D show the RBC and reticulocyte count respectively, for the mean of treated patients in comparison to the control group and illustrates a significant benefit for the treatment group over the control group. FIG. 20D shows that for the average of all patients treated or in the control group, the total serum iron level (TSI) of the treated patients was significantly lower than in the control group indicating a clear increase in erythropoiesis even though the basic condition ordinarily expected for use of other epoetins was not fulfilled, i.e., higher TSI levels. These effects were observed using a dose of Epoetin Omega that is significantly lower than that required for treatment with other epoetins.

The foregoing description and examples are offered by way of illustration and are not intended to limit the scope of the invention. One of ordinary skill in the art will readily understand that the present invention can be practiced in ways that depart from the present disclosure without departing from the invention which is limited only by the following claims.

EXAMPLE 8

USE OF EPOETIN OMEGA IN TREATMENT OF ANEMIA IN CHEMO/RADIATION THERAPY WHERE EPOETIN ALFA FAILS TO WORK A female patient suffering from malignant breast cancer metastasized to the lymph nodes was treated with CMF,. 5FU and NAVALBINE chemotherapy along with daily NEUPOGEN doses and three weekly doses of Epoetin Alfa. The NEUPOGEN is successful at maintaining a low to normal white blood cell count, but the Epoetin Alfa failed to maintain a sufficient RBC count which dropped to the "panic range" of 2.06 and transfusions were necessary. The patient changed to Epoetin Omega injected s.c. two to three times a week at a dose of about 60 IU/kg per administration. One month later, the patient had sufficient strength to undergo external beam radiation of the lungs for period of 9 weeks. The patient continued to take Epoetin Omega during and after the radiation treatment and during subsequent treatment with MUTAMYCIN. At the time of the radiation treatment and thereafter, the patient's RBC, HCT, and hemoglobin levels remained in the low to normal range. The patient reported a feeling of normal vigor and betterment in outlook due to the treatment with Epoetin Omega prior to the radiation therapy, and the improved attitude was reported to be to the cause of her decision to pursue radiation therapy and subsequent chemotherapy. In fact, patient returned to playing tennis, and could play two sets of tennis in a session in one day. Six months after the commencement of the radiation therapy and follow-up chemotherapy, the patients RBC scores were within normal and there was no evidence of tumor markers or tumor tissue by CAT scan. The patient continued chemotherapy on a biweekly basis and continued to take Epoetin Omega at a dose of about 60 IU/kg three to five times a week for at least three months after the CAT scan, and maintained normal RBC counts and continued to report a positive mental outlook, good mood, which she reported and attributed to the use of Epoetin Omega during a prolonged cancer therapy.

EXAMPLE 9

USE OF EPOETIN OMEGA IN A NORMAL PERSON

A 51 year old male is an executive of a pharmaceutical company and suffered for over ten years from CFS, chronic fibro myalgia and muscle pain, including vascular pain, normally most severe in the hips and lower legs, and in the arms, especially the fore arms. Subject has had at all times, normal hemoglobin and RBC. Mirroring the Japanese philosophy of an officer of a company using a company manufactured drug on at least one occasion, subject self administered Epoetin Omega, s.c. Kg in weight (40 IU/Kg). Within less than 5 minutes following administration, generalized pain in the muscles and tissue of subject, including legs and arms, was completely eliminated. Such event was spontaneous and immediate, and thus not associated with any increase in hemoglobin or red blood cell count. This elimination in pain reportedly lasted for 4 to 6 days, and gradually wore off after day 4 till the painful condition returned by day 8. On 12 or more occasions, this person has self administered Epoetin Omega at single dose of 4,000 IU with repeating successful results of significant or elimination of body/muscle/tissue pain. In addition, this patient reports similar improvements in "mood" or "sense of well being". Further, patient has been borderline hypertensive for 20 years with a lower blood systolic pressure ranging from 95 to 105. Following administration of Epoetin Omega, there was no increase in blood pressure, which is monitored daily. This report is consistent with that of the patient in Example 3 who reported on initial use, that she thought she was given a "pain shot" by "mistake" as her body pain from the chronic disease and cancer had subsided within minutes of administration of Epoetin Omega. In that case she has continued over months of treatment with Epoetin Omega to report routine reduction or elimination of body pain upon the administration of Epoetin Omega.

The aforementioned Examples are offered by way of illustration only and do not define the scope of the invention which is limited only by the following claims.

What is claimed is:

1. A method for treating an anemic condition in a subject, the method comprising administering to the subject a therapeutic amount of a recombinant erythropoietin produced in baby hamster kidney cells, the recombinant erythropoietin consisting of Epoetin Omega, wherein the amount of recombinant erythropoietin administered is selected to provide a therapeutic benefit within a treatment period, and wherein the subject is non responsive when treated with a therapeutic amount of Epoetin Alfa or Beta.

2. The method of claim 1 wherein the anemic condition is associated with an anemia associated with a renal condition.

3. The method of claim 1 wherein the therapeutic benefit is selected from the group consisting of increased RBC, increased HCT, increased hemoglobin and increased vigor.

4. The method of claim 1 wherein the recombinant erythropoietin is administered at a dose of about 5 to about 150 IU/Kg, one to three times per week.

5. The method of claim 1 wherein the recombinant erythropoietin is administered at a dose of about 10 to about 100 IU/Kg, one to two times per week.

6. The method of claim 1 wherein the recombinant erythropoietin is administered at a dose of about 10 to about 75 IU/Kg, one to two times per week.

7. The method of claim 1 wherein the recombinant erythropoietin is administered at a dose of about 25 to about 60 IU/Kg, two times per week.

8. The method of claim 1 wherein the recombinant erythropoietin is administered at a dose of about 25 to about 35 IU/Kg, two times per week.

9. The method of claims wherein the recombinant erythropoietin is administered at a dose of about 75 to about 150 IU/Kg, once per week.

10. The method of claim 1 wherein the recombinant erythropoietin is administered at a dose of about 75 to about 100 IU/Kg, once per week.

11. The method of claim 1 wherein the treatment period includes a titration period and the recombinant erythropoietin is administered at an initial dose of about 50 to about 100 IU/Kg per week during the titration period and is adjusted by about 5 to about 25 IU/Kg/week to obtain a hemoglobin count of about 10 to about 12 g/dl.

12. The method of claim 1 wherein the treatment period further includes a maintenance period, and the recombinant erythropoietin is administered at a dose of about 40–60 IU/Kg per week during the maintenance period.

13. A method for treating an anemic condition in a subject, the method comprising administering to the subject a therapeutic amount of a recombinant erythropoietin produced in baby hamster kidney cells, the recombinant erythropoietin consisting of Epoetin Omega, wherein the amount of recombinant erythropoietin administered is selected to provide a therapeutic benefit within a treatment period, and wherein the subject has discontinued a treatment with Epoetin Alfa or Beta due to an adverse side effect of treatment with Epoetin Alfa or Beta.

14. The method of claim 13 wherein the adverse effect is selected from the group consisting of hypertension, headache, arthralgia, nausea, edema, fatigue, diarrhea, vomiting, chest pain, skin rash, dizziness, thrombosis and increased blood platelets.

15. The method of claim 13 wherein the recombinant erythropoietin is administered at a dose of about 5 to about 150 IU/Kg, one to three times per week.

16. The method of claim 13 wherein the recombinant erythropoietin is administered at a dose of about 10 to about 100 IU/Kg, one to two times per week.

17. The method of claim 13 wherein the recombinant erythropoietin is administered at a dose of about 10 to about 75 IU/Kg, one to two times per week.

18. The method of claim 13 wherein the recombinant erythropoietin is administered at a dose of about 25 to about 60 IU/Kg, two times per week.

19. The method of claim 13 wherein the recombinant erythropoietin is administered at a dose of about 25 to about 35 IU/Kg, two times per week.

20. The method of claim 13 wherein the recombinant erythropoietin is administered at a dose of about 75 to about 150 IU/Kg, once per week.

21. The method of claim 13 wherein the recombinant erythropoietin is administered at a dose of about 75 to about 100 IU/Kg, once per week.

22. The method of claim 13 wherein the treatment period includes a titration period and the recombinant erythropoietin is administered at an initial dose of about 50 to about 100 IU/Kg per week during the titration period and is adjusted by about 5 to about 25 IU/Kg/week to obtain a hemoglobin count of about 10 to about 12 g/dl.

23. The method of claim 13 wherein the treatment period further includes a maintenance period, and the recombinant erythropoietin is administered at a dose of about 40–60 IU/Kg per week during the maintenance period.

24. The method of claim 13 wherein the anemic condition is an anemia associated with a renal condition.

25. The method of claim 13 wherein the therapeutic benefit is selected from the group consisting of increased RBC, increased HCT, increased hemoglobin, and increased vigor.

* * * * *

UNITED STATES PATENT AND TRADEMARK OFFICE
CERTIFICATE OF CORRECTION

PATENT NO.        : 7,078,376 B1
APPLICATION NO.   : 09/637962
DATED             : July 18, 2003
INVENTOR(S)       : Thompson It is certified that error appears in the above-identified patent and that said Letters Patent is hereby corrected as shown below:

On the title page: Item [*] Notice : Subject to any disclaimer, the term of this patent is extended Or adjusted under 35 USC 154(b) by (672) days.

Delete the phrase "by 672" and insert -- by 694 days. --.

Signed and Sealed this

Sixteenth Day of January, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,078,376 B1 |
| APPLICATION NO. | : 09/637962 |
| DATED | : July 18, 2006 |
| INVENTOR(S) | : Thompson |

It is certified that error appears in the above-identified patent and that said Letters Patent is hereby corrected as shown below:

On the title page: Item [*] Notice : Subject to any disclaimer, the term of this patent is extended Or adjusted under 35 USC 154(b) by (672) days.

Delete the phrase "by 672" and insert -- by 694 days --.

This certificate supersedes Certificate of Correction issued January 16, 2007.

Signed and Sealed this

Sixth Day of February, 2007

JON W. DUDAS
*Director of the United States Patent and Trademark Office*